United States Patent
Beaton et al.

(10) Patent No.: US 11,230,537 B2
(45) Date of Patent: Jan. 25, 2022

(54) POLYMORPHS OF N-[(3-FLUORO-4-METHOXYPYRIDIN-2-YL)METHYL]-3-(METHOXYMETHYL)-1-({4-[2-OXOPYRIDIN-1-YL)METHYL]PHENYL}METHYL)PYRAZOLE-4-CARBOXAMIDE AS IALLIKREIN INHIBITORS

(71) Applicant: KALVISTA PHARMACEUTICALS LIMITED, Wiltshire (GB)

(72) Inventors: Haydn Beaton, Loughborough (GB); David Malcolm Crowe, Reading (GB); Hannah Joy Edwards, Wiltshire (GB); Nicholas James Griffiths-Haynes, Warwickshire (GB)

(73) Assignee: KalVista Pharmaceuticals Limited, Porton Down (GB)

( * ) Notice: Subject to any disclaimer, the term of this patent is extended or adjusted under 35 U.S.C. 154(b) by 207 days.

(21) Appl. No.: 16/303,334

(22) PCT Filed: Jun. 1, 2017

(86) PCT No.: PCT/GB2017/051579
§ 371 (c)(1),
(2) Date: Nov. 20, 2018

(87) PCT Pub. No.: WO2017/208005
PCT Pub. Date: Dec. 7, 2017

(65) Prior Publication Data
US 2020/0317633 A1 Oct. 8, 2020

Related U.S. Application Data

(60) Provisional application No. 62/344,059, filed on Jun. 1, 2016.

(30) Foreign Application Priority Data

Jun. 1, 2016 (GB) ..................... 1609607

(51) Int. Cl.
*C07D 401/02* (2006.01)

(52) U.S. Cl.
CPC ........ *C07D 401/02* (2013.01); *C07B 2200/13* (2013.01)

(58) Field of Classification Search
CPC .................................................. C07D 401/02
USPC ........................................................ 514/333
See application file for complete search history.

(56) References Cited

U.S. PATENT DOCUMENTS

| | | | |
|---|---|---|---|
| 5,187,157 A | 2/1993 | Kettner et al. | |
| 5,786,328 A | 7/1998 | Dennis et al. | |
| 7,101,878 B1 | 9/2006 | Anderson et al. | |
| 8,207,378 B2 | 6/2012 | Steinmeizer et al. | |
| 9,382,219 B2 | 7/2016 | Das et al. | |
| 9,512,065 B2 | 12/2016 | Northen et al. | |
| 9,533,987 B2 | 1/2017 | Davie et al. | |
| 9,670,157 B2 | 6/2017 | Allan et al. | |
| 9,738,641 B2 | 8/2017 | Edwards et al. | |
| 9,834,513 B2 * | 12/2017 | Allan ...................... A61P 43/00 |
| 10,221,161 B2 | 3/2019 | Edwards et al. | |
| 10,611,758 B2 * | 4/2020 | Davie .................. C07D 401/10 |
| 10,752,607 B2 * | 8/2020 | Beaton ................... A61P 27/02 |
| 10,781,181 B2 * | 9/2020 | Evans ....................... A61P 1/18 |
| 2007/0254894 A1 | 11/2007 | Kane et al. | |
| 2008/0038276 A1 | 2/2008 | Sinha et al. | |
| 2008/0221091 A1 | 9/2008 | Christian et al. | |
| 2009/0163545 A1 | 6/2009 | Goldfarb | |
| 2010/0113782 A1 | 5/2010 | Bolin et al. | |
| 2011/0152533 A1 | 6/2011 | Sinha et al. | |
| 2012/0035168 A1 | 2/2012 | Brandl et al. | |
| 2012/0298326 A1 | 11/2012 | Born | |
| 2014/0213611 A1 | 7/2014 | Evans et al. | |
| 2014/0378474 A1 | 12/2014 | Flohr et al. | |
| 2015/0191421 A1 | 7/2015 | Northen et al. | |

(Continued)

FOREIGN PATENT DOCUMENTS

CA 2730078 A1 1/2010
EA 201200917 12/2012

(Continued)

OTHER PUBLICATIONS

Chilcote et al., "ASP-634: An Oral Drug Candidate for Diabetic Macular Edema", ARVO May 6, 2012-May 9, 2012, Fort Lauderdale, Florida, (Presentation 2240), 1 page.

(Continued)

Primary Examiner — Nizal S Chandrakumar
(74) Attorney, Agent, or Firm — BakerHostetler

(57) ABSTRACT

The invention provides new polymorphs of N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide and salts thereof, pharmaceutical compositions containing them and their use as kallikrein inhibitors in therapy.

11 Claims, 50 Drawing Sheets

FIG. A

(56) References Cited

U.S. PATENT DOCUMENTS

Figure 1A:
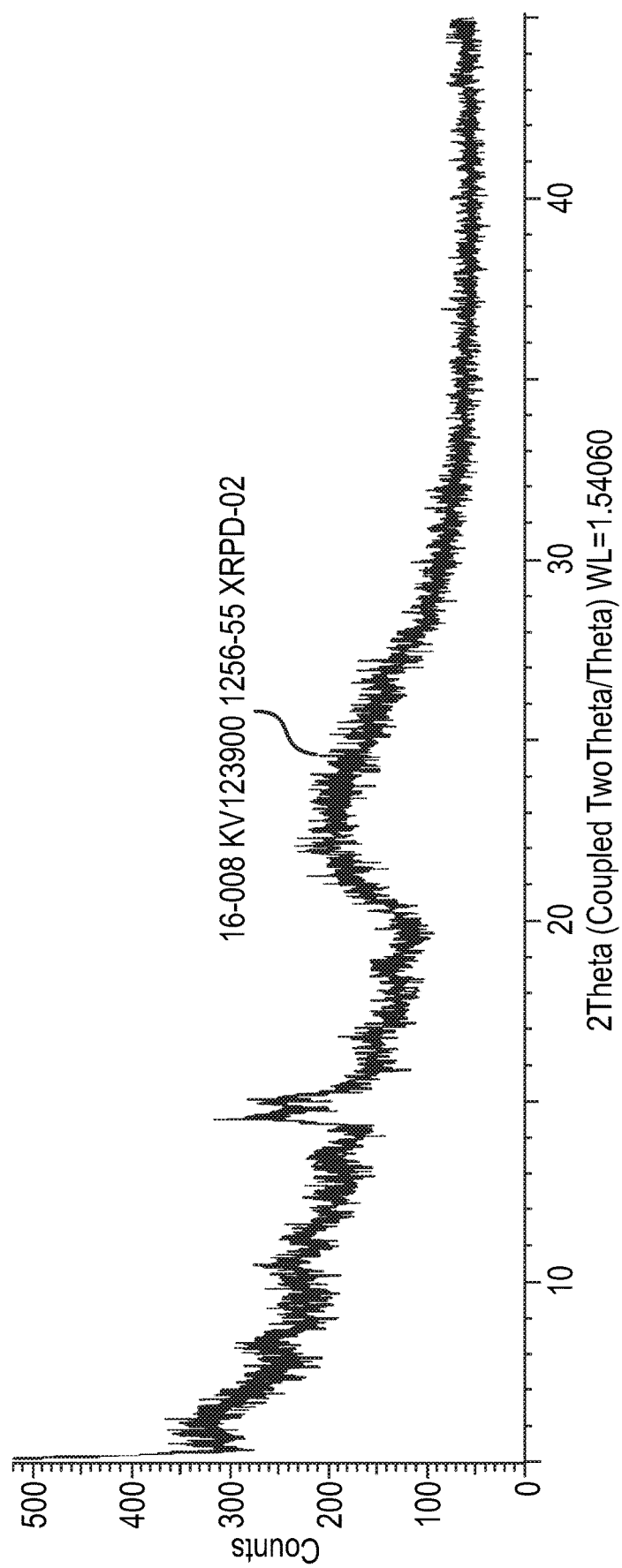

| | | | |
|---|---|---|---|
| 2015/0225450 A1 | 8/2015 | Evans et al. | |
| 2015/0315198 A1 | 11/2015 | Li et al. | |
| 2016/0039752 A1 | 2/2016 | Allan et al. | |
| 2017/0305863 A1 | 10/2017 | Evans et al. | |
| 2018/0319782 A1* | 11/2018 | Davie | C07D 409/14 |

FOREIGN PATENT DOCUMENTS

| | | |
|---|---|---|
| EA | 021359 | 5/2015 |
| EP | 1426364 | 9/2004 |
| EP | 1568698 A1 | 8/2005 |
| EP | 2281885 | 2/2011 |
| EP | 2807157 A1 | 12/2014 |
| EP | 3089746 A1 | 11/2016 |
| EP | 3224256 A1 | 10/2017 |
| JP | 2009-545611 A | 12/2009 |
| JP | 2010-520294 A | 6/2010 |
| JP | 2011-157349 A | 8/2011 |
| JP | 2013-532713 A | 8/2013 |
| RU | 2485114 C2 | 6/2013 |
| WO | WO 1992/004371 | 3/1992 |
| WO | WO 1994/029335 | 12/1994 |
| WO | WO 1995/007921 | 3/1995 |
| WO | 03/35076 A1 | 5/2003 |
| WO | 03/37274 A2 | 5/2003 |
| WO | WO 2003/076458 | 9/2003 |
| WO | WO 2003/091226 | 11/2003 |
| WO | 2004/062657 A1 | 7/2004 |
| WO | 2004/069792 A2 | 8/2004 |
| WO | WO 2005/049578 | 6/2005 |
| WO | 2005/079800 A1 | 9/2005 |
| WO | WO 2005/123680 | 12/2005 |
| WO | 2006/025714 A1 | 3/2006 |
| WO | WO 2006/091459 | 8/2006 |
| WO | 2006/114313 A1 | 11/2006 |
| WO | 2007/001139 A1 | 1/2007 |
| WO | 2007/011626 A2 | 1/2007 |
| WO | WO 2007/113289 | 10/2007 |
| WO | 2008/003697 A1 | 1/2008 |
| WO | WO 2008/016883 | 2/2008 |
| WO | 2007/130842 A2 | 5/2008 |
| WO | WO 2008/049595 | 5/2008 |
| WO | WO 2008/091692 | 7/2008 |
| WO | 2008/119825 A2 | 10/2008 |
| WO | 2008/121670 A1 | 10/2008 |
| WO | 2009/012998 A1 | 1/2009 |
| WO | WO 2009/026407 | 2/2009 |
| WO | 2009/083553 A1 | 7/2009 |
| WO | WO 2009/097141 | 8/2009 |
| WO | 2009/106980 A2 | 9/2009 |
| WO | 2009/114677 A1 | 9/2009 |
| WO | WO 2010/142801 | 12/2010 |
| WO | 2011/075684 A1 | 6/2011 |
| WO | 2011/094496 A2 | 8/2011 |
| WO | WO 2011/118672 | 9/2011 |
| WO | WO 2012/004678 | 1/2012 |
| WO | WO 2012/009009 | 1/2012 |
| WO | WO 2012/017020 | 2/2012 |
| WO | 2012/142308 A1 | 10/2012 |
| WO | 2012/174362 A1 | 12/2012 |
| WO | 2013/005045 A1 | 1/2013 |
| WO | 2013/048982 A1 | 4/2013 |
| WO | 2013/049096 A1 | 4/2013 |
| WO | WO 2013/111107 | 8/2013 |
| WO | WO 2013/111108 | 8/2013 |
| WO | WO 2013/120104 | 8/2013 |
| WO | 2013/130603 A1 | 9/2013 |
| WO | 2014/006414 A1 | 1/2014 |
| WO | 2014/108406 A1 | 7/2014 |
| WO | 2014/108685 A1 | 7/2014 |
| WO | 2014/113712 A1 | 7/2014 |
| WO | WO 2014/108679 A1 | 7/2014 |
| WO | WO 2014/145986 | 9/2014 |
| WO | WO 2014/188211 A1 | 11/2014 |
| WO | WO 2015/022546 | 2/2015 |
| WO | WO 2015/022547 | 2/2015 |
| WO | WO 2015/103317 | 7/2015 |
| WO | WO 2015/134998 | 9/2015 |
| WO | WO 2015/171526 | 11/2015 |
| WO | WO 2015/171527 | 11/2015 |
| WO | WO 2016/011209 | 1/2016 |
| WO | WO 2016/029214 | 2/2016 |
| WO | WO 2016/044662 | 3/2016 |
| WO | WO 2016/083816 | 6/2016 |
| WO | WO 2016/083818 | 6/2016 |
| WO | WO 2016/083820 | 6/2016 |
| WO | WO 2016/138532 | 9/2016 |
| WO | 2017/001924 | 1/2017 |
| WO | WO 2017/001926 | 1/2017 |
| WO | WO 2017/001936 | 1/2017 |
| WO | WO 2017/072020 | 5/2017 |
| WO | WO 2017/072021 | 5/2017 |
| WO | 2017/207983 A1 | 12/2017 |
| WO | 2017/207985 A1 | 12/2017 |
| WO | 2017/207986 A1 | 12/2017 |
| WO | 2017/207989 A1 | 12/2017 |
| WO | 2017/208002 A1 | 12/2017 |
| WO | 2017/208005 A1 | 12/2017 |
| WO | WO 2018/011628 | 1/2018 |
| WO | 2019/106359 A1 | 6/2019 |
| WO | 2019/106375 A1 | 6/2019 |
| WO | 2019/106377 A1 | 6/2019 |

OTHER PUBLICATIONS

Durairaj et al., "Prediction of Vitreal Half-Life Based on Drug Physiochemical Properties: Quantitative Structure-Pharmacokinetic Relationships (QSPKR)", Pharmaceutical Research, 2009, 26(5), 1236-1260.

Lieberman et al. Pharmaceutical Dosage Forms: Tablets, Second Edition, vol. 2, 1989, XP008099925; 15 pages (front page and list of contents included), 145-157.

Marceau et al., "Bradykinin Receptor Ligands: Therapeutic Perspectives", Nature Reviews Drug Discovery, Oct. 2004, 3, pp. 845-852.

Marra et al., "Solution Formulation Development of a VEGF Inhibitor for Intravitreal Injection", 2011, 12(1), 362-370.

Maurice, "Review: Practical Issues in Intravitreal Drug Delivery", Journal of Ocular Pharmacology and Therapeutics, 2001, 17(4), 393-401.

MedicineNet (2004) Web:<http://www.medterms.com>.

Stahl and Wermuth, "Handbook of Pharmaceutical Salts: Properties, Selection and Use", Wiley-VCH, Weinheim, Germany, 2002.

Zhang et al., "Discovery of Highly Potent Small Molecule Kallikrein Inhibitors", Medicinal Chemistry, 2006, vol. 2, No. 6, 545-553.

Babu et al., "A Simple, Sensitive and Selective Fluorogenic Assay to Monitor Plasma Kallikrein Inhibitory Activity of BCX4161 in Activated Plasma", Journal of Allergy and Clinical Immunology, vol. 133, Issue 2, Supplement Feb. 2014, p. AB40.

Bhoola et al., "Bioregulation of Kinins: Kallikreins, Kininogens and Kininases", Pharmacological Rev., 1992, 44(1), 80 pages.

Bhoola et al., "Kallikrein-Kinin Cascade", *Encyclopedia of Respiratory Medicine*, 2006; 483-493.

Bird et al. *Thrombosis and Haemostasis*, "Effects of plasma kallikrein deficiency on haemostasis and thrombosis in mice: Murine Ortholog of the fletcher Trait", 2012, 107, 1141-50.

Björkqvist et al., *Thrombosis and Haemostasis*, "Plasma kallikrein: the bradykinin-producing enzyme", 2013, 110, 399-407.

Bryant et al., "Human plasma kallikrein-kinin system: physiological and biochemical parameters" *Cardiovascular and haematological agents in medicinal chemistry*, 7, 2009, 234-250.

Calderone et al., "1,2,3-Triazol-Carboxanilides and 1,2,3-Triazol-(N-Benzyl)-Carboxamides as BK-Potassium Channel Activators. XII" European Journal of Medicinal Chemistry 43, 2008, pp. 2618-2626.

Campbell, "Towards understanding the kallikrein-kinin system: insights from the measurement of kinin peptides", *Brazilian Journal of Medical and Biological Research* 2000, 33, 665-677.

(56) References Cited

OTHER PUBLICATIONS

CAS Extract for Compound 1086603-52-2, dated Dec. 18, 2008, 2 pages.
CAS Extract for Compound 1094996-93-6, dated Jan. 22, 2009, 1 page.
CAS Extract for Compound 1171693-25-6, dated Aug. 2, 2017, 1 page.
CAS Extract for Compound 1386189-59-8, dated Aug. 3, 2012, 1 page.
Chilcote et al., "ASP-634: An Oral Drug Candidate for Diabetic Macular Edema", ARVO 2012 Mar. 2012, Fort Lauderdale, Florida, Presentation, vol. 53, 2240.
Clermont et al., "Plasma kallikrein mediates retinal vascular dysfunction and induces retinal thickening in diabetic rats", Diabetes, May 2011, 60(5), 1590-1598.
Collis et al., "BCX4161, An Oral Kallikrein Inhibitor: Safety and Pharmacokinetic Results Of a Phase 1 Study In Healthy Volunteers", Journal of Allergy and Clinical Immunology, vol. 133, Issue 2, Supplement, Feb. 2014, p. AB39.
Elman et al., "Randomized trial evaluating ranibizumab plus prompt or deferred laser or triamcinolone plus prompt laser for diabetic macular edema", Ophthalmology, Jun. 2010, 1064-1077.
Evans et al., "Selective Inhibitors of Plasma Kallikrein", Immunopharmacology, May 1996, 32(1-3), 115-116.
Garrett et al. "Peptide Aldehyde Inhibitors of the Kallikreins: an Investigation of Subsite Interactions with Tripeptides Containing Structural Variations at the Amino Terminus", J. Peptide Research, Jul. 1998, 52(1), 60-71.
Griesbacher et al., "Involvement of tissue kallikrein but not plasma kallikrein in the development of symptoms mediated by endogenous kinins in acute pancreatitis in rats" *British Journal of Pharmacology* 137, 2002, 692-700.
Johansen et al., "Assay of Kallikrein Inhibitors and Levels of Acetone-Activated Kallikrein In Plasma Specimens from Reactors to Dextran or to Contrast Media", International Journal Tissue Reactions, 1986, 8, 185-192.
Katsuura et al., "Effects of a highly selective synthetic inhibitor of plasma kallikrein on disseminated intravascular coagulation in rats", *Thrombosis Research*, 1996, 82, 361-368.
Kolte et al. "Biochemical characterization of a novel high-affinity and specific kallikrein inhibitor", British Journal of Pharmacology, 2011, 162(7), 1639-1649.
Lehmann, "Ecallantide (DX-88), a plasma kallikrein inhibitor for the treatment of hereditary angioedema and the prevention of blood loss in on-pump cardiothoracic surgery", Expert Opinion Biol. Ther., Jul. 2008, 8(8), 1187-1199.
Leinweber et al., "Possible Physiological Roles of Carboxylic Ester Hydrolases", Drug Metabolism Reviews, Jan. 1987, 18(4), pp. 379-439.
Liang et al. "Fast-Dissolving Intraoral Drug Delivery Systems", Expert Opinion in Therapeutic Patents, 2001, 11(6), 981-986.
Lieberman et al., Pharmaceutical Dosage Forms: Tablets, Second Edition, vol. 1, 1980; (front page and list of contents); 6 pages.
Lieberman et al., Pharmaceutical Dosage Forms: Tablets, Second Edition, vol. 2, XP008099925, 145-157.
Liu et al., *Nat Med.*, "Hyperglycemia Induced Cerebral Hematoma Expansion is Mediated by Plasma Kallikrein", 2011, 17, 206-210.
Marceau et al., "Bradykinin Receptor Ligands: Therapeutic Perspectives", Nature Reviews Drug Discovery, Oct. 2004, 3, 845-852.
Okada et al., "Development of potent and selective plasmin and plasma kallikrein inhibitors and studies on the structure-activity relationship", Chem. Pharm. Bull., 2000, 48, 1964-1972.
Patel, "Combination Therapy for Age-Related Macular Degeneration", Retina, Jun. 2009, 29(6), pp. S45-S48.
Remington's Pharmaceutical Sciences, Remington: Practice of The Science and Pharmacy; 19th Edition, Mack Publishing Company, 1995; 5 pages.
Revenko et al., *Blood Journal*, "Selective depletion of plasma prekallikrein or coagulation factor XII inhibits thrombosis in mice without increased risk of bleeding", 2011, 118, 5302-5311.
Shori et al., "New Specific Assays for Tonin and Tissue Kallikrein Activities in Rat Submandibular Glands: Assays Reveal Differences in the Effects of Sympathetic and Parasympathetic Stimulation on Proteinases in Saliva", Biochemical Pharmacology, Mar. 17, 1992, 43(6), 1209-1217.
Sturzebecher et al., "Inhibition of Human Mast Cell Tryptase by Benzamidine Derivatives", Biological Chemistry Hoppe-Seyler, Oct. 1992, 373(2), 1025-1030.
Sturzebecher et al., "Novel Plasma Kallikrein Inhibitors of the Benzamidine Type", Brazilian J. Med. Biol. Res, 1994, 27, 1929-1934.
Tanaka et al., *Thrombosis Research* 2004, "Evaluation of a novel kallikrein inhibitor on hemostatic activation in vitro"; 113, 333-339.
Tang et al., "Expression, Crystallization, and Three-Dimensional Structure of the Catalytic Domain of Human Plasma Kallikrein" The Journal of Biological Chemistry vol. 280, No. 49, Dec. 2005, pp. 41077-41089.
Teno et al., "Development of Active Center-Directed Plasmin and Plasma Kallikrein Inhibitors and Studies on the Structure-Inhibitory Activity Relationship", Chemical and Pharmaceutical Bulletin, 1993, 41(6), 1079-1090.
Wermuth et al., Handbook of Pharmaceutical Salts: Properties, Selection and Use, 2002 vol. 24, No. 3, p. 20.
Wermuth, "The Practice of Medicinal Chemistry", 2003, 2nd Ed., pp. 561-585.
Young et al. "Small molecule inhibitors of plasma kallikrein" *Bioorg. Med. Chem. Letts.* 16, 2006, 2034-2036.
Zhang et al., "Discovery of highly potent small molecule kallikrein inhibitors" *Medicinal Chemistry 2*, 545-553.
Tombran-Tink et al., "Opthamology Research", Visual Dysfunction in Diabetes the Science of Patient Impairment and Health Care, 2012, 4 pages.
Ulven et al.; "6-Acylamino-2-amino-4-methylquinolines as potent melanin-concentrating hormone 1 receptor antagonists: Structure-activity exploration of eastern and western parts"; Bioorganic & Medicinal Chemistry Letters; vol. 16 Issue 4; Feb. 2006; p. 1070-1075.
Young et al., "Small Molecule Inhibitors of Plasma Kallikrein", Bioorganic & Medicinal Chemistry Letters, Apr. 2006, 16(7), 2034-2036.
Zhang et al., "Discovery of Highly Potent Small Molecule Kallikrein Inhibitors" Medicinal Chemistry, 2006, 2, pp. 545-553.
Registry No. 1061709-51-0, Chemical Library—FCG Group, Oct. 15, 2008, 1 page.
Registry No. 1062408-24-5, Chemical Library—FCG Group, Oct. 17, 2008, 1 page.
Registry No. 1086603-37-3, Chemical Library—FCG Group, Dec. 18, 2008, 1 page.
Registry No. 1086603-42-0, Chemical Library—AKos Consulting and Solutions GmbH, Chemcats, dated Dec. 18, 2008, 1 page.
Registry No. 1086603-52-2, Chemical Library—FCG Group, Dec. 18, 2008, 1 page.
Registry No. 1094996-93-6, Chemical Library—FCG Group, Jan. 22, 2009, 1 page.
Registry No. 1103271-51-7, Chemical Library—FCG Group, Feb. 9, 2009, 1 page.
Registry No. 1170030-40-6, Chemical Library—FCG Group, Jul. 29, 2009, 1 page.
Registry No. 1171669-07-0, Chemical Library—FCG Group, Aug. 2, 2009, 1 page.
Registry No. 1171693-25-6, Chemical Library—FCG Group, Aug. 2, 2009, 1 page.
Registry No. 1278351-92-0, Chemical Library—FCG Group, Apr. 11, 2011, 1 page.
Registry No. 1280842-43-4, Chemical Library—FCG Group, Apr. 18, 2011, 1 page.
Registry No. 1317328-27-0, Chemical Library—FCG Group, Aug. 14, 2011, 1 page.
Registry No. 1317855-54-1, Chemical Library—FCG Group, Aug. 15, 2011, 1 page.
Registry No. 1318167-86-0, Chemical Library—FCG Group, Aug. 15, 2011, 1 page.

(56) References Cited

OTHER PUBLICATIONS

Registry No. 1318604-27-1, Chemical Library—FCG Group, Aug. 16, 2011, 1 page.
Registry No. 1320653-15-3, Chemical Library—FCG Group, Aug. 21, 2011, 1 page.
Registry No. 1321195-15-6, Chemical Library—FCG Group, Aug. 21, 2011, 1 page.
Registry No. 1321521-84-9, Chemical Library—FCG Group, Aug. 12, 2011, 1 page.
Registry No. 1386189-59-8, Chemical Library—FCG Group, Aug. 3, 2012, 1 page.
Registry No. 1390613-03-2, Chemical Library—FCG Group, Aug. 13, 2012, 1 page.
Registry No. 1569406-35-4, Chemical Library—FCG Group, Mar. 18, 2014, 1 page.
Registry No. 1570266-44-2, Chemical Library—FCG Group, Mar. 19, 2014, 1 page.
Registry No. 1572436-72-6, Chemical Library—FCG Group, Mar. 24, 2014, 1 page.
Registry No. 1572946-10-1, Chemical Library—FCG Group, Mar. 25, 2014, 1 page.
Registry No. 1573976-69-8, Chemical Library—FCG Group, Mar. 26, 2014, 1 page.
Registry No. 1575116-26-5, Chemical Library—FCG Group, Mar. 28, 2014, 1 page.
Registry No. 1575214-30-0, Chemical Library—FCG Group, Mar. 28, 2014, 1 page.
Registry No. 1625594-62-8, Chemical Library—FCG Group, Sep. 24, 2014, 1 page.
Registry No. 879195-72-9, Chemical Library—FCG Group, Apr. 4, 2006, 1 page.
Registry No. 879300-81-9, Chemical Library—FCG Group, Apr. 5, 2006, 1 page.
Registry No. 955867-36-4, Chemical Library—FCG Group, Nov. 23, 2007, 1 page.
Registry No. 955899-78-2, Chemical Library—FCG Group, Nov. 25, 2007, 1 page.
Registry No. 956190-38-8, Chemical Library—FCG Group, Nov. 28, 2007, 1 page.
Registry No. 956290-77-0, Chemical Library—FCG Group, Nov. 29, 2007, 1 page.
Registry No. 956444-80-7, Chemical Library—FCG Group, Dec. 2, 2007, 1 page.
Registry No. 956521-49-6, Chemical Library—FCG Group, Dec. 3, 2007, 1 page.
Registry No. 956529-72-9, Chemical Library—FCG Group, Dec. 3, 2007, 1 page.
Registry No. 956747-39-0, Chemical Library—FCG Group, Dec. 5, 2007, 1 page.
Registry No. 1015534-45-8, Chemical Library—FCG Group, Apr. 18, 2008, 1 page.
Remington's Pharmaceutical Sciences, 19.sup.th Edition, Gennaro, Mack Publishing Company, 1995, 5 pages.
Siebeck et al., "Inhibition of Plasma Kallikrein With Aprotinin in Porcine Endotoxin Shock", The Journal of Trauma, 1993, vol. 34, No. 2, 193-198.
Stahl et al., "Handbook of Pharmaceutical Salts: Properties, Selection and Use", Wiley-VCH, Weinheim, Germany, 2002, 1 page.
STN Registry, "5-Pyrimidinecarboxamide, 1,6-dihydro-N-[1-(6-methyl-1H-benzimidazol-2-yl)ethyl]-2-oxo-2-(1H-1,2,4-triazol-1-ylmethyl)", CAS No. 1422635-37-7, Mar. 8, 2013.
STN Registry, "5-Pyrimidinecarboxamide, N-[1-(1 H-benzimidazol-2-yl)ethyl]-1,6-dihydro-6-oxo-2-(phenoxymethyl)", CAS No. 1434334-41-4, Jun. 5, 2013.
Tanaka et al., Thrombosis Research, Evaluation of a novel kallikrein inhibitor on hemostatic activation in vitro; 2004, 113, 333-339.
Cicardi, DX-88 a recombinant inhibitor of human plasma kallikrein. Efficacy and safety in hereditary and acquired angioedema, Abstracts/Molecular Immunology, 40, 2003, pp. 197-198, Abstract 55.
Patel, et al: Allery and Asthma Proceedings; Ecallantide for treatment of acute attacks of acquired C1 esterase inhibitor deficiency; Jan.-Feb. 2013, vol. 34, No. 1, 72-77.
van den Elzen, et al: Clinic Rev Allerg Immunol; Efficacy of Treatment of Non-hereditary Angioedema; 2018, 54, 412-431.
Aulton's pharmaceutics the design and manufacture of medicines, 3rd Ed, Churchill LivingstoneElsevier, Hungary, 2007, p. 356.
Baeriswyl et al., "A Synthetic Factor XIIa Inhibitor Blocks Selectively Intrinsic Coagulation Initiation", ACS Chem. Biol., 2015, 10(8), 1861-1870.
Bernstein et al., "Polymorphism in Molecular Crystals", 2002, pp. 1-8.
Bouckaert et al., "Synthesis, evaluation and structure-activity relationship of new 3-carboxamide coumarins as FXIIa inhibitors", European Journal of Medicinal Chemistry, 2016, 110, 181-194.
Brittain et al., "Polymorphism in Pharmaceutical Solids", 1999, 234-239.
Byrn et al., "Solid-State Chemistry of Drugs", 1999, 1-17, 233-247.
Clermont, et al: IOVS, Plasma Kallikrein Mediates Vascular Endothelial Growth Factor-Induced Retinal Dysfunction and Thickening, May 2016, vol. 57, No. 6, 2391-2399.
Hilfiker et al., "Polymorphism: In the Pharmaceutical Industry", 2006, 1-19.
Lieberman et al., Pharmaceutical Dosage Forms: Tablets, vol. 1, 1980, pp. 145-157.
Obach, "Prediction of human clearance of twenty-nine drugs from hepatic microsomal intrinsicclearance data: An examination of in vitro half-life approach and nonspecific binding tomicrosomes", Drug Metabolism and Disposition, 1999, 27(11), 1350-13592.
Wang et al., "Determination of In Vitro Permeability of Drug Candidates through a Caco-2 Cell Monolayer by Liquid Chromatography/Tandem Mass Spectrometry" J. Mass Spectrom 35(1); 71-76, 2000.
Pace, et al., "4-Hydroxy-5-pyrrolinone-3-carboxamide HIV-1 integrase inhibitors", Bioorganic & Medicinal Chemistry Letters., 18, Jun. 2008, pp. 3865-3869.
Registry No. 1086603-37-3, Chemical Library—AKos Consulting and Solutions GmbH, Chemcats, dated Dec. 18, 2008, 1 page.
Registry No. 1086603-52-2, Chemical Library—AKos Consulting and Solutions GmbH, Chemcats, dated Dec. 18, 2008, 1 page.
Registry No. 1094996-93-6, Chemical Library—AKos Consulting and Solutions GmbH, Chemcats, dated Jan. 22, 2009, 1 page.
Registry No. 1171693-25-6, Chemical Library—Ambinter, Chemcats, dated Aug. 2, 2017, 1 page.
Registry No. 1318167-86-0, Chemical Library—FCH Group, Chemcats, dated Aug. 15, 2011, 1 page.
Registry No. 1320653-15-3, Chemical Library—FCH Group, Aug. 21, 2011, 1 page.
Registry No. 1386189-59-8, Chemical Library—Ukrorgsyntez Ltd., Chemcats, dated Aug. 3, 2012, 1 page.
Registry No. 1569406-35-4, Chemical Library—FCH Group, Mar. 18, 2014, 1 page.
Registry No. 1570266-44-2, Chemical Library—FCH Group, dated Mar. 19, 2014, 1 page.
Registry No. 1572436-72-6, Chemical Library—FCH Group, dated Mar. 24, 2014, 1 page.
Registry No. 1572946-10-1, Chemical Library—FCH Group, Mar. 25, 2014, 1 page.
Registry No. 1573976-69-8, Chemical Library—FCH Group, dated Mar. 26, 2014, 1 page.
Registry No. 1575214-30-0, Chemical Library—FCH Group, dated Mar. 28, 2014, 1 page.
Registry No. 1580327-09-8, Chemical Library—FCH Group, dated Apr. 4, 2014, 1 page.
Remington: Practice of the Science and Pharmacy; 19th Edition; Mack Publishing Company, 1995, 5 pages.
Garrett et al. "Peptide Aldehyde Inhibitors of the Kallikreins: an Investigation of Subsite Interactions with Tripeptides Containing Structural Variations at the Amino Terminus", J. Peptide Research, Jul. 1998, 52(1), pp. 60-71.
Griesbacher et al., "Involvement of Tissue Kallikrein But Not Plasma Kallikrein in the Development of Symptoms Mediated by

(56) References Cited

OTHER PUBLICATIONS

Endogenous Kinins in Acute Pancreatitis in Rats", British Journal of Pharmacology, 2002, 137, pp. 692-700.
Ikeda et al., "Host Stromal Bradykinin B.sub.2 Receptor Signaling Facilitates Tumor-Associated Angiogenesis and Tumor Growth", Cancer Research, Aug. 2004, 64, 5178-5185.
International Patent Application No. PCT/GB2015/053613: International Search Report dated Jun. 2, 2016, 5 pages.
International Patent Application No. PCT/GB2015/053613: Written Opinion dated Jun. 2, 2016, 9 pages.
International Search Report for PCT/GB2014/051592 completed Jul. 23, 2014.
Jaffa et al., "Plasma Prekallikrein a Risk Marker for Hypertension and Nephropathy in Type 1 Diabetes", Diabetes, May 2003, vol. 52, 1215-1221.
Katsuura et al., "Effects of a Highly Selective Synthetic Inhibitor of Plasma Kallikrein on Disseminated Intravascular Coagulation in Rats", Thrombosis Research, 1996, vol. 82, No. 4, 361-368.
Kenniston, J Bio Chem, "Inhibition of Plasma Kallikrein by a Highly Specific Active Site Blocking Antibody", vol. 289 (34), 2014, 23596-23608.
Kolte et al., "Biochemical characterization of a novel high-affinity and specific plasma kallikrein inhibitor", British Journal of Pharmacology, 2011, 162, 1639-1649.
Lehmann, "Ecallantide (DX-88), A Plasma Kallikrein Inhibitor for the Treatment of Hereditary Angioedema and the Prevention of Blood Loss in On-Pump Cardiothoracic Surgery", Expert Opinion on Biological Therapy, Jul. 2008, 8(8), 1187-1199.
Liang et al. "Fast-Dissolving Intraoral Drug Delivery Systems", Expert Opinion in Therapeutic Patents, Jun. 2001, 11(6), pp. 981-986.
Lieberman et al. Pharmaceutical Dosage Forms: Tablets, Second Edition, vol. 2, XP008099925; 15 pages (front page and list of contents included), 145-157.
Lieberman et al., Pharmaceutical Dosage Forms: Tablets, Second Edition, vol. 1, 1980; (front page and list of contents included) 6 pages.
Lussis et al.; "A single synthetic small molecule that generates force against a load"; Nature Nanotechnology; vol. 6; 2011; p. 553-557.
Luthin et al., "The Discovery of Novel Small Molecule Non-peptide Gonadotropin Releasing Hormone (GnRH) Receptor Antagonists" Bioorg Med Chem Lett, 12, 2002, pp. 3467-3470.
Okada et al., "Development of Potent and Selective Plasmin and Plasma Kallikrein Inhibitors and Studies on the Structure-Activity Relationship", Chem Pharm. Bull., Sep. 2000, 48, pp. 1964-1972.
Patel, "Combination Therapy for Age-Related Macular Degeneration", Retina, Jun. 2009, 29(6), S45-S48.
Prassas, "Unleashing the therapeutic potential of human kallikrein-related serine proteases", Nature Reviews Drug Discovery, vol. 14, 183-202, 2015.
PubChem Compound 40150888 May 30, 2009.
PubChem Compound 51143945 May 3, 2011.
PubChem Compound 52011740 May 20, 2011.
PubChem Compound 52011741 May 20, 2001.
PubChem Compound 52011742 May 20, 2011.
PubChem Compound 52011935 May 20, 2011.
PubChem Compound 52011936 May 20, 2011.
PubChem Compound 52011937 May 20, 2011.
PubChem Compound 52011938 May 20, 2011.
PubChem Compound 55389827 Jan. 25, 2012.
PubChem Compound 55408484 Jan. 25, 2012.
PubChem Compound 55408530 Jan. 25, 2012.
PubChem Compound 55408677 Jan. 25, 2012.
PubChem Compound 55408742 Jan. 25, 2012.
PubChem Compound 55408894 Jan. 25, 2012.
PubChem Compound 55438190 Jan. 25, 2012.
PubChem Compound 55494217 Jan. 25, 2012.
PubChem Compound 55650494 Jan. 25, 2012.
PubChem Compound 60376550 Oct. 18, 2012.
PubChem Compound ID 22830339 Dec. 5, 2007.
PubChem Compound ID 24488625 Feb. 29, 2008.
PubChem Compound ID 38284485 May 29, 2009.
PubChem Compound ID 38284487 May 29, 2009.
PubChem Compound ID 46438580 Jul. 23, 2010.
Registry No. 1027627-81-1, Chemical Library—FCG Group, Jun. 12, 2008, 1 page.
Registry No. 1028093-96-0, Chemical Library—FCG Group, Jun. 13, 2008, 1 page.
Registry No. 1028094-50-9, Chemical Library—FCG Group, Jun. 13, 2008, 1 page.
Registry No. 1028096-34-5, Chemical Library—FCG Group, Jun. 13, 2008, 1 page.
Registry No. 1028361-95-6, Chemical Library—FCG Group, Jun. 16, 2008, 1 page.
Ambinter Sarl: "1 H-Pyrazole-4-carboxamides" In: Chemical Catalog, 11; Sep. 2011 (Sep. 11, 2011), Ambinter SARL, XP055601375.
Babu et al., "A Simple, Sensitive and Selective Fluorogenic Assay to Monitor Plasma Kallikrein Inhibitory Activity of BCX4161 in Activated Plasma", Journal of Allergy and Clinical Immunology, Feb. 2014,133(2), 1 page.
Babu, "Drug Discovery at BioCryst Pharmaceuticals Inc.", Presentation, http://files.shareholder.com/downloads/BCRX/0x0x403076/97a18d6e-1621-4fc6--8f5fd0828bddab4f/, Sep. 16, 2010, 18 pages.
Bhoola et al., "Bioregulation of Kinins: Kallikreins, Klninogens and Kininases", Pharmacological Rev., 1992, 44(1), 80 pages.
Bhoola et al., "Kallikrein-Kinin Cascade" Encyclopedia of Respiratory Medicine, 2006, pp. 483-493.
Bjorkqvist et al., "Plasma kallikrein: the bradykinin-producing enzyme", Thrombosis and Haemotasis, 2013, 110, 399-407.
Bryant et al., "Human Plasma Kallikrein-Kinin System: Physiological and Biochemical Parameters", Cardiovascular and Haematological Agents in Medicinal Chemistry, Jul. 2009, pp. 234-250.
Caddick et al., "Convenient Synthesis of Protected Primary Amines from Nitriles", Tetrahedron Letters, Apr. 29, 2000, 41(18), 3513-3516.
Campbell, "Towards Understanding the Kallikrein-Kinin System: Insights from the Measurement of Kinin Peptides", Brazilian Journal of Medical and Biological Research, 2000, 33(6), 665-677.
Cannon, Chapter Nineteen in Burger's Medicinal Chemistry and Drug Discovery, Fifth Edition, vol. I: Principles and Practice, Wiley-Interscience 1995, pp. 783-802.
CAS abstract accession No. 1990:515202, corresponding to Ried et al. Liebigs Annalen der Chemie, 1990, 8, 2 pages.
CAS abstract accession No. 2013:1177162, corresponding to Ye et al. Chemical Science, 2013, 4(9), 4 pages.
CAS abstract accession No. 2013:1592386, corresponding to FR2989085 A1 (Commissariat Energie Atomique), 3 pages.
CAS abstract accession Nos. 2009:769551 and 2009:846114, corresponding to U.S. Publication 2009-0163545A1, 5 pages.
CAS Extract for Compound 1028094-50-9, dated Jun. 13, 2008, 1 page.
CAS extract for Compound 1180236-10-5; Sep. 4, 2009.
CAS extract for Compound 1180808-34-7; Sep. 6, 2009.
CAS Extract for Compound 1197490-19-9, dated Dec. 16, 2009, 1 page.
CAS Extract for Compound 120842-4-4, dated Apr. 18, 2011, 1 page.
CAS Extract for Compound 120842-43-4, dated Apr. 18, 2011, 1 page.
CAS extract for Compound 1288265-35-9; May 1, 2011.
CAS extract for Compound 1288488-40-3; May 1, 2011.
CAS extract for Compound 1288531-53-2; May 1, 2011.
CAS extract for Compound 1293757-54-6; May 12, 2011.
CAS extract for Compound 1297493-36-7; May 19, 2011.
CAS Extract for Compound 1386962-55-5, dated Aug. 6, 2012, 1 page.
CAS Extract for Compound 1388550-15-9, dated Aug. 9, 2012, 1 page.
CAS extract for Compound 1424383-07-2; Mar. 15, 2013.
CAS Extract for Compound 1626023-22-0, dated Sep. 25, 2014, 1 page.
CAS Structures cited in WO201683818 Written Opinion dated Jun. 2, 2016, 290 pages.

(56) References Cited

OTHER PUBLICATIONS

Chemical Abstract Service, Chemcats, RN 1424383-07-2, Mar. 15, 2013.
Chemical Abstracts Registry No. 1147797-44-1, indexed in the Registry file on STN CAS Online May 20, 2009.
Chemical Abstracts Registry No. 1217027-87-6, indexed in the Registry file on STN CAS Online Apr. 5, 2010.
Chemical Abstracts Registry No. 1241137-33-6, indexed in the Registry file on STN CAS Online Sep. 15, 2010.
Chemical Abstracts Registry No. 1295467-87-6, indexed in the Registry file on STN CAS Online May 16, 2011.
Chemical Abstracts Registry No. 1296846-83-7, indexed in the Registry file on STN CAS Online May 18, 2011.
Chemical Abstracts Registry No. 1297526-11-4, indexed in the Registry file on STN CAS Online May 19, 2011.
Chemical Abstracts Registry No. 1389653-06-8, indexed in the Registry file on STN CAS Online Aug. 12, 2012.
Chemical Abstracts Registry No. 1575116-26-5, indexed in the Registry file on STN CAS Online Mar. 28, 2014.
Chemical Abstracts Registry No. 942731-43-3, indexed in the Registry file on STN CAS Online Jul. 19, 2007.
Chemical Abstracts Registry No. 955899-78-2, indexed in the Registry file on STN CAS Online on Nov. 25, 2007.
Chilcote et al., "ASP-634: An Oral Drug Candidate for Diabetic Macular Edema", ARVO May 6, 2012-May 9, 2012, Fort Lauderdale, Florida, Presentation 2240.
Collis et al., "BCX4161, An Oral Kallikrein Inhibitor: Safety and Pharmacokinetic Results of a Phase 1 Study in Healthy Volunteers", Journal of Allergy and Clinical Immunology, Feb. 2014, 133(2), 1 page.
Colman, "Plasma and tissue kallikrein in arthritis and inflammatory bowel disease", Immunopharmacology, 1999, 43, 103-108.
Davis III et al., "Biological activities of C1 inhibitor", Molecular Immunology, 2008, 45, 4057-4063.
Elman et al., "Randomized Trial Evaluating Ranibizumab Plus Prompt or Deferred Laser or Triamcinolone Plus Prompt Laser for Diabetic Macular Edema", Ophthalmology, Jun. 2010, 117(6), e35, 1064-1077.
Enamine website on Jul. 25, 2013 from the Internet Archive Way Back Machine {https://web.archive.org/web/20130725053127/http://www.enamine.net/index.php?option=com_content&task=view&id=22.
Feener at al., "Role of plasma kallikrein in diabetes and metabolism", Thrombosis and Haemostasis, Sep. 2013, 110(3), 434-441.
Chemical & Engineering News, Feb. 24, 2003, pp. 32-35.
Lussis et al.; "A single synthetic small molecule that generates force against a load"; Nature Nanotechnology; vol. 6; 2011; p. S1-525 (Supplemental Information).
Tombran-Tink et al.; "Visual Dysfunction in Diabetes: The Science of Patient Impairment and Health Care"; Humana Press; 2012; p. 34.
Registry No. 1572751-33-7, Chemical Library—FCH Group, dated Mar. 24, 2014.
Rodriguez-Spong, et al: General principles of pharmaceutical solid polymorphism: a supramolecular perspective; 56, 2004, 241-274.
DeNinno, M. P. et al., "1,5-Substituted nipecotic amides: Selective PDE8 inhibitors displaying diastereomer-dependent microsomal stability", Bioorganic & Medicinal Chemistry Letters, 2011, vol. 21, 3095-3098.
Golub, et al., "Molecular Classification of Cancer: Class Discovery and Class Prediction by Gene Expression Monitoring", Science, Oct. 15, 1999, vol. 286, 531-537.
Lala, et al., "Role of nitric oxide in tumor progression: Lessons from experimental tumors", Cancer and Metastasis Reviews, 1998, 17: 91-106.

* cited by examiner

XRPD - Besylate salt (acetone, ethyl acetate, THF, acetonitrile)

16-0378

15PM1164_21_1

15PM1164_23_1

16-0380

16-0381

15PM1164_27_1

POLYMORPHS OF
N-[(3-FLUORO-4-METHOXYPYRIDIN-2-YL)
METHYL]-3-(METHOXYMETHYL)-1-
({4-[(2-OXOPYRIDIN-1-YL)METHYL]PHENYL}
METHYL)PYRAZOLE-4-CARBOXAMIDE AS
IALLIKREIN INHIBITORS

CROSS-REFERENCE TO RELATED
APPLICATIONS

This application is the National Stage of International Patent Application No. PCT/GB2017/051579, filed Jun. 1, 2017, which claims priority from Great Britain Patent Application No. 1609607.5, filed Jun. 1, 2016, and U.S. Patent Application No. 62/344,059, filed Jun. 1, 2016, the disclosures of each of which are incorporated herein by reference in their entireties for any and all purposes.

The present invention relates to new polymorphs of a plasma kallikrein inhibitor, a pharmaceutical composition containing them and their use in therapy.

BACKGROUND TO THE INVENTION

Inhibitors of plasma kallikrein have a number of therapeutic applications, particularly in the treatment of retinal vascular permeability associated with diabetic retinopathy, diabetic macular edema and hereditary angioedema.

Plasma kallikrein is a trypsin-like serine protease that can liberate kinins from kininogens (see K. D. Bhoola et al., "Kallikrein-Kinin Cascade", *Encyclopedia of Respiratory Medicine*, p 483-493; J. W. Bryant et al., "Human plasma kallikrein-kinin system: physiological and biochemical parameters" Cardiovascular and haematological agents in medicinal chemistry, 7, p 234-250, 2009; K. D. Bhoola et al., *Pharmacological Rev.*, 1992, 44, 1; and D. J. Campbell, "Towards understanding the kallikrein-kinin system: insights from the measurement of kinin peptides", *Brazilian Journal of Medical and Biological Research* 2000, 33, 665-677). It is an essential member of the intrinsic blood coagulation cascade although its role in this cascade does not involve the release of bradykinin or enzymatic cleavage. Plasma prekallikrein is encoded by a single gene and synthesized in the liver. It is secreted by hepatocytes as an inactive plasma prekallikrein that circulates in plasma as a heterodimer complex bound to high molecular weight kininogen which is activated to give the active plasma kallikrein. Kinins are potent mediators of inflammation that act through G protein-coupled receptors and antagonists of kinins (such as bradykinin antagonists) have previously been investigated as potential therapeutic agents for the treatment of a number of disorders (F. Marceau and D. Regoli, Nature Rev., Drug Discovery, 2004, 3, 845-852).

Plasma kallikrein is thought to play a role in a number of inflammatory disorders. The major inhibitor of plasma kallikrein is the serpin C1 esterase inhibitor. Patients who present with a genetic deficiency in C1 esterase inhibitor suffer from hereditary angioedema (HAE) which results in intermittent swelling of face, hands, throat, gastro-intestinal tract and genitals. Blisters formed during acute episodes contain high levels of plasma kallikrein which cleaves high molecular weight kininogen liberating bradykinin leading to increased vascular permeability. Treatment with a large protein plasma kallikrein inhibitor has been shown to effectively treat HAE by preventing the release of bradykinin which causes increased vascular permeability (A. Lehmann "Ecallantide (DX-88), a plasma kallikrein inhibitor for the treatment of hereditary angioedema and the prevention of blood loss in on-pump cardiothoracic surgery" *Expert Opin. Biol. Ther.* 8, p 1187-99).

The plasma kallikrein-kinin system is abnormally abundant in patients with advanced diabetic macular edema. It has been recently published that plasma kallikrein contributes to retinal vascular dysfunctions in diabetic rats (A. Clermont et al. "Plasma kallikrein mediates retinal vascular dysfunction and induces retinal thickening in diabetic rats" *Diabetes,* 2011, 60, p 1590-98). Furthermore, administration of the plasma kallikrein inhibitor ASP-440 ameliorated both retinal vascular permeability and retinal blood flow abnormalities in diabetic rats. Therefore a plasma kallikrein inhibitor should have utility as a treatment to reduce retinal vascular permeability associated with diabetic retinopathy and diabetic macular edema.

Plasma kallikrein also plays a role in blood coagulation. The intrinsic coagulation cascade may be activated by factor XII (FXII). Once FXII is activated (to FXIIa), FXIIa triggers fibrin formation through the activation of factor XI (FXI) thus resulting in blood coagulation. Plasma kallikrein is a key component in the intrinsic coagulation cascade because it activates FXII to FXIIa, thus resulting in the activation of the intrinsic coagulation pathway. Furthermore, FXIIa also activates further plasma prekallikrein resulting in plasma kallikrein. This results in positive feedback amplification of the plasma kallikrein system and the intrinsic coagulation pathway (Tanaka et al. (*Thrombosis Research* 2004, 113, 333-339); Bird et al. (*Thrombosis and Haemostasis,* 2012, 107, 1141-50).

Contact of FXII in the blood with negatively charged surfaces (such as the surfaces of external pipes or the membrane of the oxygenator that the blood passes during cardiopulmonary bypass surgery) induces a conformational change in zymogen FXII resulting in a small amount of active FXII (FXIIa). The formation of FXIIa triggers the formation of plasma kallikrein resulting in blood coagulation, as described above. Activation of FXII to FXIIa can also occur in the body by contact with negatively charged surfaces on various sources (e.g. bacteria during sepsis, RNA from degrading cells), thus resulting in disseminated intravascular coagulation (Tanaka et al. (*Thrombosis Research* 2004, 113, 333-339)).

Therefore, inhibition of plasma kallikrein would inhibit the blood coagulation cascade described above, and so would be useful in the treatment of disseminated intravascular coagulation and blood coagulation during cardiopulmonary bypass surgery where blood coagulation is not desired. For example, Katsuura et al. (*Thrombosis Research,* 1996, 82, 361-368) showed that administration of a plasma kallikrein inhibitor, PKSI-527, for LPS-induced disseminated intravascular coagulation significantly suppressed the decrease in platelet count and fibrinogen level as well as the increase in FDP level which usually occur in disseminated intravascular coagulation. Bird et al. (*Thrombosis and Haemostasis,* 2012, 107, 1141-50) showed that clotting time increased, and thrombosis was significantly reduced in plasma kallikrein-deficient mice. Revenko et al. (*Blood,* 2011, 118, 5302-5311) showed that the reduction of plasma prekallikrein levels in mice using antisense oligonucleotide treatment resulted in antithrombotic effects. Tanaka et al. (Thrombosis Research 2004, 113, 333-339) showed that contacting blood with DX-88 (a plasma kallikrein inhibitor) resulted in an increase in activated clotting time (ACT). Lehmann et al. (*Expert Opin. Biol. Ther.* 2008, 1187-99) showed that Ecallantide (a plasma kallikrein inhibitor) was found to delay contact activated induced coagulation. Lehmann et al. conclude that Ecallantide "had in vitro anticoagulant effects as it inhibited the intrinsic pathway of coagulation by inhibiting plasma kallikrein".

Plasma kallikrein also plays a role in the inhibition of platelet activation, and therefore the cessation of bleeding. Platelet activation is one of the earliest steps in hemostasis, which leads to platelet plug formation and the rapid cessation of bleeding following damage to blood vessels. At the site of vascular injury, the interaction between the exposed collagen and platelets is critical for the retention and activation of platelets, and the subsequent cessation of bleeding.

Once activated, plasma kallikrein binds to collagen and thereby interferes with collagen-mediated activation of platelets mediated by GPVI receptors (Liu et al. (*Nat Med.*, 2011, 17, 206-210)). As discussed above, plasma kallikrein inhibitors reduce plasma prekallikrein activation by inhibiting plasma kallikrein-mediated activation of factor XII and thereby reducing the positive feedback amplification of the kallikrein system by the contact activation system.

Therefore, inhibition of plasma kallikrein reduces the binding of plasma kallikrein to collagen, thus reducing the interference of plasma kallikrein in the cessation of bleeding. Therefore plasma kallikrein inhibitors would be useful in the treatment of treating cerebral haemorrhage and bleeding from post operative surgery. For example, Liu et al. (*Nat Med.*, 2011, 17, 206-210) demonstrated that systemic administration of a small molecule PK inhibitor, ASP-440, reduced hematoma expansion in rats. Cerebral hematoma may occur following intracerebral haemorrhage and is caused by bleeding from blood vessels into the surrounding brain tissue as a result of vascular injury. Bleeding in the cerebral haemorrhage model reported by Liu et al. was induced by surgical intervention involving an incision in the brain parenchyma that damaged blood vessels. These data demonstrate that plasma kallikrein inhibition reduced bleeding and hematoma volume from post operative surgery. Björkqvist et al. (*Thrombosis and Haemostasis*, 2013, 110, 399-407) demonstrated that aprotinin (a protein that inhibits serine proteases including plasma kallikrein) may be used to decrease postoperative bleeding.

Other complications of diabetes such as cerebral haemorrhage, nephropathy, cardiomyopathy and neuropathy, all of which have associations with plasma kallikrein may also be considered as targets for a plasma kallikrein inhibitor.

Synthetic and small molecule plasma kallikrein inhibitors have been described previously, for example by Garrett et al. ("Peptide aldehyde . . . ." *J. Peptide Res.* 52, p 62-71 (1998)), T. Griesbacher et al. ("Involvement of tissue kallikrein but not plasma kallikrein in the development of symptoms mediated by endogenous kinins in acute pancreatitis in rats" *British Journal of Pharmacology* 137, p 692-700 (2002)), Evans ("Selective dipeptide inhibitors of kallikrein" WO03/076458), Szelke et al. ("Kininogenase inhibitors" WO92/04371), D. M. Evans et al. (*Immunolpharmacology*, 32, p 115-116 (1996)), Szelke et al. ("Kininogen inhibitors" WO95/07921), Antonsson et al. ("New peptides derivatives" WO94/29335), J. Corte et al. ("Six membered heterocycles useful as serine protease inhibitors" WO2005/123680), J. Stürzbecher et al. (*Brazilian J. Med. Biol. Res* 27, p 1929-34 (1994)), Kettner et al. (U.S. Pat. No. 5,187,157), N. Teno et al. (*Chem. Pharm. Bull.* 41, p 1079-1090 (1993)), W. B. Young et al. ("Small molecule inhibitors of plasma kallikrein" *Bioorg. Med. Chem.* Letts. 16, p 2034-2036 (2006)), Okada et al. ("Development of potent and selective plasmin and plasma kallikrein inhibitors and studies on the structure-activity relationship" *Chem. Pharm. Bull.* 48, p 1964-72 (2000)), Steinmetzer et al. ("Trypsin-like serine protease inhibitors and their preparation and use" WO08/049595), Zhang et al. ("Discovery of highly potent small molecule kallikrein inhibitors" Medicinal Chemistry 2, p 545-553 (2006)), Sinha et al. ("Inhibitors of plasma kallikrein" WO08/016883), Shigenaga et al. ("Plasma Kallikrein Inhibitors" WO2011/118672), and Kolte et al. ("Biochemical characterization of a novel high-affinity and specific kallikrein inhibitor", British Journal of Pharmacology (2011), 162(7), 1639-1649). Also, Steinmetzer et al. ("Serine protease inhibitors" WO2012/004678) describes cyclized peptide analogs which are inhibitors of human plasmin and plasma kallikrein.

To date, no small molecule synthetic plasma kallikrein inhibitor has been approved for medical use. Many of the molecules described in the known art suffer from limitations such as poor selectivity over related enzymes such as KLK1, thrombin and other serine proteases, and poor oral availability. The large protein plasma kallikrein inhibitors present risks of anaphylactic reactions, as has been reported for Ecallantide. Thus there remains a need for compounds that selectively inhibit plasma kallikrein, that do not induce anaphylaxis and that are orally available. Furthermore, the vast majority of molecules in the known art feature a highly polar and ionisable guanidine or amidine functionality. It is well known that such functionalities may be limiting to gut permeability and therefore to oral availability. For example, it has been reported by Tamie J. Chilcote and Sukanto Sinha ("ASP-634: An Oral Drug Candidate for Diabetic MacularEdema", ARVO 2012 May 6-May 9, 2012, Fort Lauderdale, Fla., Presentation 2240) that ASP-440, a benzamidine, suffers from poor oral availability. It is further reported that absorption may be improved by creating a prodrug such as ASP-634. However, it is well known that prodrugs can suffer from several drawbacks, for example, poor chemical stability and potential toxicity from the inert carrier or from unexpected metabolites. In another report, indole amides are claimed as compounds that might overcome problems associated with drugs possessing poor or inadequate ADME-tox and physicochemical properties although no inhibition against plasma kallikrein is presented or claimed (Griffioen et al, "Indole amide derivatives and related compounds for use in the treatment of neurodegenerative diseases", WO2010/142801).

BioCryst Pharmaceuticals Inc. have reported the discovery of the orally available plasma kallikrein inhibitor BCX4161 ("BCX4161, An Oral Kallikrein Inhibitor: Safety and Pharmacokinetic Results Of a Phase 1 Study In Healthy Volunteers", Journal of Allergy and Clinical Immunology, Volume 133, Issue 2, Supplement, February 2014, page AB39 and "A Simple, Sensitive and Selective Fluorogenic Assay to Monitor Plasma Kallikrein Inhibitory Activity of BCX4161 in Activated Plasma", Journal of Allergy and Clinical Immunology, Volume 133, Issue 2, Supplement February 2014, page AB40). However, human doses are relatively large, currently being tested in proof of concept studies at doses of 400 mg three times daily.

There are only few reports of plasma kallikrein inhibitors that do not feature guanidine or amidine functionalities. One example is Brandl et al. ("N-((6-amino-pyridin-3-yl) methyl)-heteroaryl-carboxamides as inhibitors of plasma kallikrein" WO2012/017020), which describes compounds that feature an aminopyridine functionality. Oral efficacy in a rat model is demonstrated at relatively high doses of 30 mg/kg and 100 mg/kg but the pharmacokinetic profile is not reported. Thus it is not yet known whether such compounds will provide sufficient oral availability or efficacy for progression to the clinic. Other examples are Brandl et al.

("Aminopyridine derivatives as plasma kallikrein inhibitors" WO2013/111107) and Flohr et al. ("5-membered heteroarylcarboxamide derivatives as plasma kallikrein inhibitors" WO2013/111108). However, neither of these documents report any in vivo data and therefore it is not yet known whether such compounds will provide sufficient oral availability or efficacy for progression to the clinic. Another example is Allan et al. "Benzylamine derivatives" WO2014/108679.

In the manufacture of pharmaceutical formulations, it is important that the active compound be in a form in which it can be conveniently handled and processed in order to obtain a commercially viable manufacturing process. Accordingly, the chemical stability and the physical stability of the active compound are important factors. The active compound, and formulations containing it, must be capable of being effectively stored over appreciable periods of time, without exhibiting any significant change in the physico-chemical characteristics (e.g. chemical composition, density, hygroscopicity and solubility) of the active compound.

It is known that manufacturing a particular solid-state form of a pharmaceutical ingredient can affect many aspects of its solid state properties and offer advantages in aspects of solubility, dissolution rate, chemical stability, mechanical properties, technical feasibility, processability, pharmacokinetics and bioavailability. Some of these are described in "Handbook of Pharmaceutical Salts; Properties, Selection and Use", P. Heinrich Stahl, Camille G. Wermuth (Eds.) (Verlag Helvetica Chimica Acta, Zurich). Methods of manufacturing solid-state forms are also described in "Practical Process Research and Development", Neal G. Anderson (Academic Press, San Diego) and "Polymorphism: In the Pharmaceutical Industry", Rolf Hilfiker (Ed) (Wiley VCH). Polymorphism in pharmaceutical crystals is described in Byrn (Byrn, S. R., Pfeiffer, R. R., Stowell, J. G., "Solid-State Chemistry of Drugs", SSCI Inc., West Lafayette, Ind., 1999), Brittain, H. G., "Polymorphism in Pharmaceutical Solids", Marcel Dekker, Inc., New York, Basel, 1999) or Bernstein (Bernstein, J., "Polymorphism in Molecular Crystals", Oxford University Press, 2002).

The applicant has developed a novel series of compounds that are inhibitors of plasma kallikrein, which are disclosed in WO2016/083820 (PCT/GB2015/053615). These compounds demonstrate good selectivity for plasma kallikrein and are potentially useful in the treatment of diabetic retinopathy, macular edema and hereditary angioedema. One such compound is N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide. Initial attempts to prepare N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide were performed by evaporation of the 1% ammonia-methanol/DCM solvent used during chromatography to yield a foam with XRPD data (recorded using Method B) that shows mainly amorphous content consistent with the solid form referred to herein as 'Form A' (FIG. 1a). The applicant has now developed novel crystalline forms of this compound, which are herein referred to as 'Form 1', 'Form 2', 'Form 3' and 'Form 4'. The novel solid forms have advantageous physico-chemical properties that render them suitable for development.

The applicant has also developed novel crystalline salt forms of N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide, specifically novel crystalline hydrochloride, sulfate, phosphate, mesylate, tosylate, edisylate and besylate salts of N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide. The novel solid forms have advantageous physico-chemical properties that render them suitable for development, in particular, they have a low hygroscopicity and their preparation by crystallisation is simple and scalable.

DESCRIPTION OF THE INVENTION

Thus, in accordance with an aspect of the present invention, there is provided crystalline polymorphs of N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide. In the present application these polymorphs may be referred to as 'Form 1', 'Form 2', 'Form 3' and 'Form 4'.

The crystalline polymorphs of the present invention have advantageous physico-chemical properties that render them suitable for development. For example, Gravimetric Vapour Sorption (GVS) data of 'Form 1' of N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide, FIG. 5, under normal conditions (for example, up to 70% relative humidity) there is only a relatively gradual increase in water content. This is consistent with the absence of significant hygroscopicity. In contrast, amorphous materials are typically significantly hygroscopic, or even deliquescent, often rendering the material into an unworkable gum. Furthermore, the absence of weight loss before melt of the sample of Form 1 (see STA data, FIG. 3) indicates that Form 1 is not hydrated or solvated. Stable hydrates may be unsuitable for pharmaceutical development because they may induce an undesirable transformation of the administered anhydrous form of the drug once the drug meets the aqueous environment of the human body. Another advantage of the crystalline polymorphs is that they are more easily processable. That is, their preparation by crystallisation (see Examples) is a common and easily scalable procedure to remove undesirable impurities.

Figure 46:
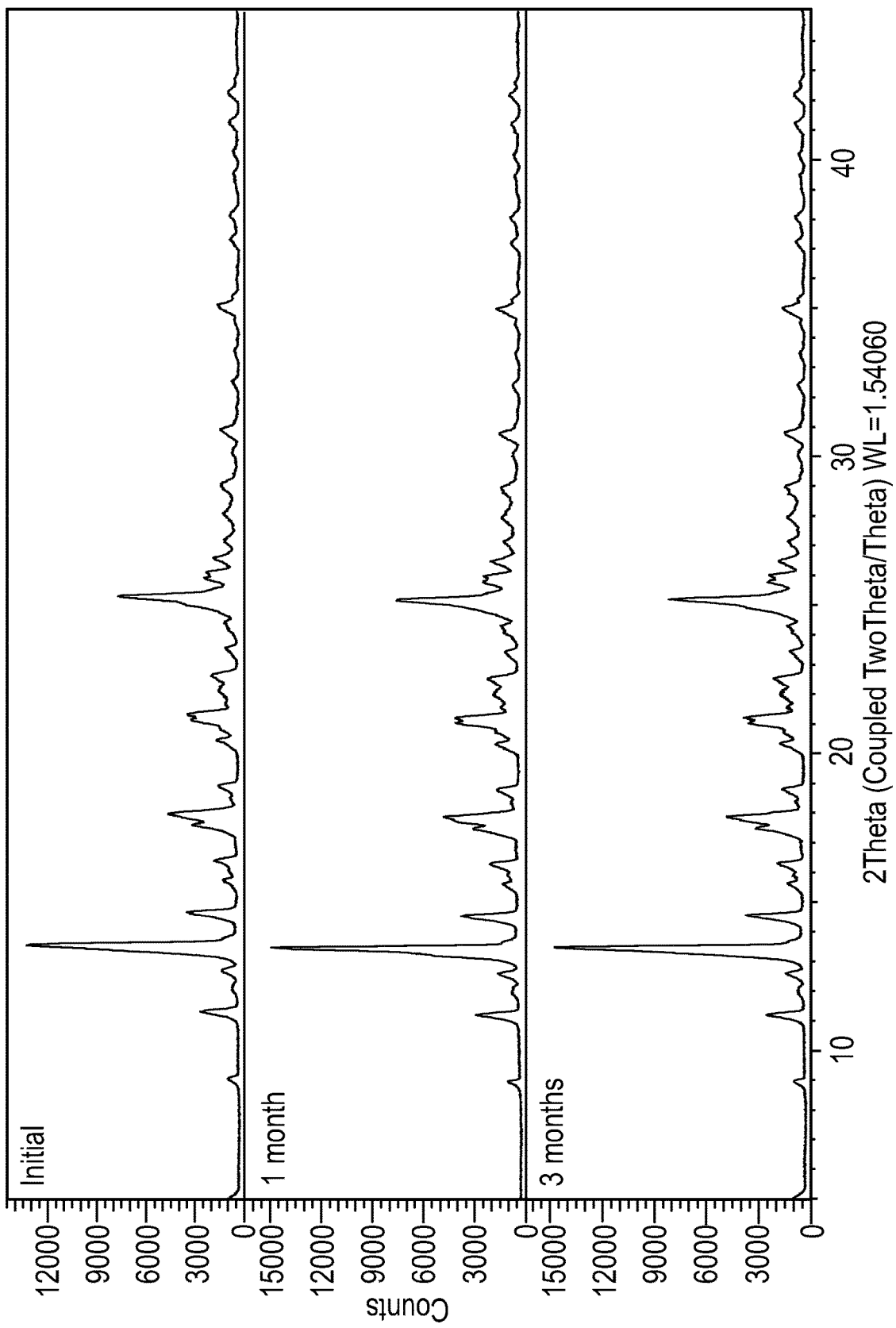
Figure 47:
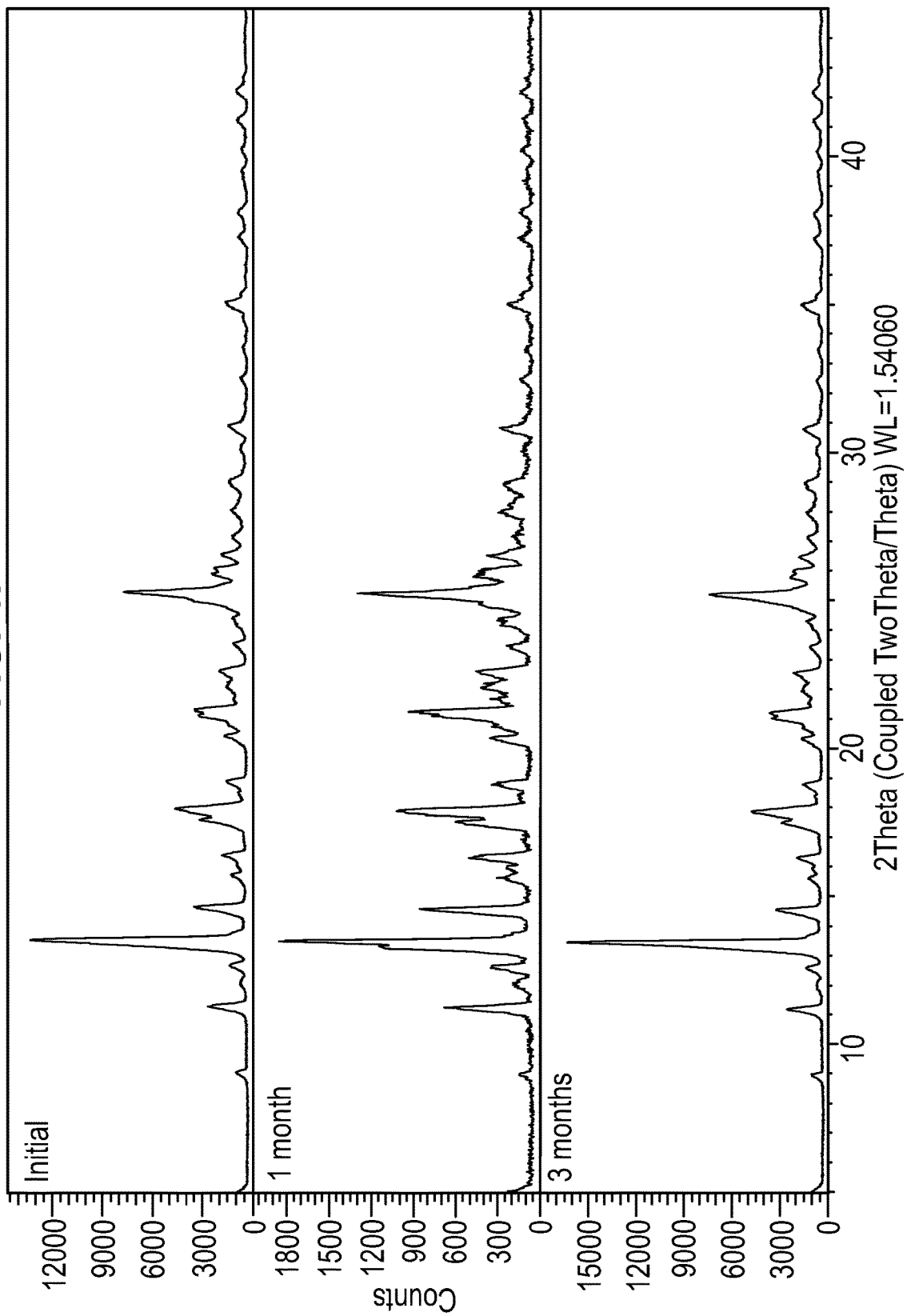

Further evidence of the suitability of the crystalline forms of N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide for pharmaceutical development is provided by the stability data disclosed herein. Two samples of Form 1 of N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide were stored at 25° C./60% RH and 40° C./75% RH packed in double polyethylene bags and sealed in a HDPE bottle. At the initial timepoint, XRPD showed the sample to be crystalline and consistent with the Form 1 polymorph. Under the storage conditions of 25° C./60% RH and 40° C./75% RH, XRPD showed no change after 1 month and after 3 months (FIGS. 46 and 47).

The solubility of the free base in water of N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide was relatively low (<0.5 mg/mL), and therefore salts of N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide were investigated.

In a further aspect of the present invention, there is provided crystalline polymorphs of N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide salts, specifically crystalline polymorphs of N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide hydrochloride; N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide sulfate; N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide phosphate; N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide mesylate; N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide tosylate; N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide edisylate; and N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide besylate.

Furthermore, the present invention provides specific crystalline polymorphs of N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide hydrochloride which are herein referred to as 'Form 5', 'Form 6', 'Form 7', and 'Form 18'.

Furthermore, the present invention provides a specific crystalline polymorph of N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide sulfate which is herein referred to as 'Form 8'.

Furthermore, the present invention provides specific crystalline polymorphs of N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide phosphate which are herein referred to as 'Form 9', 'Form 10', and 'Form 11'.

Furthermore, the present invention provides specific crystalline polymorphs of N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide mesylate which are herein referred to as 'Form 12', and 'Form 13'.

Furthermore, the present invention provides a specific crystalline polymorph of N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide tosylate which is herein referred to as 'Form 14'.

Furthermore, the present invention provides specific crystalline polymorphs of N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide edisylate which are herein referred to as 'Form 15', and 'Form 16'.

Furthermore, the present invention provides a specific crystalline polymorph of N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide besylate which is herein referred to as 'Form 17'.

The novel crystalline salts of the present invention have advantageous physico-chemical properties that render them suitable for development. For example Form 8 of N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide sulfate shows excellent aqueous solubility, and can be reproducibly scaled-up. For example, Gravimetric Vapour Sorption (GVS) data of Form 8 of N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide sulfate, FIG. 33, under normal conditions (for example, up to 70% relative humidity), show that there is only a relatively gradual increase in water content and that the hydration is reversible. This is consistent with the absence of significant hygroscopicity. Furthermore, the sulfate salt of N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide shows a low tendency for polymorphism, as demonstrated by the single polymorph that was identified during the polymorph screens disclosed herein.

The name N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide denotes the structure depicted in Formula A.

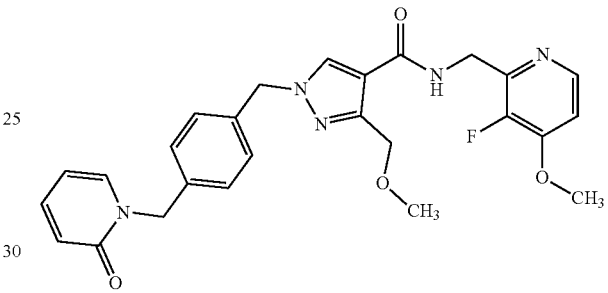

Formula A

Four crystalline polymorphs of N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide have been isolated and characterised to date, which are herein referred to as 'Form 1', 'Form 2', 'Form 3', and 'Form 4'. Preferably, the crystalline form is Form 1.

Four crystalline polymorphs of N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide hydrochloride have been isolated and characterised to date, which are herein referred to as 'Form 5', 'Form 6', 'Form 7', and 'Form 18'.

One crystalline polymorph of N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide sulfate have been isolated and characterised to date, which is herein referred to as 'Form 8'.

The term "sulfate" as used herein when referring to a salt of N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide is intended to encompass both a mono-sulfate salt and a hemi-sulfate salt. In one embodiment, Form 8 of N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide is a mono-sulfate salt. In an alternative embodiment, Form 8 of N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide is a hemi-sulfate salt.

Three crystalline polymorphs of N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide phosphate have been isolated and characterised to date, which are herein referred to as 'Form 9', 'Form 10', and 'Form 11'.

The term "phosphate" as used herein when referring to a salt of N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide is intended to encompass both a mono-phosphate salt and a hemi-phosphate salt. In one embodiment, Forms 9, 10 and 11 of N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide are each independently a mono-phosphate salt. In an alternative embodiment, Forms 9, 10 and 11 of N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide are each independently a hemi-phosphate salt.

Two crystalline polymorphs of N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide mesylate have been isolated and characterised to date, which are herein referred to as 'Form 12', and 'Form 13'.

One crystalline polymorph of N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide tosylate has been isolated and characterised to date, which is herein referred to as 'Form 14'.

Two crystalline polymorphs of N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide edisylate have been isolated and characterised to date, which are herein referred to as 'Form 15', and 'Form 16'.

The term "edisylate" as used herein when referring to a salt of N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide is intended to encompass both a mono-edisylate salt and a hemi-edisylate salt. In one embodiment, Forms 15 and 16 of N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide are each independently a mono-edisylate salt. In an alternative embodiment, Forms 15 and 16 of N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide are each independently a hemi-edisylate salt. Preferably, Forms 15 and 16 of N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide are each independently a mono-edisylate salt.

One crystalline polymorph of N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide besylate has been isolated and characterised to date, which is herein referred to as 'Form 17'.

The present invention encompasses solvates (e.g. hydrates) of the crystalline forms of N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide and salts thereof described herein.

In an aspect of the invention, Form 1 of N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide is not a solvate or a hydrate.

In an aspect of the invention, Form 18 of N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide hydrochloride is a solvate or a hydrate, preferably a hydrate, more preferably a hemi-hydrate, monohydrate or dihydrate, most preferably a dihydrate.

In an aspect of the invention, Form 8 of N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide sulfate is a solvate or a hydrate, preferably a hydrate, more preferably a hemi-hydrate, monohydrate or dihydrate, most preferably a hemi-hydrate.

In an aspect of the invention, Form 15 of N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide edisylate is a solvate or a hydrate, preferably a hydrate, more preferably a hemi-hydrate, monohydrate or dihydrate.

In an aspect of the invention, Form 16 of N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide edisylate is a solvate or a hydrate, preferably a hydrate, more preferably a hemi-hydrate, monohydrate or dihydrate.

In the present specification, X-ray powder diffraction peaks (expressed in degrees 2θ) are measured using Cu Kα radiation.

The present invention provides a crystalline form (Form 1) of N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide, which exhibits at least the following characteristic X-ray powder diffraction peaks (Cu Kα radiation, expressed in degrees 2θ) at approximately:

(1) 11.2, 12.5, 13.2, 14.5 and 16.3; or
(2) 11.2, 12.5, 13.2, 14.5, 16.3, 17.4 and 17.9; or
(3) 11.2, 12.5, 13.2, 14.5, 16.3, 17.4, 17.9, 21.2 and 22.0.

The term "approximately" means in this context that there is an uncertainty in the measurements of the degrees 2θ of ±0.3 (expressed in degrees 2θ), preferably ±0.2 (expressed in degrees 2θ).

The present invention also provides a crystalline form (Form 1) of N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide, having an X ray powder diffraction pattern comprising characteristic peaks (expressed in degrees 2θ) at approximately 4.4, 11.2, 12.5, 13.2, 14.5, 16.3, 17.4, 17.9, 21.2, 22.0 and 22.6.

Figure 2A:
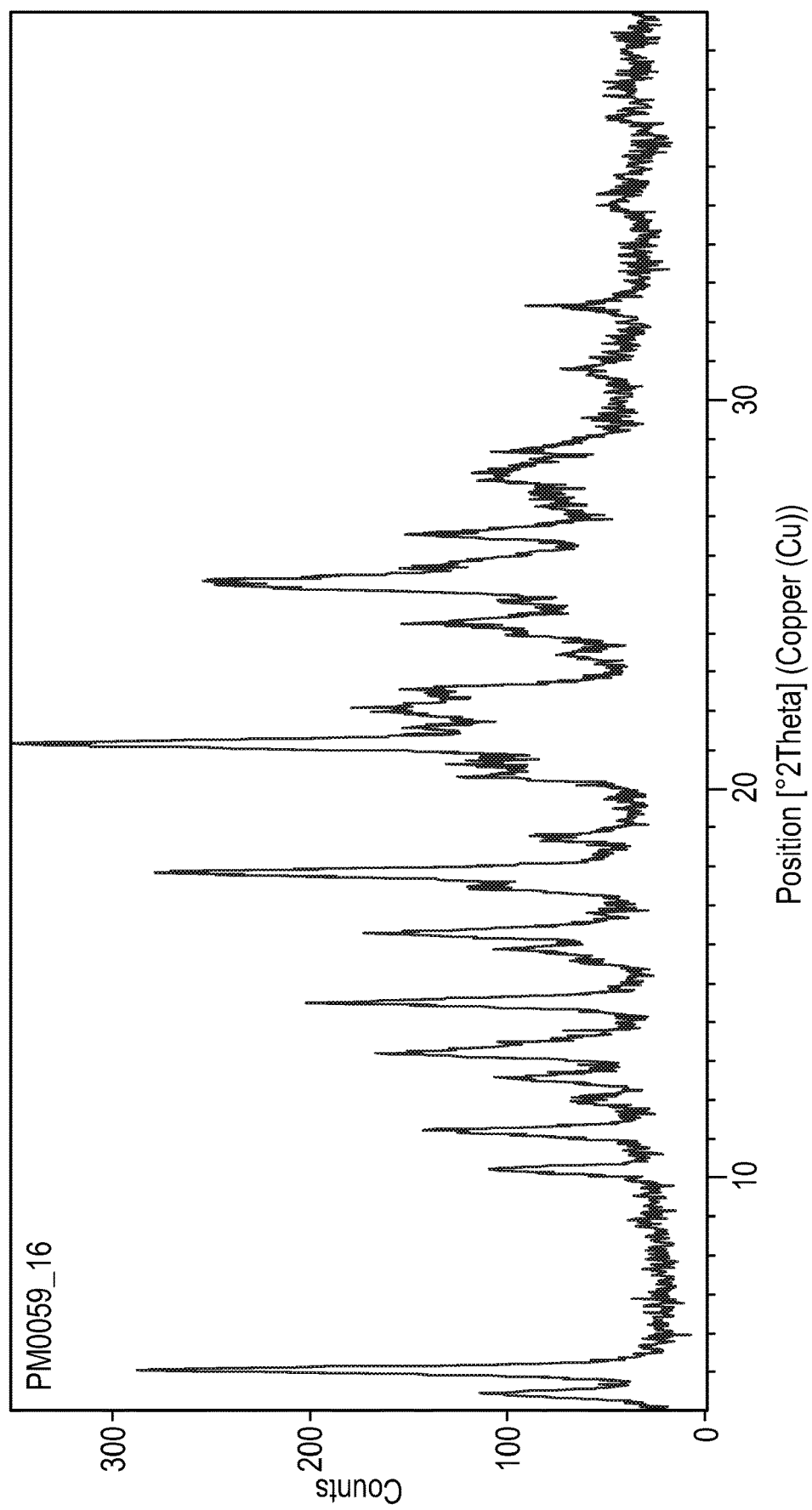

The present invention also provides a crystalline form (Form 1) of N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide having an X-ray powder diffraction pattern substantially the same as that shown in FIG. 2a.

The X-ray powder diffraction pattern of a polymorphic form may be described herein as "substantially" the same as that depicted in a Figure. It will be appreciated that the peaks in X-ray powder diffraction patterns may be slightly shifted in their positions and relative intensities due to various factors known to the skilled person. For example, shifts in peak positions or the relative intensities of the peaks of a pattern can occur because of the equipment used, method of sample preparation, preferred packing and orientations, the radiation source, and method and length of data collection. However, the skilled person will be able to compare the X-ray powder diffraction patterns shown in the figures herein with those of an unknown polymorph to confirm the identity of the polymorph.

Figure 7:
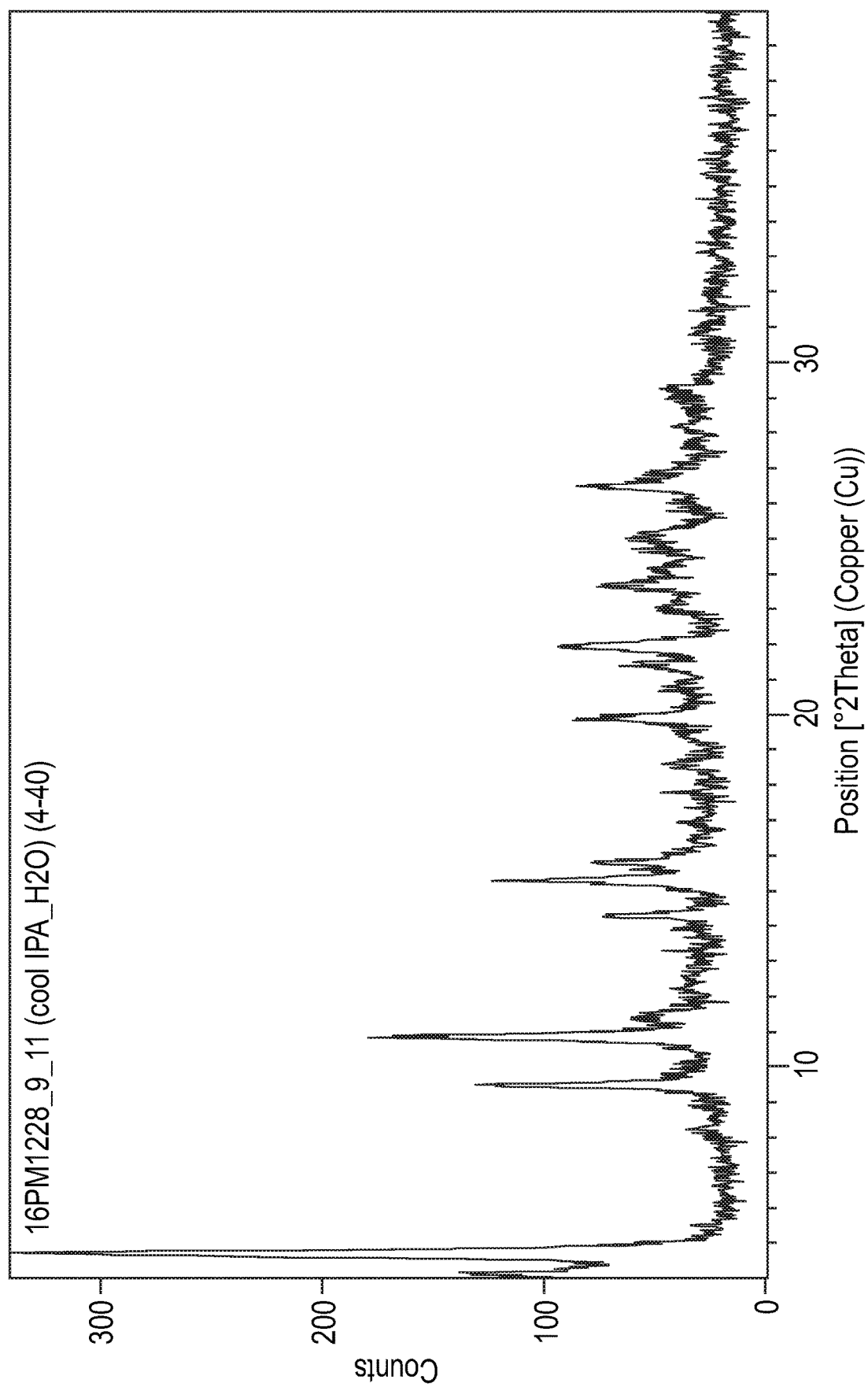

The present invention also provides a crystalline form (Form 2) of N-[(3-fluoro-4-methoxypyridin-2-yl)methyl]-3-(methoxymethyl)-1-({4-[(2-oxopyridin-1-yl)methyl]

phenyl}methyl)pyrazole-4-carboxamide having an X-ray powder diffraction pattern substantially the same as that shown in FIG. 7.

Figure 8:
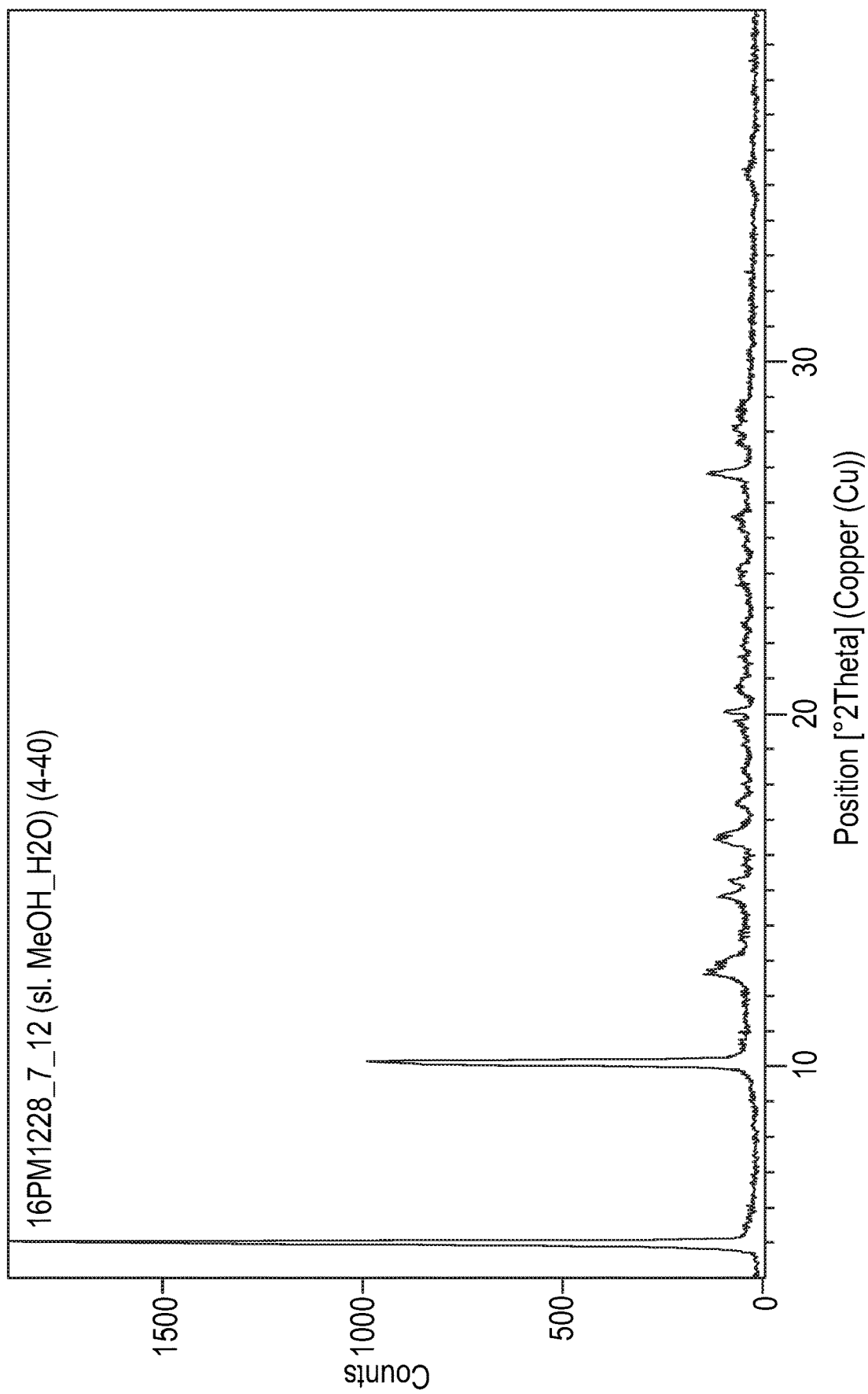

The present invention also provides a crystalline form (Form 3) of N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide having an X-ray powder diffraction pattern substantially the same as that shown in FIG. 8.

Figure 9:
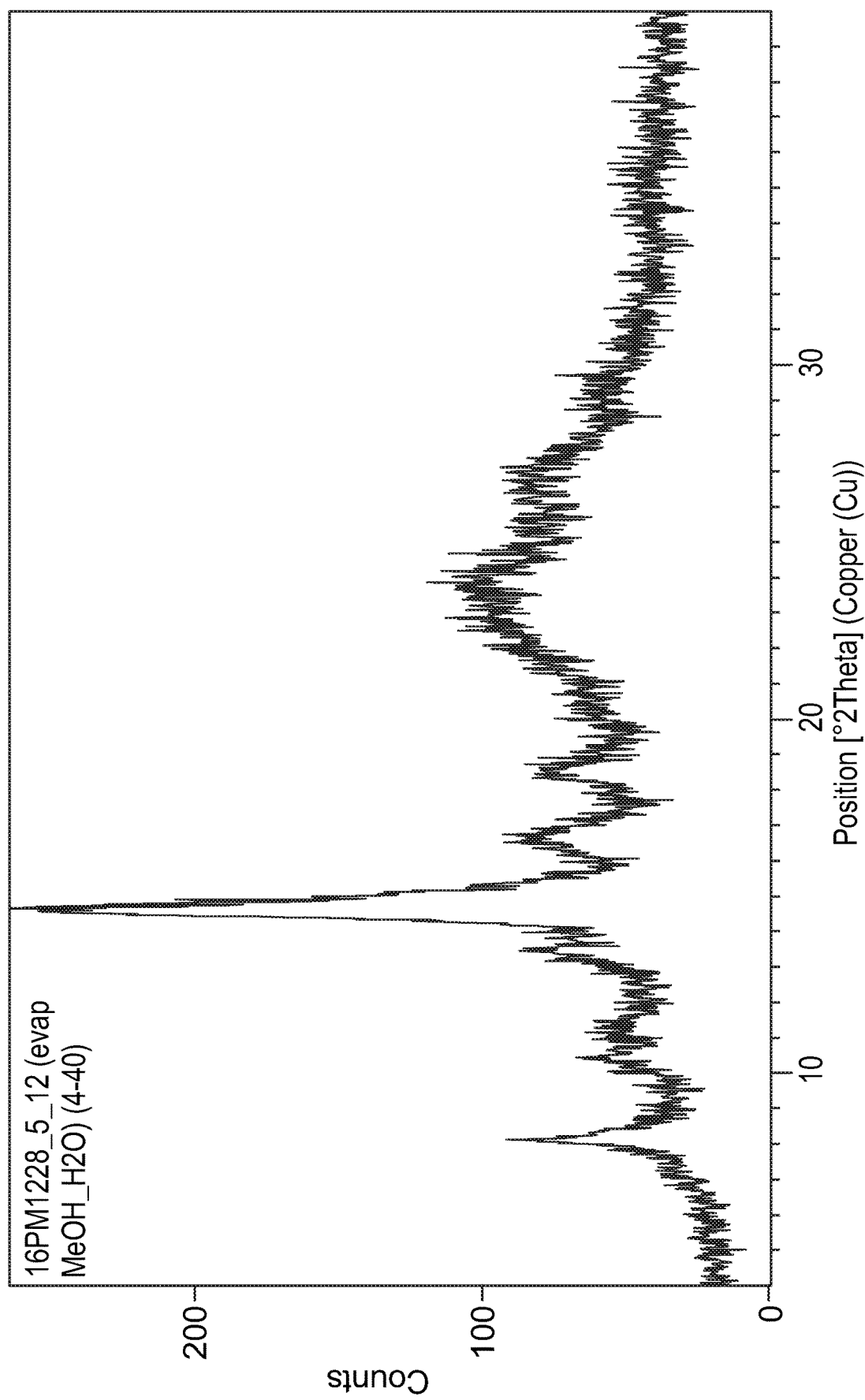

The present invention also provides a crystalline form (Form 4) of N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide having an X-ray powder diffraction pattern substantially the same as that shown in FIG. 9.

Figure 10:
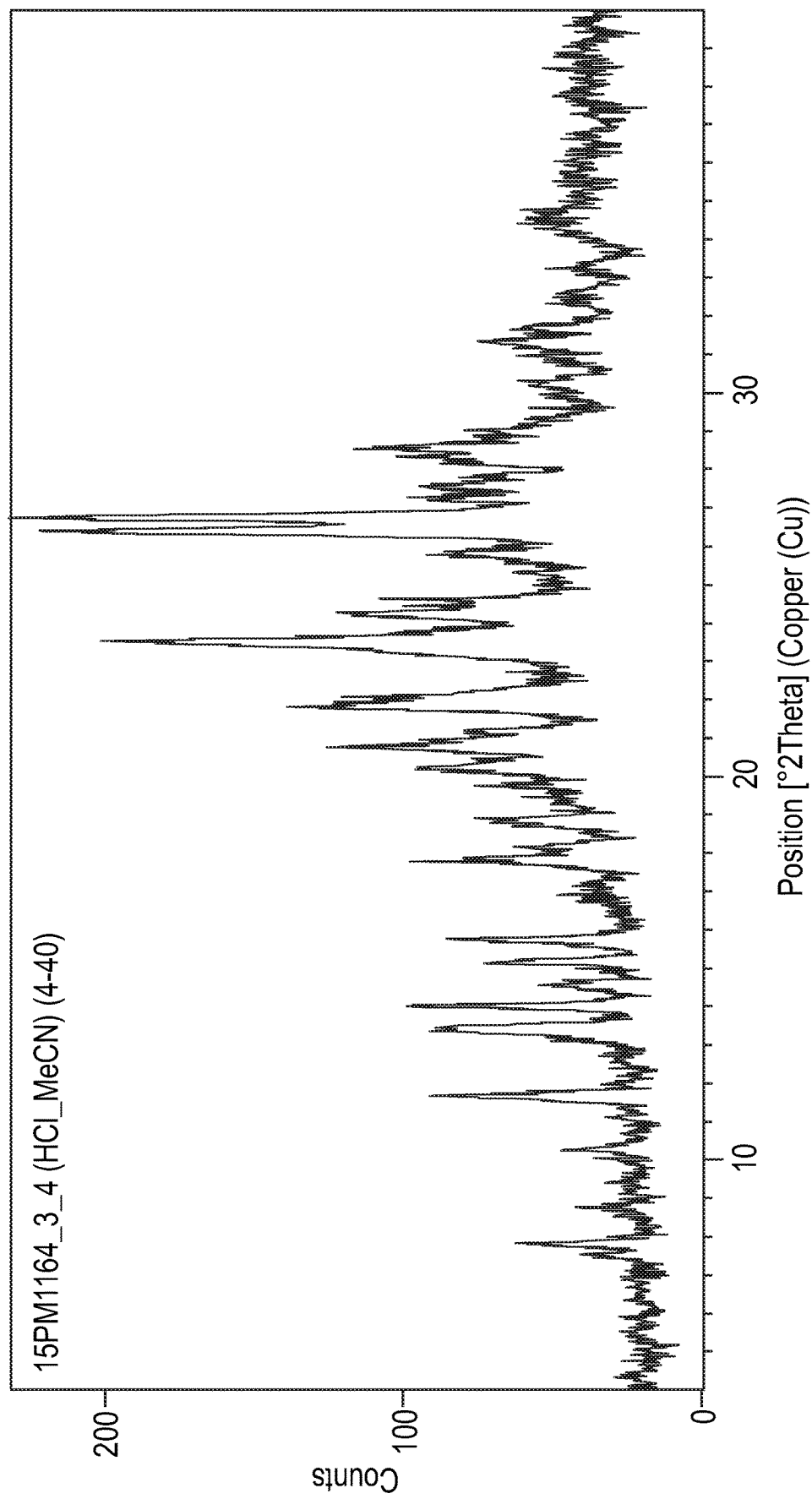

The present invention also provides a crystalline form (Form 5) of N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide hydrochloride having an X-ray powder diffraction pattern substantially the same as that shown in FIG. 10.

Figure 11:
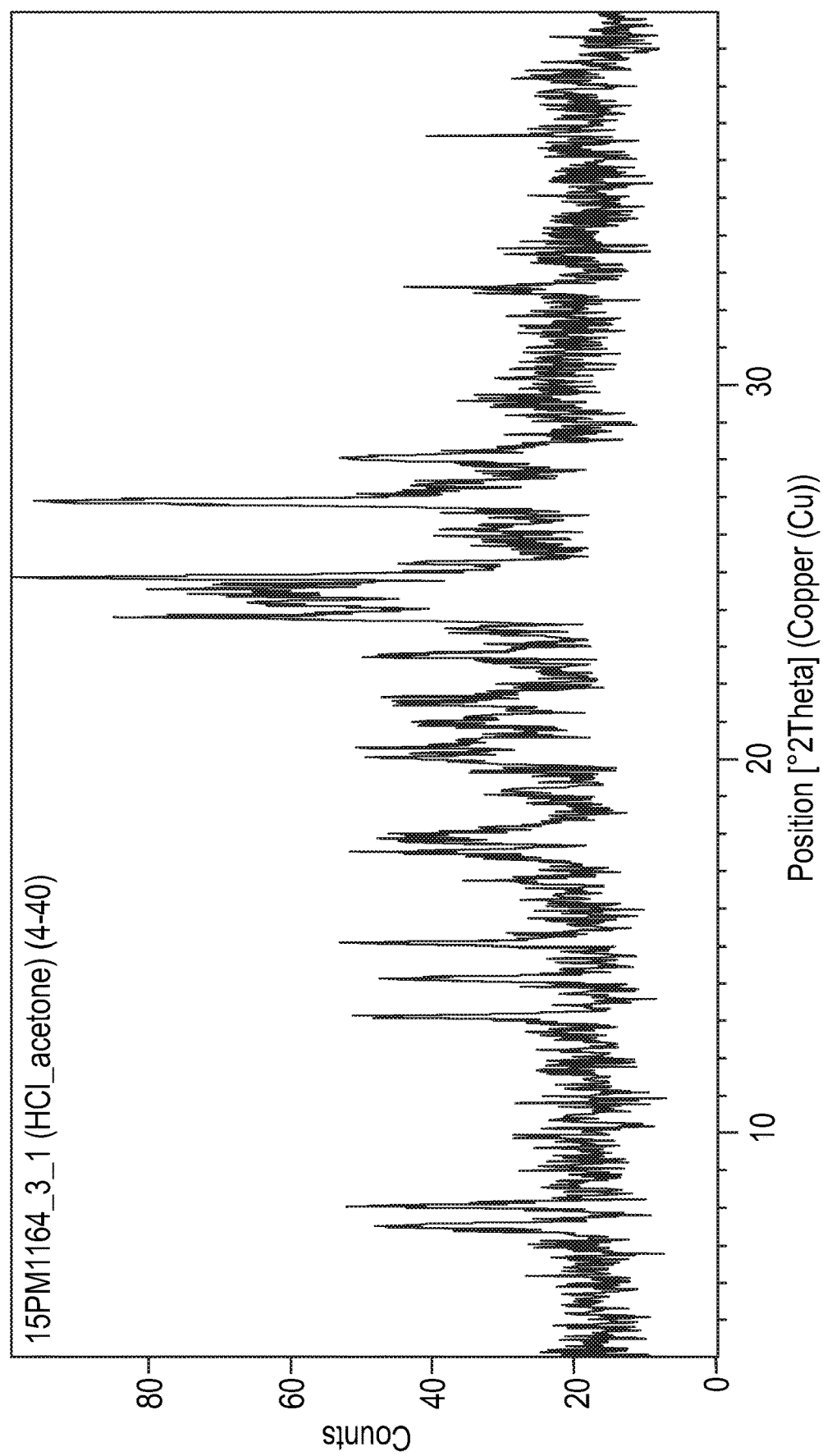

The present invention also provides a crystalline form (Form 6) of N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide hydrochloride having an X-ray powder diffraction pattern substantially the same as that shown in FIG. 11.

Figure 12:
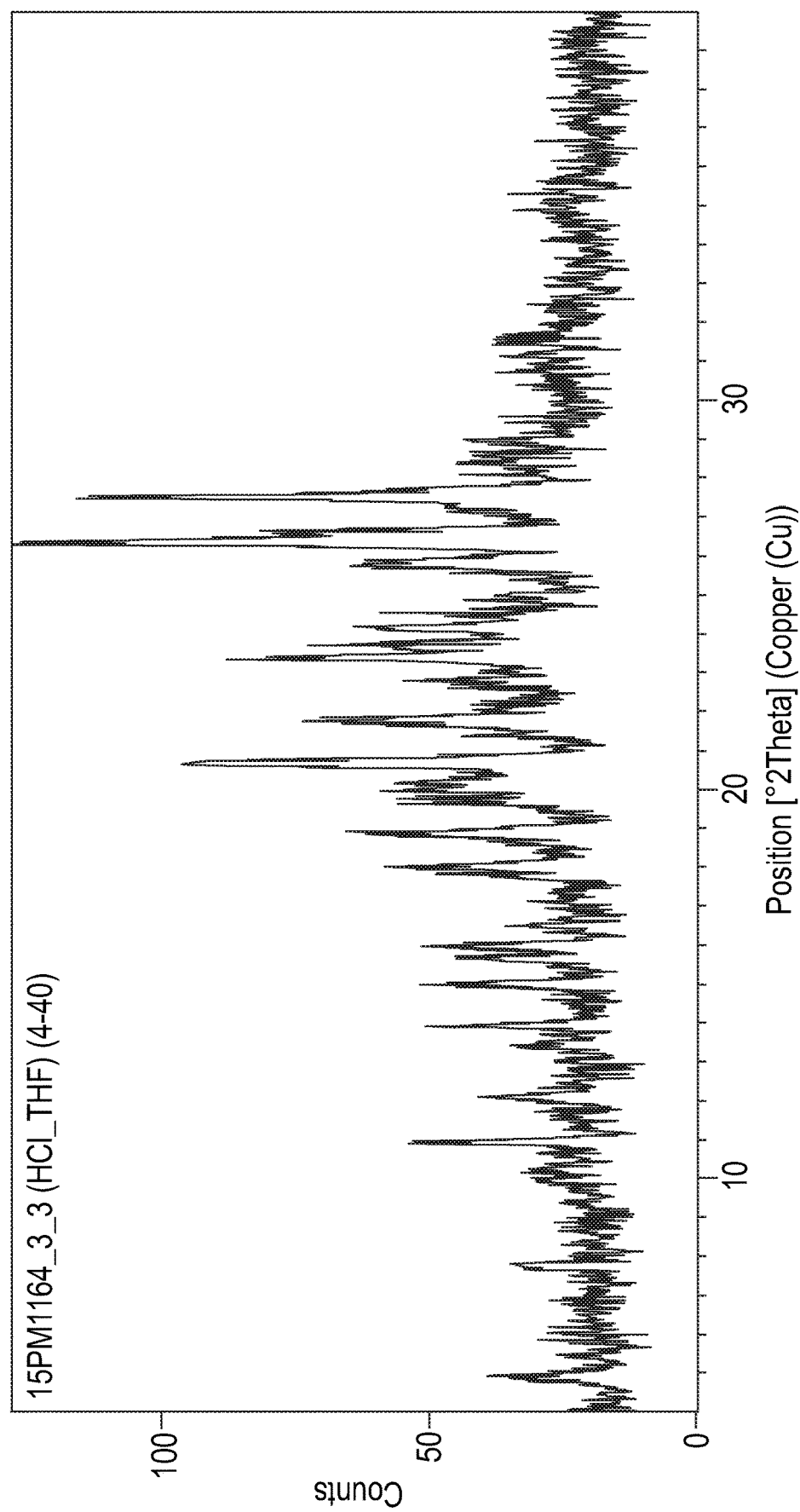

The present invention also provides a crystalline form (Form 7) of N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide hydrochloride having an X-ray powder diffraction pattern substantially the same as that shown in FIG. 12.

The present invention also provides a crystalline form (Form 8) of N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide sulfate, which exhibits at least the following characteristic X-ray powder diffraction peaks (Cu Kα radiation, expressed in degrees 2θ) at approximately:
(1) 5.1, 7.5, 12.0, 15.2, and 17.9; or
(2) 5.1, 7.5, 12.0, 15.2, 17.9, 20.1 and 22.8; or
(3) 5.1, 7.5, 12.0, 15.2, 17.9, 20.1, 22.8, 24.4 and 25.8.

The present invention also provides a crystalline form (Form 8) of N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide sulfate, having an X ray powder diffraction pattern comprising characteristic peaks (expressed in degrees 2θ) at approximately 5.1, 7.5, 12.0, 13.2, 15.2, 17.9, 18.2, 19.3, 20.1, 22.3, 22.8, 24.4 and 25.8. The present invention also provides a crystalline form (Form 8) of N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide sulfate having an X-ray powder diffraction pattern substantially the same as that shown in FIG. 13 or FIG. 30 (top).

The present invention also provides a crystalline form (Form 9) of N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide phosphate, which exhibits at least the following characteristic X-ray powder diffraction peaks (Cu Kα radiation, expressed in degrees 2θ) at approximately:
(1) 4.5, 13.4, 16.3, 17.3 and 18.9; or
(2) 4.5, 13.4, 16.3, 17.3, 17.8, 18.9 and 19.3; or
(3) 4.5, 13.4, 16.3, 17.3, 17.8, 18.9, 19.3, 20.5 and 23.0.

The present invention also provides a crystalline form (Form 9) of N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide phosphate, having an X ray powder diffraction pattern comprising characteristic peaks (expressed in degrees 2θ) at approximately 4.5, 7.2, 10.1, 13.4, 16.3, 17.3, 17.8, 18.9, 19.3, 20.5, 21.2, 23.0, 25.4 and 27.2.

Figure 14:
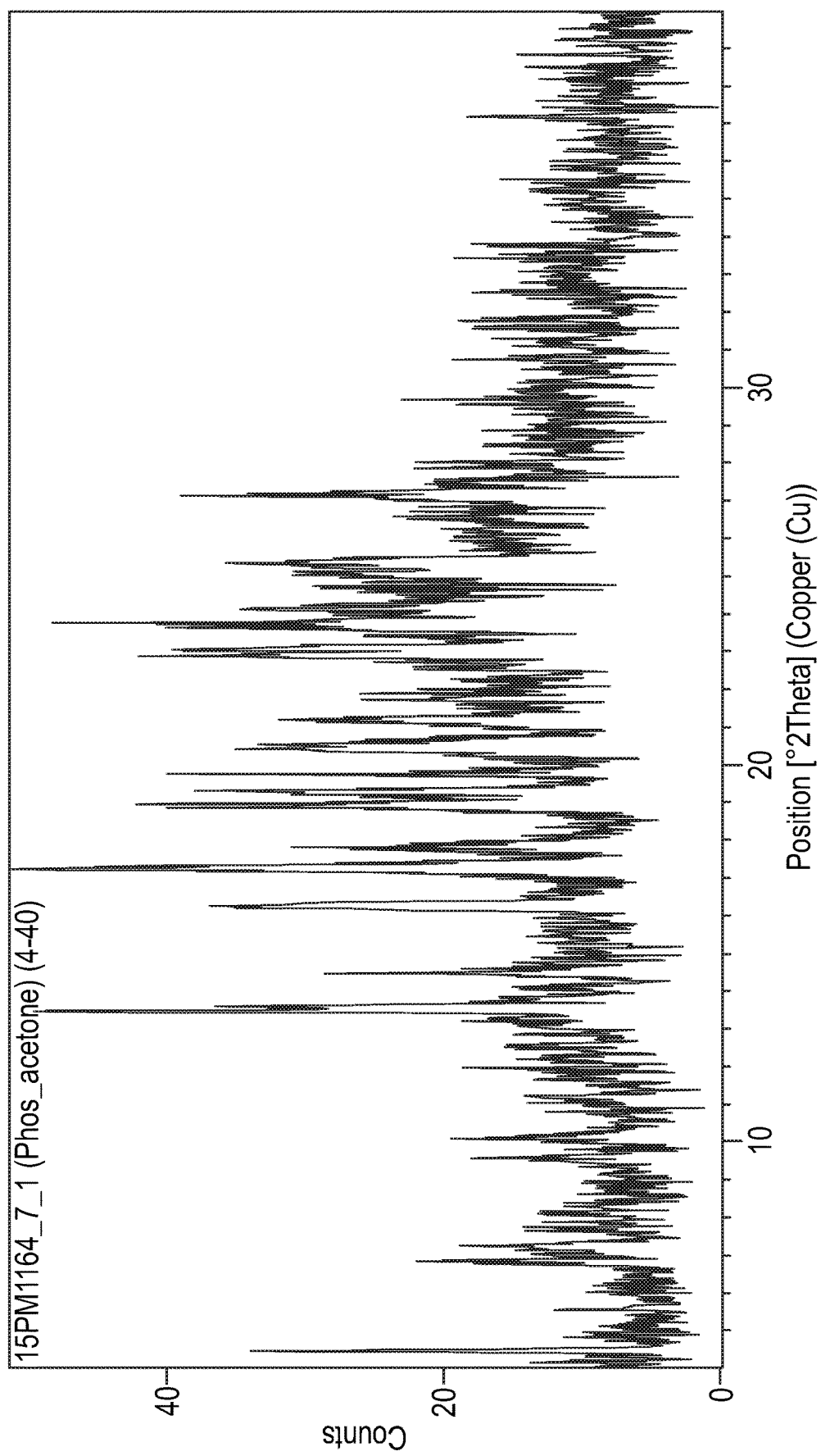

The present invention also provides a crystalline form (Form 9) of N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide phosphate having an X-ray powder diffraction pattern substantially the same as that shown in FIG. 14.

Figure 15:
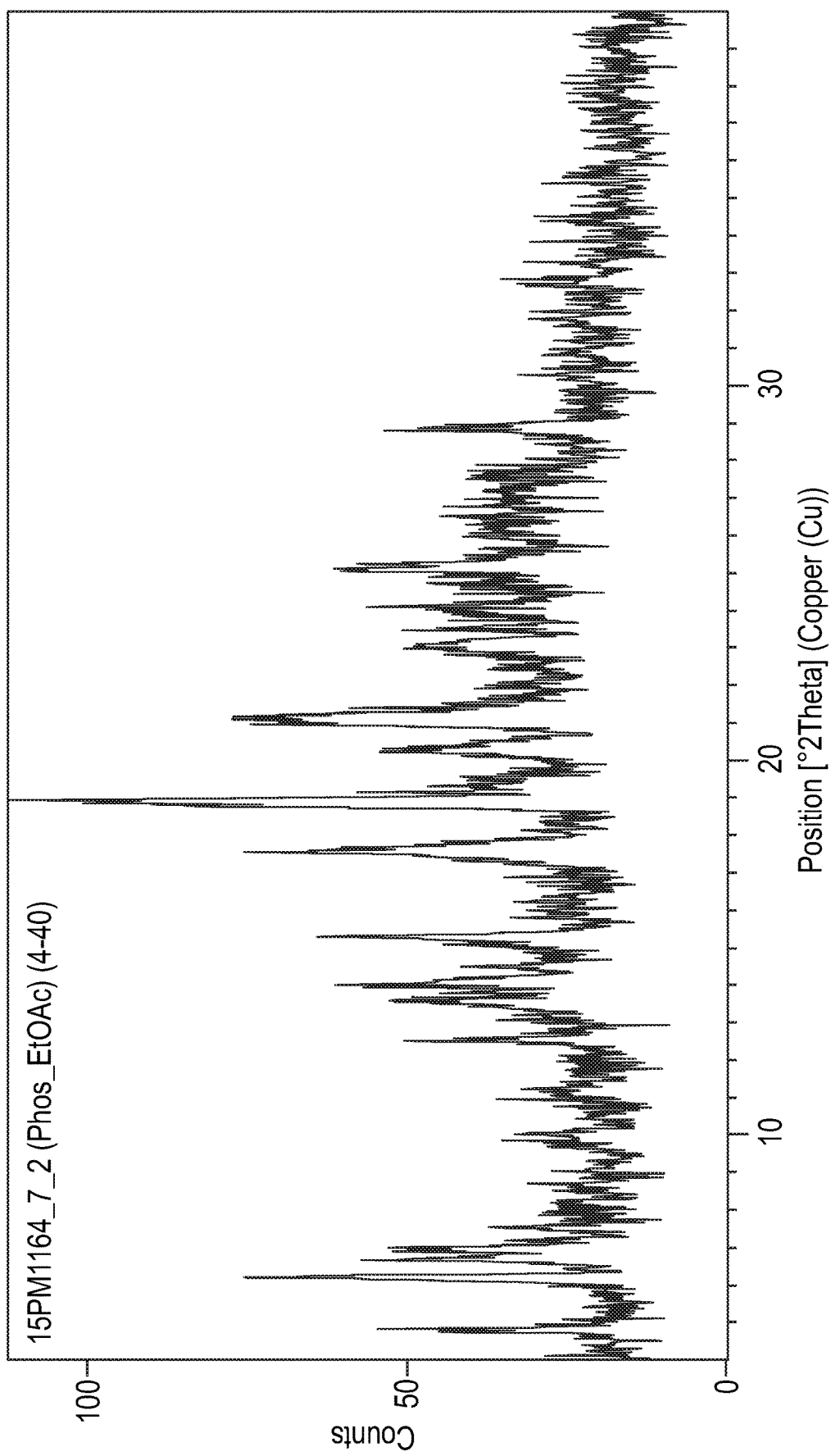

The present invention also provides a crystalline form (Form 10) of N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide phosphate having an X-ray powder diffraction pattern substantially the same as that shown in FIG. 15.

Figure 16:
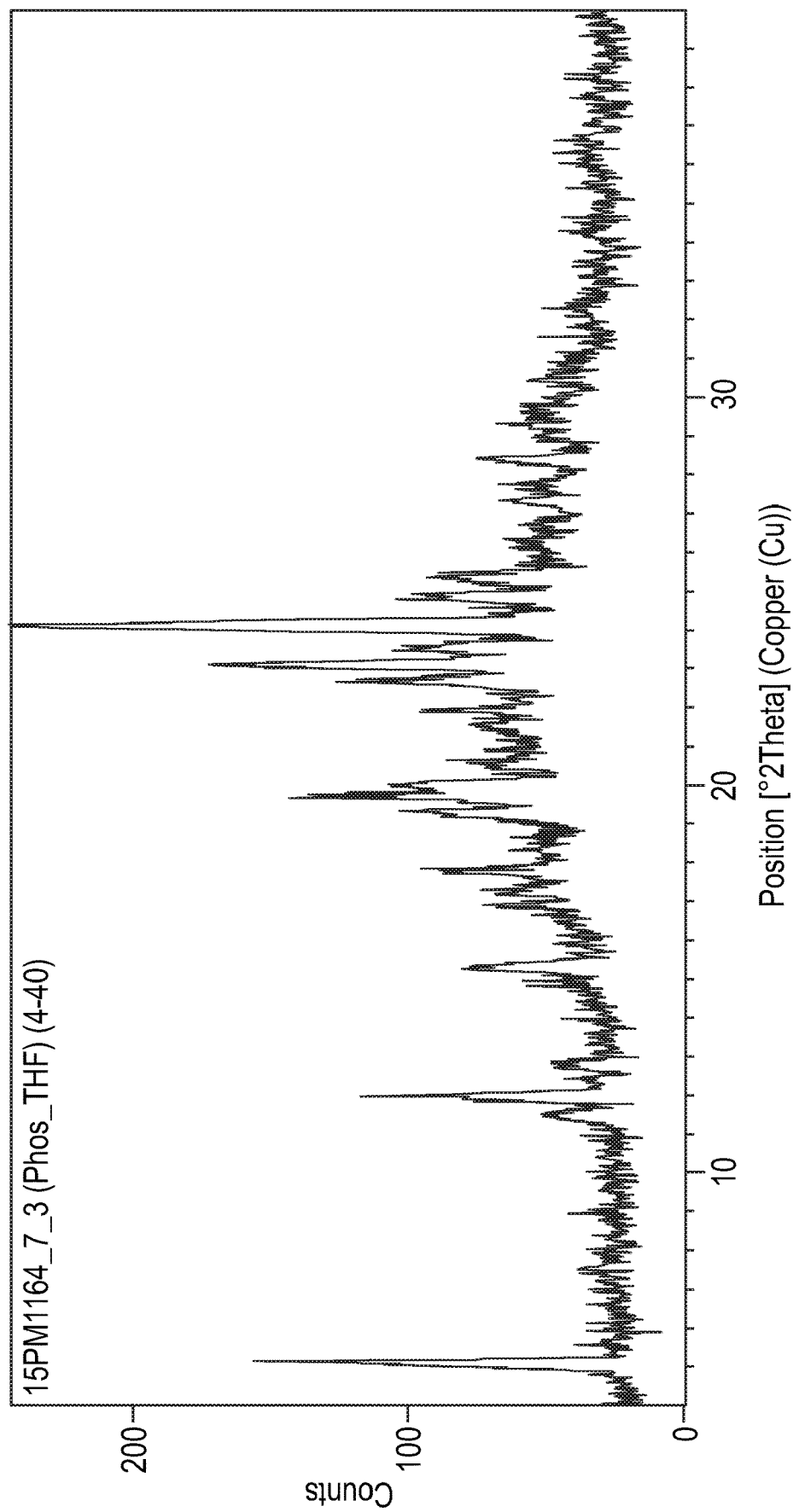

The present invention also provides a crystalline form (Form 11) of N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide phosphate having an X-ray powder diffraction pattern substantially the same as that shown in FIG. 16.

The present invention also provides a crystalline form (Form 12) of N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide mesylate, which exhibits at least the following characteristic X-ray powder diffraction peaks (Cu Kα radiation, expressed in degrees 2θ) at approximately:
(1) 5.0, 10.0, 14.8, 16.4 and 23.3; or
(2) 5.0, 10.0, 14.8, 16.4, 19.2, 20.3 and 23.3; or
(3) 5.0, 10.0, 14.8, 16.4, 19.2, 20.3, 21.5, 23.3, and 26.2.

The present invention also provides a crystalline form (Form 12) of N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide mesylate, having an X ray powder diffraction pattern comprising characteristic peaks (expressed in degrees 2θ) at approximately 5.0, 10.0, 13.8, 14.8, 16.4, 19.2, 20.3, 21.5, 23.3, 24.0, 26.2 and 27.6.

Figure 17:
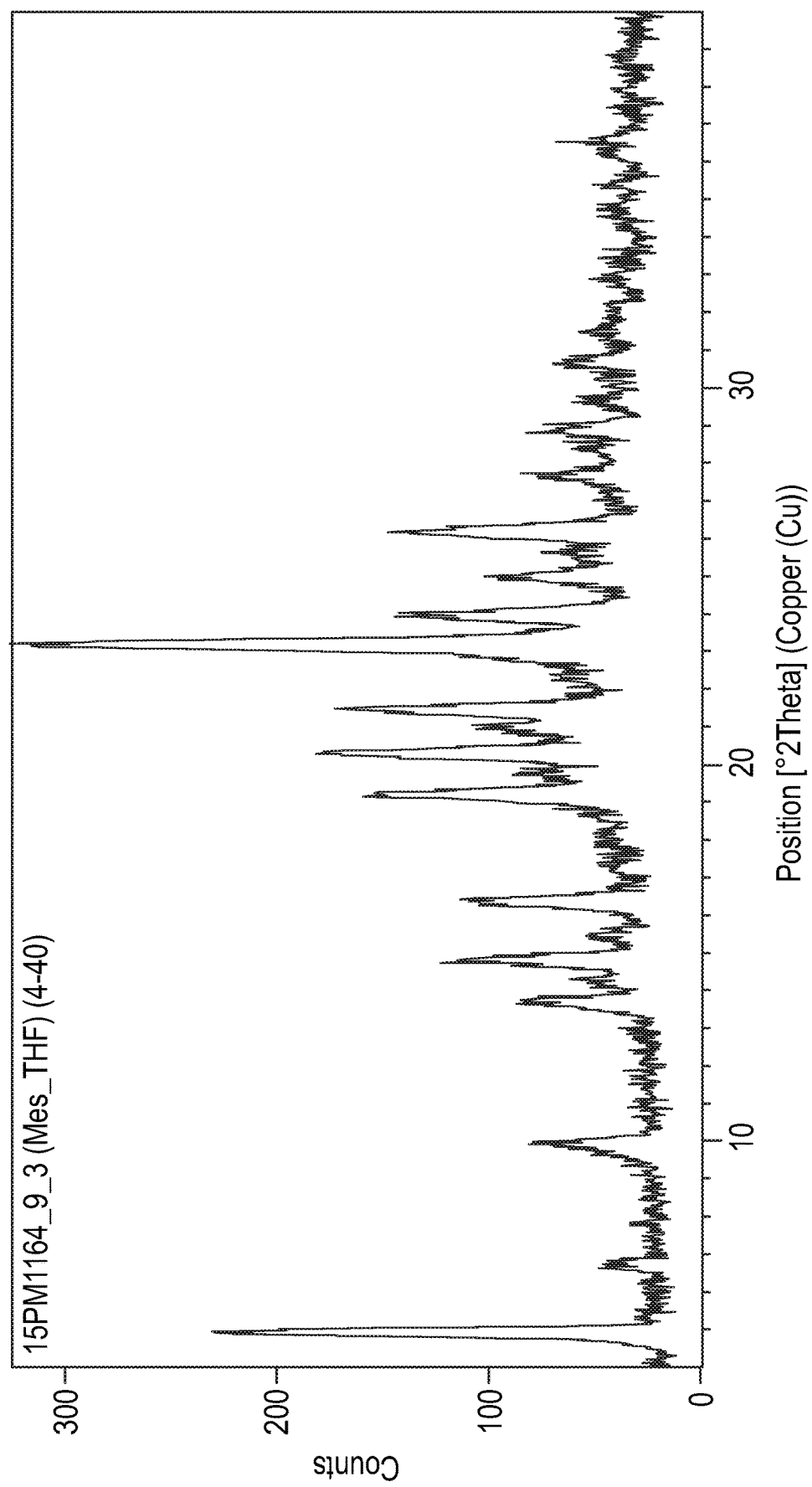

The present invention also provides a crystalline form (Form 12) of N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide mesylate having an X-ray powder diffraction pattern substantially the same as that shown in FIG. 17.

Figure 18:
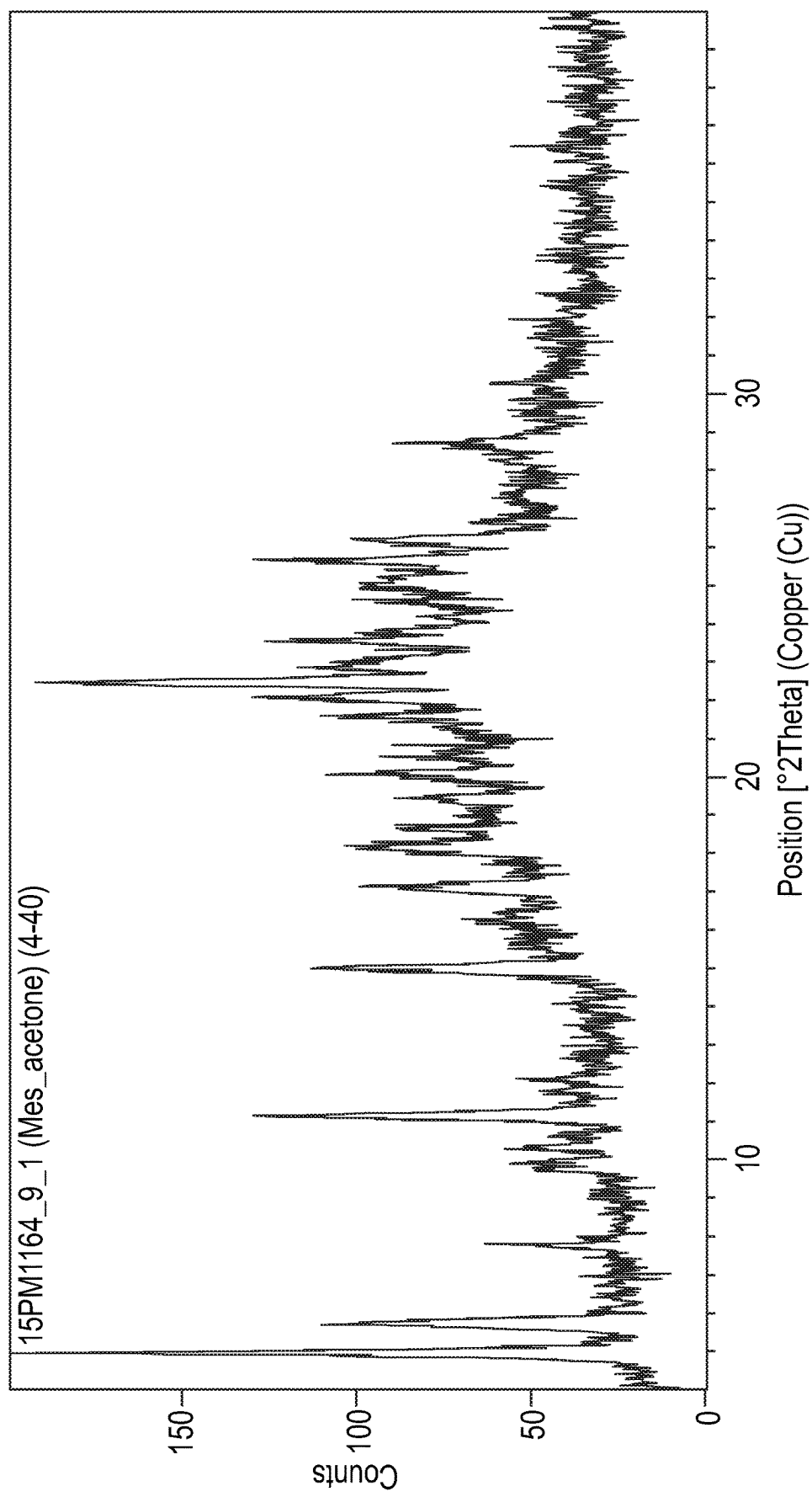

The present invention also provides a crystalline form (Form 13) of N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide mesylate having an X-ray powder diffraction pattern substantially the same as that shown in FIG. 18.

The present invention also provides a crystalline form (Form 14) of N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide tosylate, which exhibits at least the following characteristic X-ray powder diffraction peaks (Cu Kα radiation, expressed in degrees 2θ) at approximately:
(1) 5.0, 9.6, 13.7, 17.8 and 23.3; or
(2) 5.0, 9.6, 13.7, 17.8, 20.1, 23.3 and 23.6; or
(3) 5.0, 9.6, 13.7, 14.9, 17.8, 18.8, 20.1, 23.3 and 23.6.

The present invention also provides a crystalline form (Form 14) of N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide tosylate, having an X ray powder diffraction pattern comprising characteristic peaks (expressed in degrees 2θ) at approximately 5.0, 9.6, 13.7, 14.9, 17.8, 18.8, 19.0, 20.1, 23.3, 23.6 and 24.2.

Figure 19:
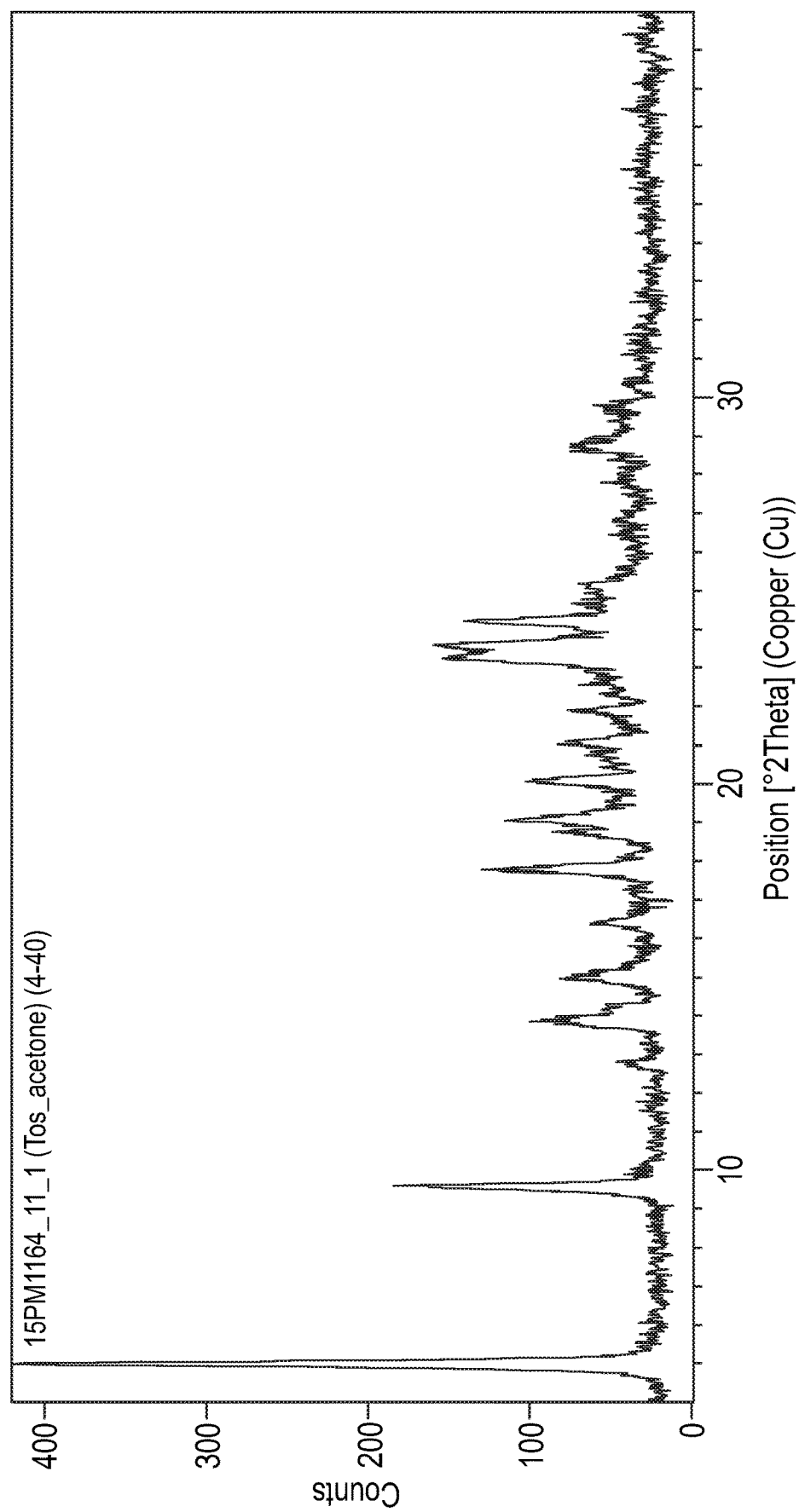

The present invention also provides a crystalline form (Form 14) of N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide tosylate having an X-ray powder diffraction pattern substantially the same as that shown in FIG. 19.

The present invention also provides a crystalline form (Form 15) of N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide edisylate, which exhibits at least the following characteristic X-ray powder diffraction peaks (Cu Kα radiation, expressed in degrees 2θ) at approximately:
(1) 7.7, 10.3, 18.3, 19.4 and 20.7; or
(2) 7.7, 10.3, 15.7, 18.3, 19.4, 20.7 and 25.7; or
(3) 7.7, 10.3, 15.7, 18.3, 19.4, 20.7, 24.1, 25.1 and 25.7.

The present invention also provides a crystalline form (Form 15) of N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide edisylate, having an X ray powder diffraction pattern comprising characteristic peaks (expressed in degrees 2θ) at approximately 7.7, 10.3, 15.7, 18.3, 19.4, 20.7, 24.1, 25.1, 25.7, 28.2 and 30.7.

Figure 20:
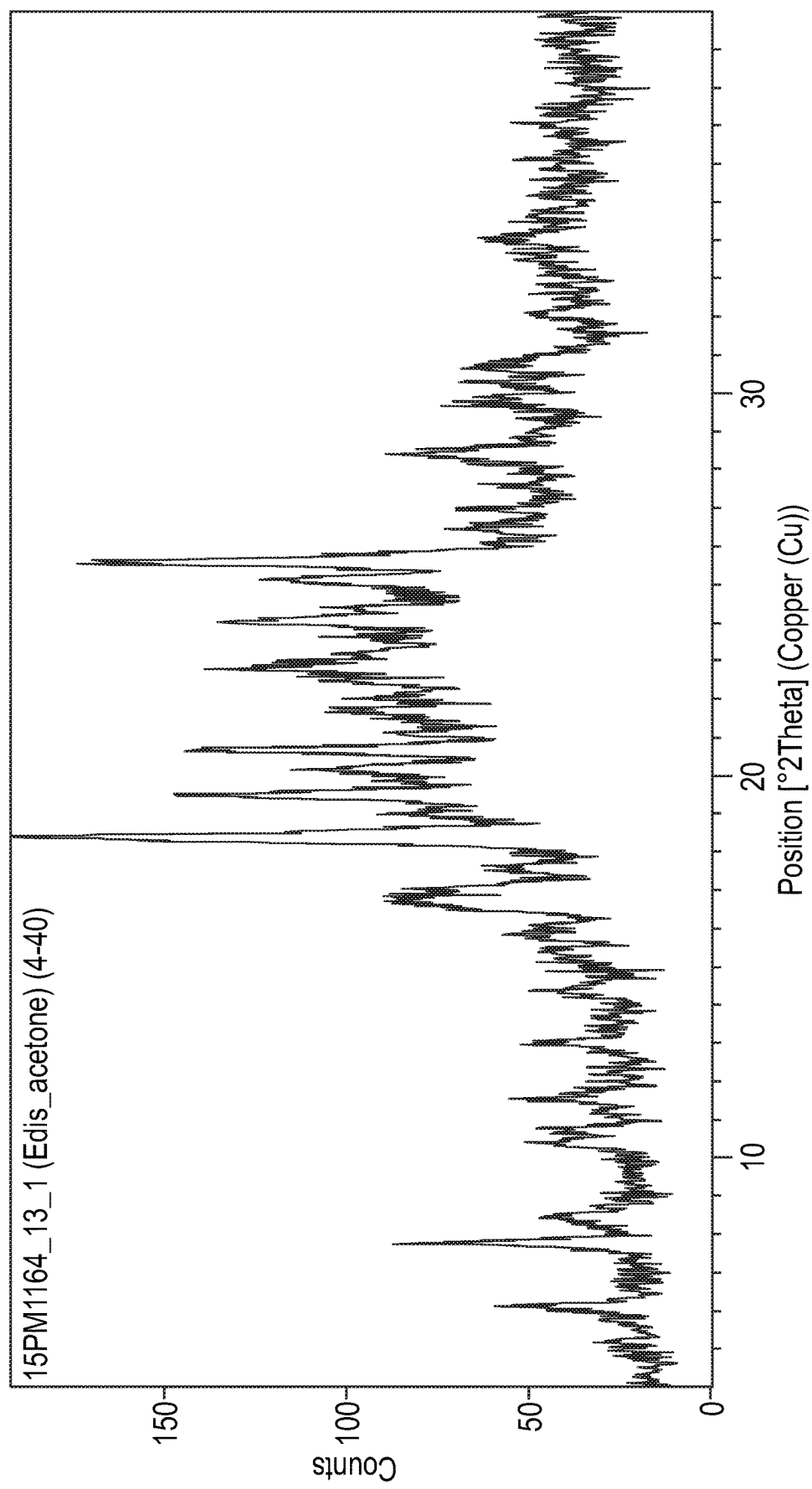
Figure 37:
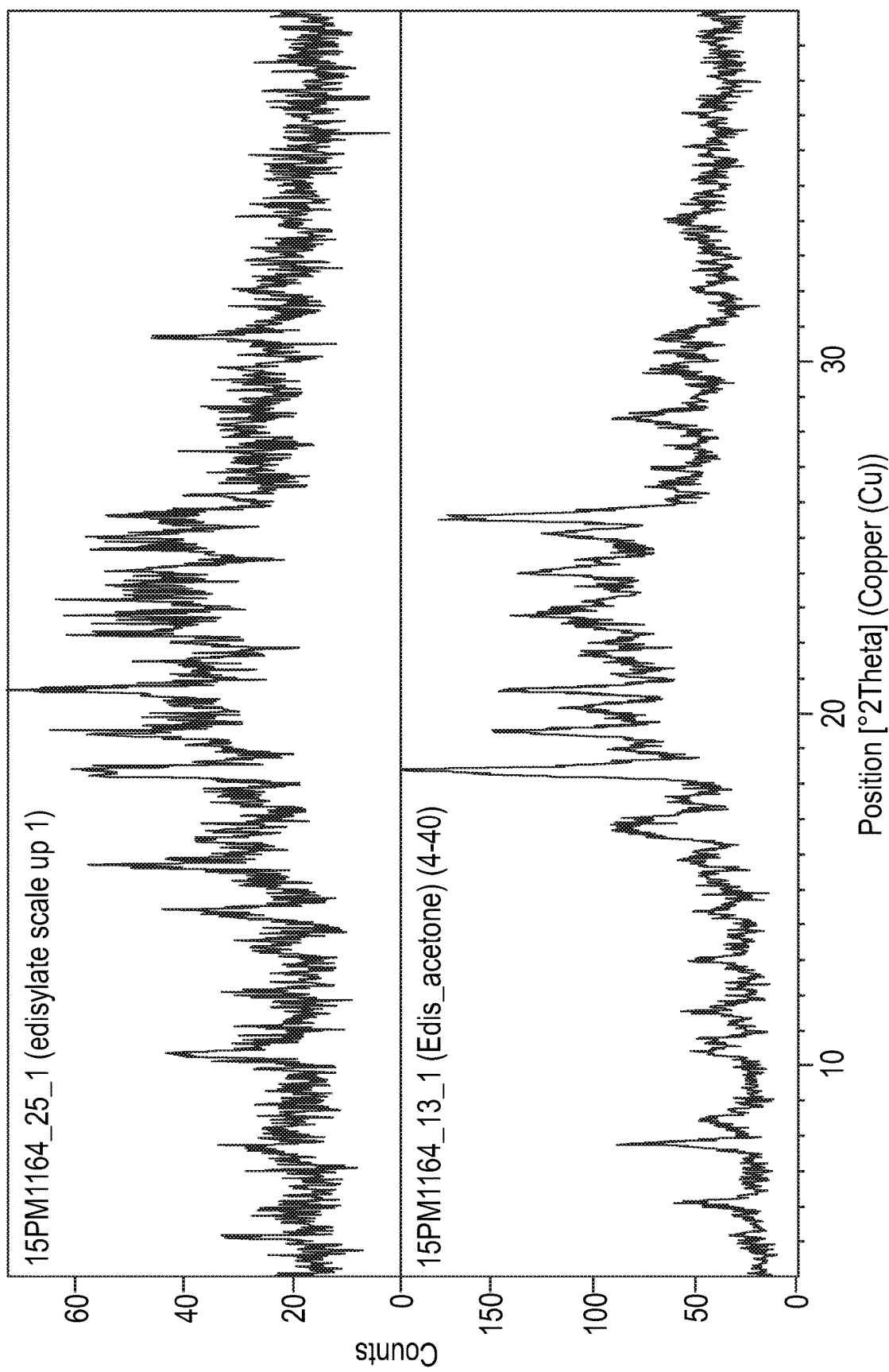

The present invention also provides a crystalline form (Form 15) of N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide edisylate having an X-ray powder diffraction pattern substantially the same as that shown in FIG. 20 or in FIG. 37 (top).

The present invention also provides a crystalline form (Form 16) of N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide edisylate, which exhibits at least the following characteristic X-ray powder diffraction peaks (Cu Kα radiation, expressed in degrees 2θ) at approximately:
(1) 10.4, 18.5, 19.5, 22.4 and 25.2; or
(2) 10.4, 18.5, 19.5, 20.8, 22.4, 24.2 and 25.2; or
(3) 5.2, 10.4, 16.5, 18.5, 19.5, 20.8, 22.4, 24.2 and 25.2.

The present invention also provides a crystalline form (Form 16) of N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide edisylate, having an X ray powder diffraction pattern comprising characteristic peaks (expressed in degrees 2θ) at approximately 5.2, 10.4, 16.1, 16.5, 18.5, 19.5, 20.8, 22.4, 23.3, 24.2 and 25.2.

Figure 21:
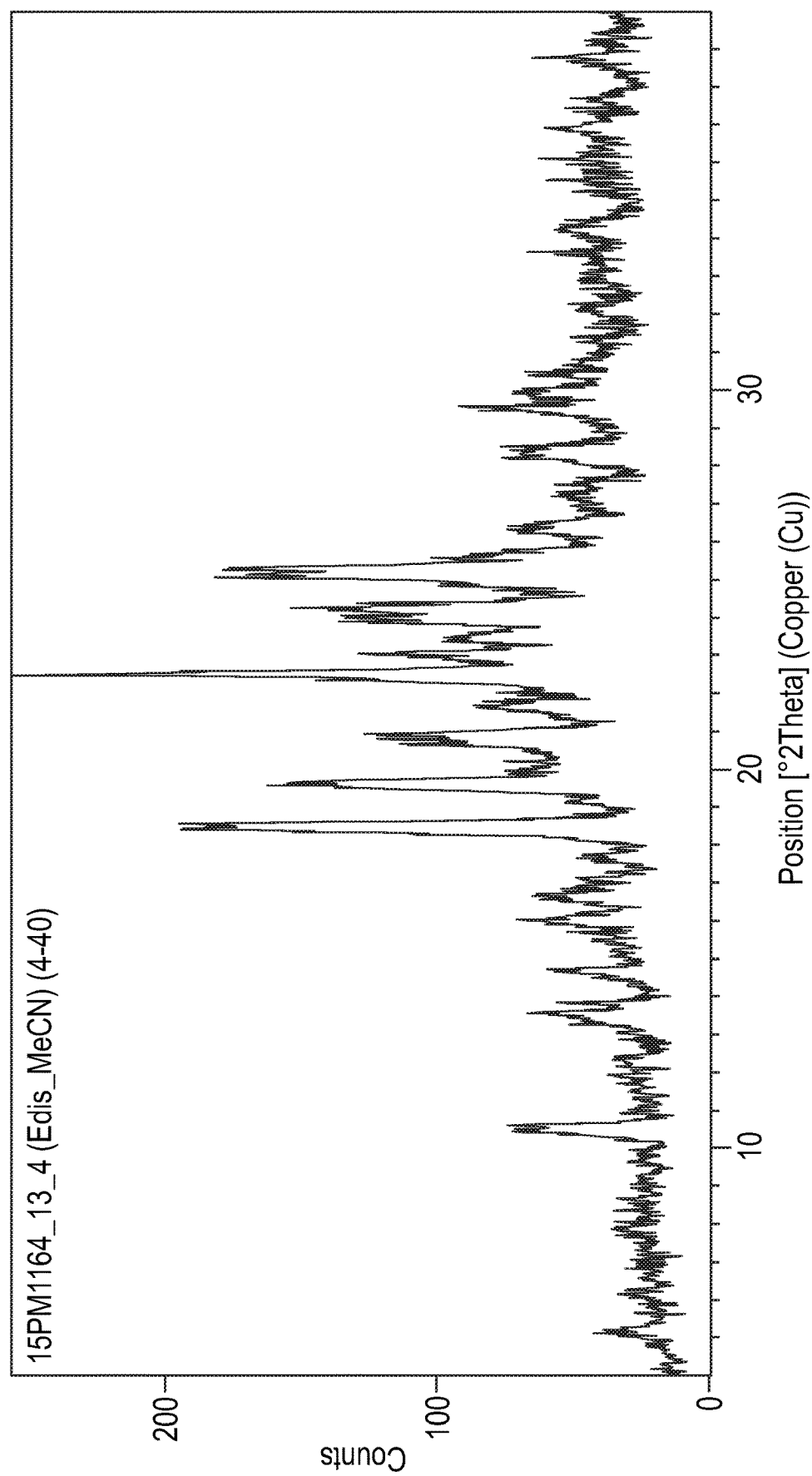
Figure 42:
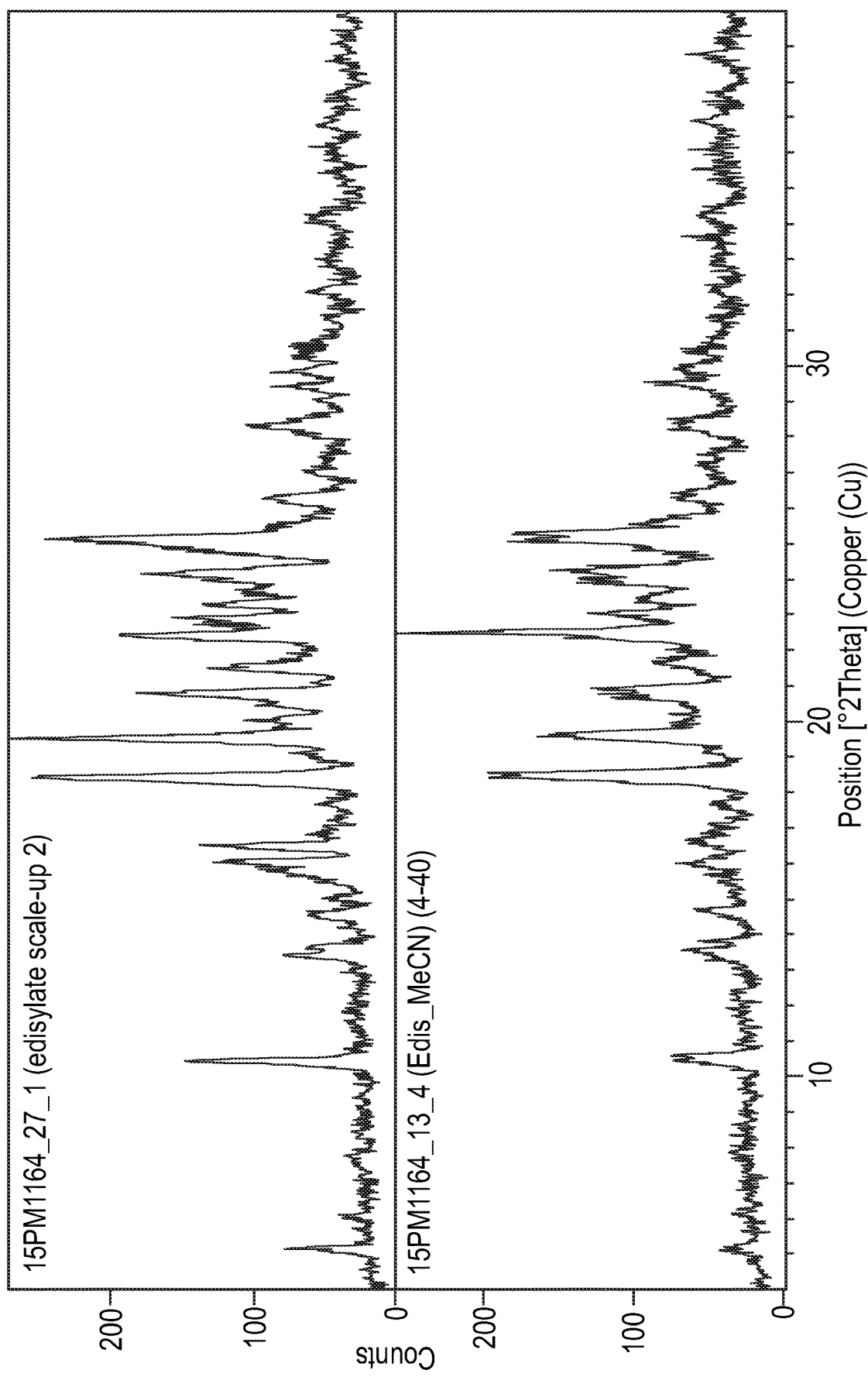

The present invention also provides a crystalline form (Form 16) of N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide edisylate having an X-ray powder diffraction pattern substantially the same as that shown in FIG. 21 or FIG. 42 (top).

The present invention also provides a crystalline form (Form 17) of N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide besylate, which exhibits at least the following characteristic X-ray powder diffraction peaks (Cu Kα radiation, expressed in degrees 2θ) at approximately:
(1) 5.3, 9.8, 14.9, 19.9, and 23.1; or
(2) 5.3, 9.8, 14.9, 19.2, 19.9, 23.1 and 24.6; or
(3) 5.3, 9.8, 14.9, 16.4, 17.4, 19.2, 19.9, 23.1 and 24.6.

The present invention also provides a crystalline form (Form 17) of N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide besylate, having an X ray powder diffraction pattern comprising characteristic peaks (expressed in degrees 2θ) at approximately 5.3, 9.8, 14.9, 16.4, 17.4, 19.2, 19.9, 21.0, 22.3, 23.1, 24.6 and 25.8.

Figure 22:
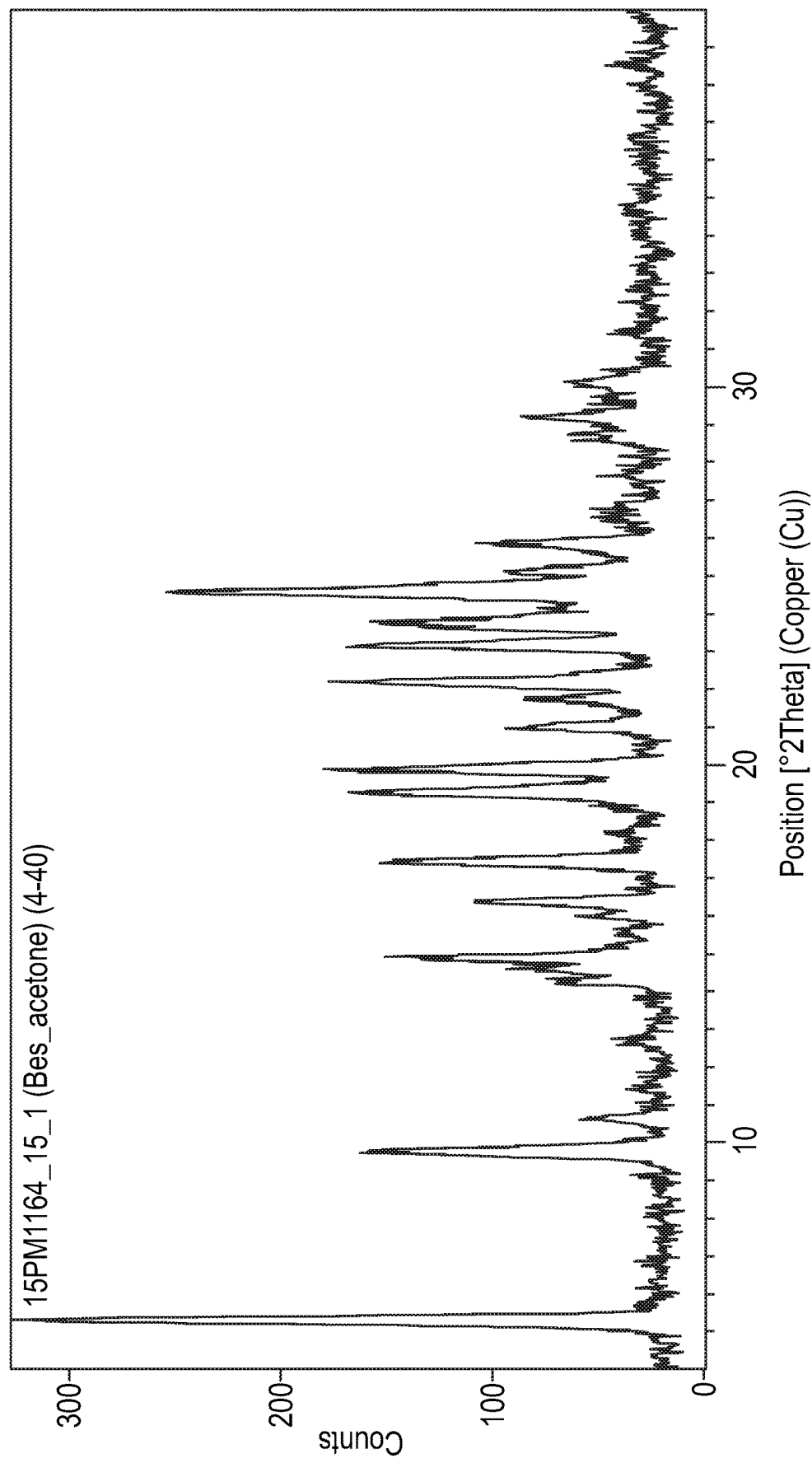

The present invention also provides a crystalline form (Form 17) of N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide besylate having an X-ray powder diffraction pattern substantially the same as that shown in FIG. 22.

The present invention also provides a crystalline form (Form 18) of N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide hydrochloride, which exhibits at least the following characteristic X-ray powder diffraction peaks (Cu Kα radiation, expressed in degrees 2θ) at approximately:
(1) 5.5, 8.5, 11.6, 17.0 and 19.0; or
(2) 5.5, 8.5, 11.6, 17.0, 19.0, 22.8 and 26.1; or
(3) 5.5, 8.5, 11.6, 13.2, 17.0, 19.0, 22.8, 23.8 and 26.2.

The present invention also provides a crystalline form (Form 18) of N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide hydrochloride, having an X ray powder diffraction pattern comprising characteristic peaks (expressed in degrees 2θ) at approximately 5.5, 7.3, 8.5, 11.6, 13.2, 17.0, 19.0, 20.6, 22.8, 23.8 and 26.2.

Figure 24:
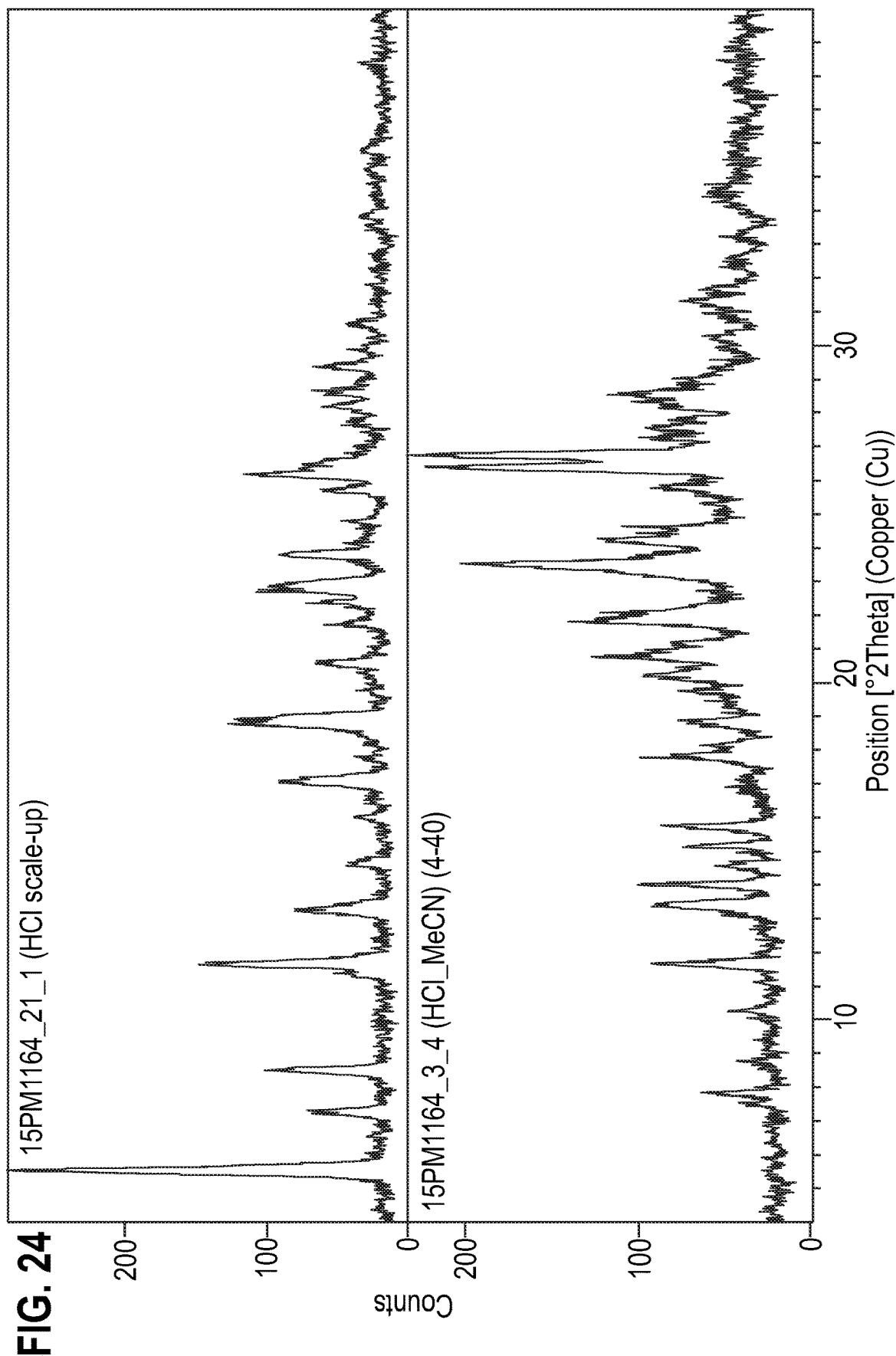

The present invention also provides a crystalline form (Form 18) of N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide hydrochloride having an X-ray powder diffraction pattern substantially the same as that shown in FIG. 24 (top).

The skilled person is familiar with techniques for measuring XRPD patterns. In particular, the X-ray powder diffraction pattern of the sample of compound may be recorded using a Philips X-Pert MPD diffractometer with the following experimental conditions:
Tube anode: Cu;
Generator tension: 40 kV;
Tube current: 40 mA;
Wavelength alpha1: 1.5406 Å;
Wavelength alpha2: 1.5444 Å;
Sample: 2 mg of sample under analysis gently compressed on the XRPD zero back ground single obliquely cut silica sample holder.

The present invention provides a crystalline form (Form 1) of N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide, which exhibits an endothermic peak in its DSC thermograph at 151±3° C., preferably 151±2° C., more preferably 151±1° C.

Figure 4:
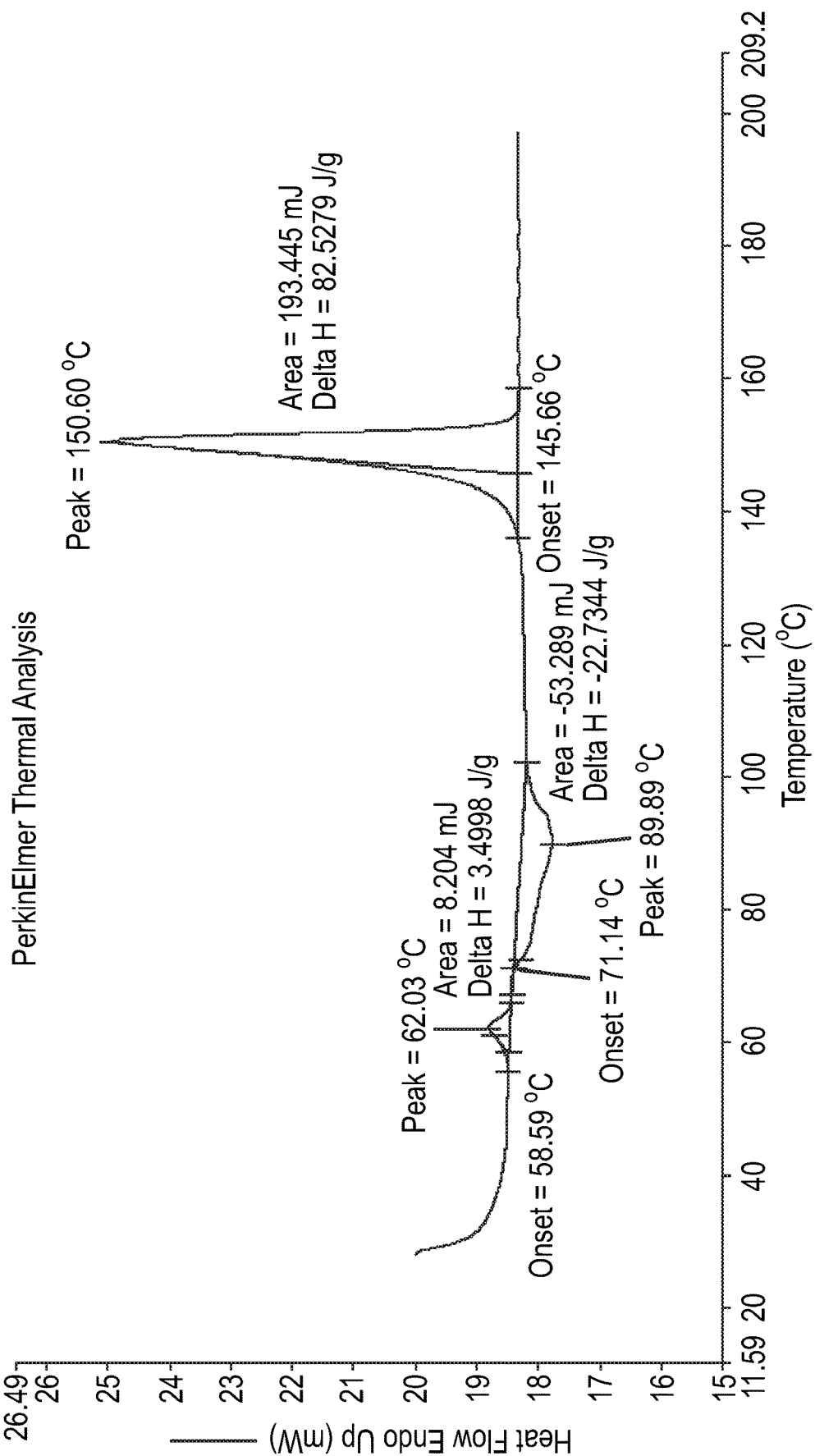

The present invention provides a crystalline form (Form 1) of N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide, having a DSC thermograph substantially the same as that shown in FIG. 4.

The present invention provides a crystalline form (Form 18) of N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide hydrochloride, which exhibits an endothermic peak in its DSC thermograph at 149±3° C., preferably 149±2° C., more preferably 149±1° C.

Figure 26:
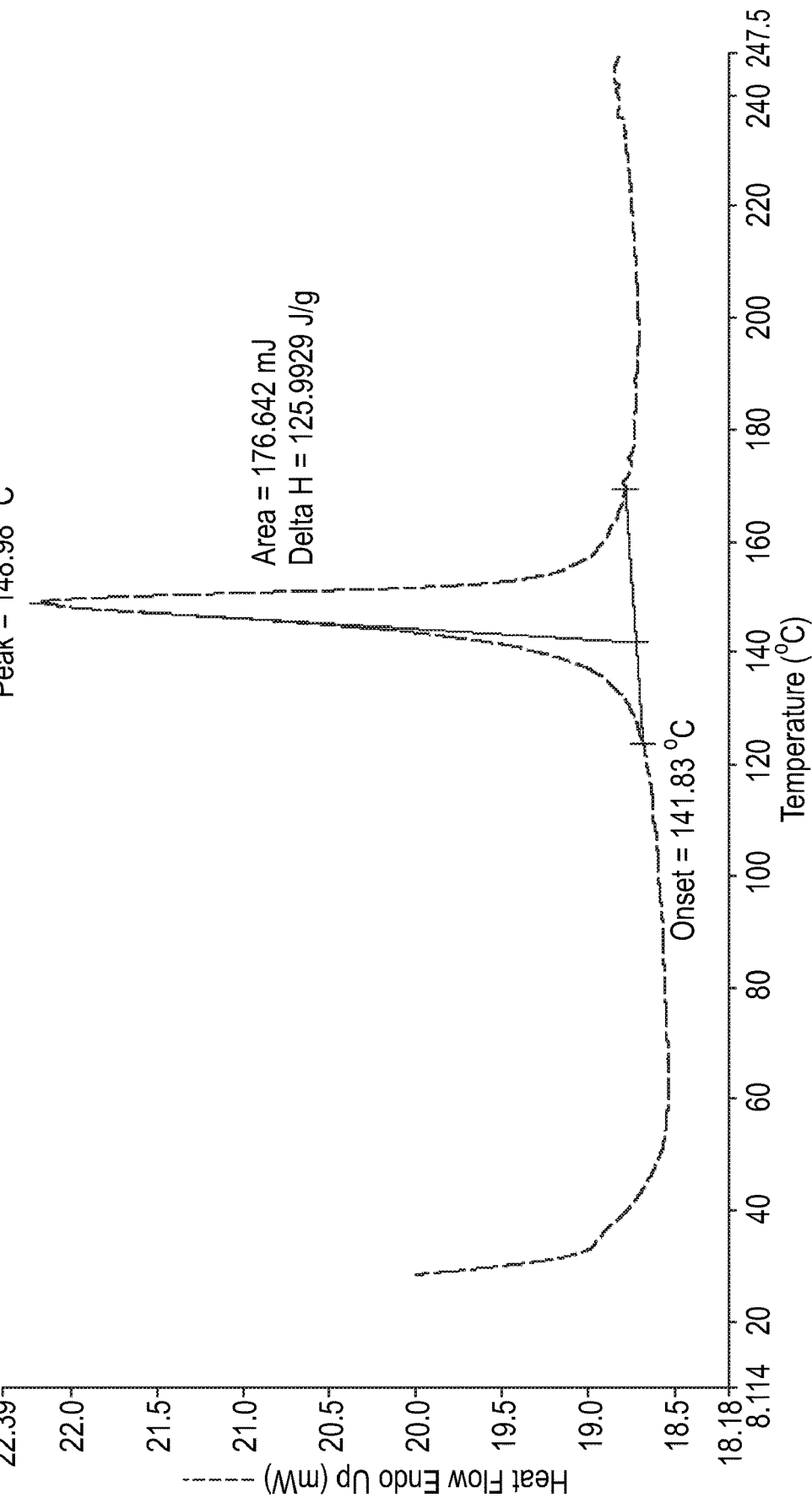

The present invention provides a crystalline form (Form 18) of N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide hydrochloride, having a DSC thermograph substantially the same as that shown in FIG. 26.

The present invention provides a crystalline form (Form 8) of N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide sulfate, which exhibits an endothermic peak in its DSC thermograph at 110±3° C., preferably 110±2° C., more preferably 110±1° C.

Figure 32:
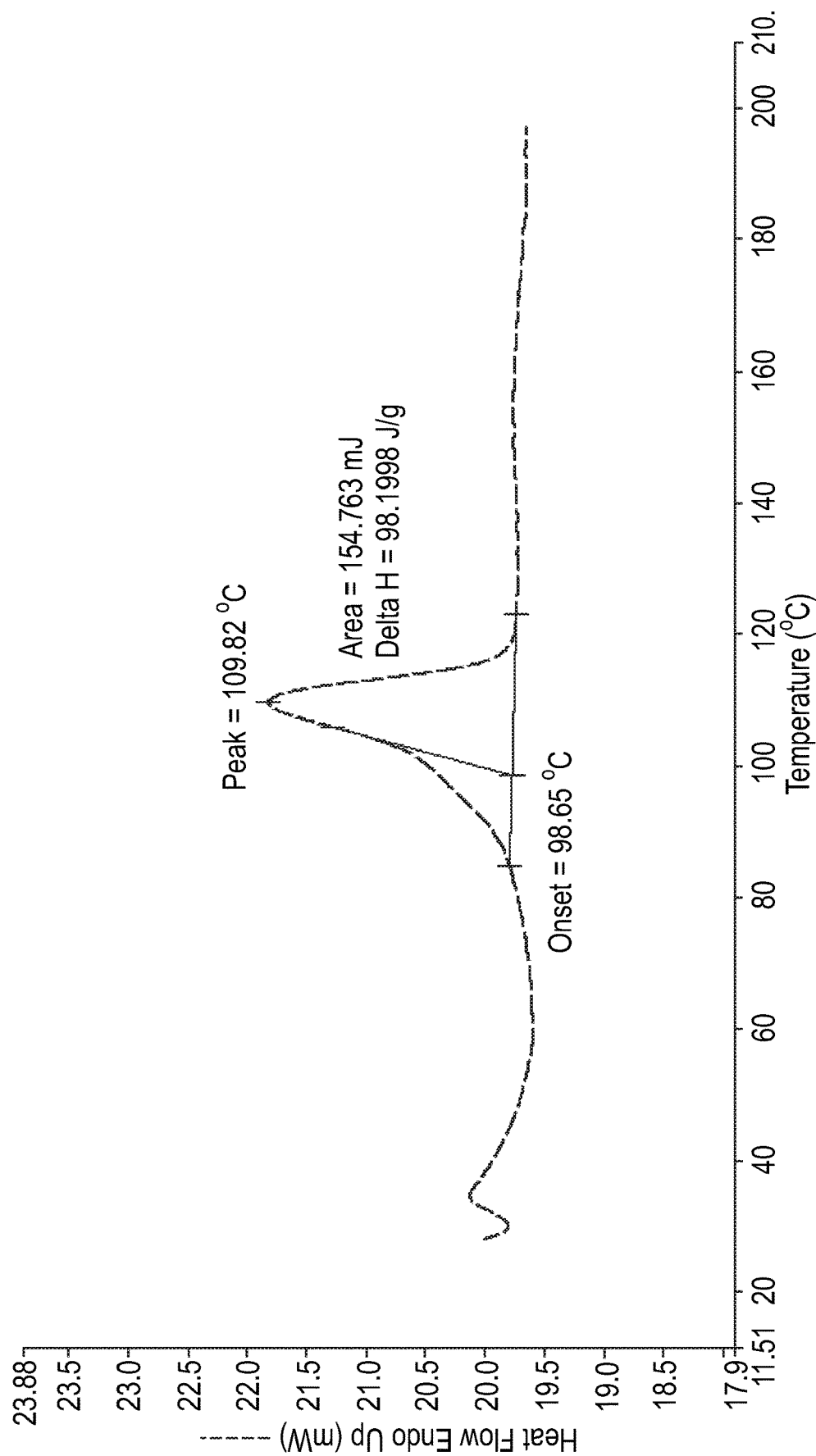

The present invention provides a crystalline form (Form 8) of N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide sulfate, having a DSC thermograph substantially the same as that shown in FIG. 32.

The present invention provides a crystalline form (Form 16) of N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide edisylate, which exhibits an endothermic peak in its DSC thermograph at 110±3° C., preferably 110±2° C., more preferably 110±1° C.

Figure 44:
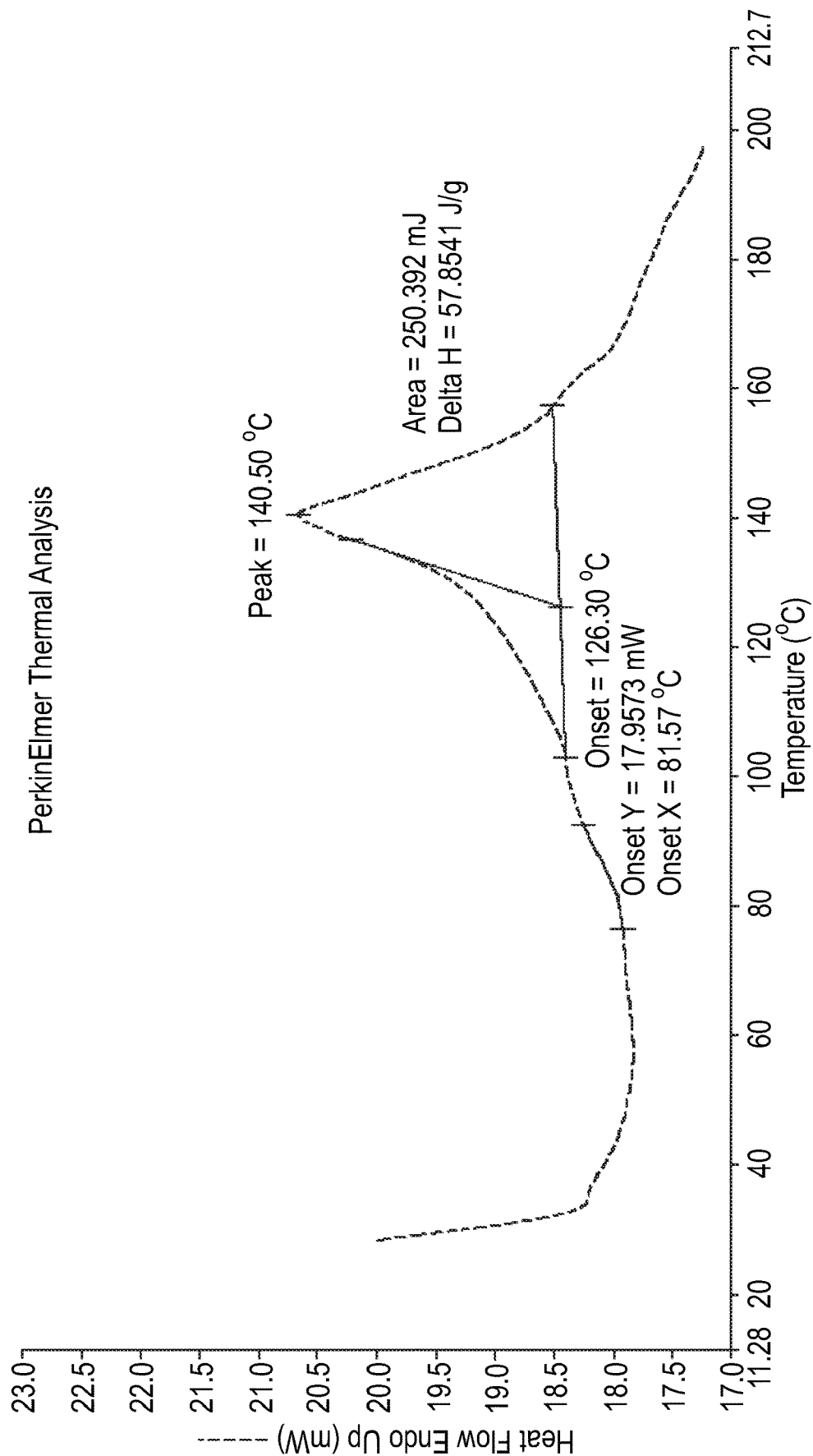

The present invention provides a crystalline form (Form 16) of N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide edisylate, having a DSC thermograph substantially the same as that shown in FIG. 44.

The skilled person is familiar with techniques for measuring DSC thermographs. In particular, the DSC thermograph of the sample of compound may be recorded by
(a) weighing 5 mg of the sample into an aluminium DSC pan and sealing non-hermetically with an aluminium lid;
(b) loading the sample into a Perkin-Elmer Jade DSC and holding the sample at 30° C. until a stable heat-flow response is obtained while using a 20 cm$^3$/min helium purge;
(c) heating the sample to a temperature of between 200 and 300° C. at a scan rate of 10° C./min and monitoring the resulting heat flow response while using a 20 cm$^3$/min helium purge.

The present invention provides a crystalline form (Form 1) of N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide having an X-ray powder diffraction pattern as described above, and a DSC thermograph as described above.

The present invention provides a crystalline form (Form 18) of N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide hydrochloride having an X-ray powder diffraction pattern as described above, and a DSC thermograph as described above.

The present invention provides a crystalline form (Form 8) of N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide sulfate having an X-ray powder diffraction pattern as described above, and a DSC thermograph as described above.

The present invention provides a crystalline form (Form 16) of N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide edisylate having an X-ray powder diffraction pattern as described above, and a DSC thermograph as described above.

The crystalline form of the present invention can exist in both unsolvated and solvated forms. The term 'solvate' is used herein to describe a molecular complex comprising the compound of the invention and an amount of one or more pharmaceutically acceptable solvents, for example, methanol. The term 'hydrate' is employed when the solvent is water.

A reference to a particular compound also includes all isotopic variants.

The present invention also encompasses a process for the preparation of Form 1 of the present invention, said process comprising the crystallisation of said crystalline form from a solution of N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide in a solvent or a mixture of solvents. Preferably the solvent is selected from acetonitrile and isopropanol (IPA). More preferably the solvent is isopropanol. After adding the N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide to a solvent or a mixture of solvents (e.g. acetonitrile or isopropanol), the combined mixture (compound plus solvent(s)) may be heated to a temperature of approximately 60-85° C. Alternatively, the combined mixture may be heated to a temperature of approximately 70-85° C. Alternatively, the combined mixture may be heated to a temperature of approximately 80-85° C. Alternatively, the combined mixture may be heated to a temperature of approximately 80, 81, 82, 83, 84 or 85° C. Alternatively, the combined mixture may be heated to a temperature of approximately 82° C. Alternatively, the combined mixture may be heated to reflux. Following heating, the combined mixture may be cooled. Alternatively, the combined mixture may be cooled to a temperature of approximately 0-40° C. Alternatively, the combined mixture may be cooled to a temperature of approximately 10-30° C. Alternatively, the combined mixture may be cooled to room temperature. Alternatively, the combined mixture may be cooled to approximately 0° C.

The present invention also encompasses a process for the preparation of Form 18 of the present invention, said process comprising the crystallisation of said crystalline form from a solution of N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide hydrochloride in a solvent or a mixture of solvents. Optionally, said solution of N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide hydrochloride may be formed by adding hydrochloric acid to a solution of N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide in a solvent or a mixture of solvents. Preferably, the solution of N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide in a solvent or a mixture of solvents may be heated such that the solid is dissolved before the hydrochloric acid is added. Preferably, the solvent is ethyl acetate or acetonitrile. More preferably, the solvent is acetonitrile. The crystallisation may be performed by ultrasonication and/or temperature cycling of the mixture. Preferably the crystallisation is performed by ultrasonication followed by temperature cycling of the mixture. The temperature cycling may comprise cycling the temperature of the mixture between about 30-50° C. and ambient temperature, optionally between about 40° C. and ambient temperature. Preferably, the temperature cycling is carried out for between about 18 to about 24 hours.

The present invention also encompasses a process for the preparation of Form 8 of the present invention, said process comprising the crystallisation of said crystalline form from a solution of N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide sulfate in a solvent or a mixture of solvents. Optionally, said solution of N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide sulfate may be formed by adding sulfuric acid to a solution of N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide in a solvent or a mixture of solvents. Preferably, the solution of N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide in a solvent or a mixture of solvents may be heated such that the solid is dissolved before the sulfuric acid is added. Preferably, the solvent is acetonitrile or acetone. More preferably, the solvent is acetonitrile. The crystallisation may be performed by ultrasonication and/or temperature cycling of the mixture. Preferably the crystallisation is performed by ultrasonication followed by temperature cycling of the mixture. The temperature cycling may comprise cycling the temperature of the mixture between about 30-50° C. and ambient temperature, optionally between about 40° C. and ambient temperature. Preferably, the temperature cycling is carried out for between about 18 to about 24 hours.

The present invention also encompasses a process for the preparation of Form 15 of the present invention, said process comprising the crystallisation of said crystalline form from a suspension of N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide edisylate in a solvent or a mixture of solvents. Optionally, said suspension of N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide edisylate may be formed by adding a solvent or a mixture of solvents to a mixture of ethane disulphonic acid (e.g. ethane disulphonic acid hydrate) and N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide. Preferably, the solvent is acetone or ethyl acetate. More preferably, the solvent is acetone. The crystallisation may be performed by ultrasonication and/or temperature cycling of the suspension. Preferably the crystallisation is performed by ultrasonication followed by temperature cycling of the suspension. The temperature cycling may comprise cycling the temperature of the suspension between about 30-50° C. and ambient temperature, optionally between about 40° C. and ambient temperature. Preferably, the temperature cycling is carried out for between about 18 to about 24 hours.

The present invention also encompasses a process for the preparation of Form 16 of the present invention, said process comprising the crystallisation of said crystalline form from a solution of N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide edisylate in a solvent or a mixture of solvents. Optionally, said solution of N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide edisylate may be formed by adding a solvent or a mixture of solvents to a mixture of ethane disulphonic acid (e.g. ethane disulphonic acid hydrate) and N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide. Optionally ethane disulphonic acid and the mixture of N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide is heated until to dissolve the solid. Preferably, the solvent is tetrahydrofuran or acetonitrile. More preferably, the solvent is acetonitrile. The crystallisation may be performed by ultrasonication and/or temperature cycling of the mixture. Preferably the crystallisation is performed by ultrasonication followed by temperature cycling of the mixture. The temperature cycling may comprise cycling the temperature of the suspension between about 30-50° C. and ambient temperature, optionally between about 40° C. and ambient temperature. Preferably, the temperature cycling is carried out for between about 18 to about 24 hours.

The processes of the present invention may also comprise the addition of crystalline seeds of the crystalline form of the invention.

In an aspect, the present invention provides the crystalline form of the invention when manufactured by a process according to the invention.

As previously mentioned, the crystalline form of the present invention has a number of therapeutic applications, particularly in the treatment of diseases or conditions mediated by plasma kallikrein.

Accordingly, the present invention provides a crystalline form of N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide and salts thereof, as hereinbefore defined, for use in therapy. In a preferred embodiment, the crystalline form is Form 1. In another preferred embodiment, the crystalline form is Form 8.

The present invention also provides for the use of a crystalline form of N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide and salts thereof, as hereinbefore defined, in the manufacture of a medicament for the treatment of a disease or condition mediated by plasma kallikrein. In a preferred embodiment, the crystalline form is Form 1. In another preferred embodiment, the crystalline form is Form 8.

The present invention also provides a crystalline form of N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide and salts thereof, as hereinbefore defined, for use in a method of treatment of a disease or condition mediated by plasma kallikrein. In a preferred embodiment, the crystalline form is Form 1. In another preferred embodiment, the crystalline form is Form 8.

The present invention also provides a method of treatment of a disease or condition mediated by plasma kallikrein, said method comprising administering to a mammal in need of such treatment a therapeutically effective amount of a crystalline form of N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide and salts thereof, as hereinbefore defined. In a preferred embodiment, the crystalline form is Form 1. In another preferred embodiment, the crystalline form is Form 8.

In an aspect, the disease or condition mediated by plasma kallikrein is selected from impaired visual acuity, diabetic retinopathy, retinal vascular permeability associated with diabetic retinopathy, diabetic macular edema, hereditary angioedema, diabetes, pancreatitis, cerebral haemorrhage, nephropathy, cardiomyopathy, neuropathy, inflammatory bowel disease, arthritis, inflammation, septic shock, hypotension, cancer, adult respiratory distress syndrome, disseminated intravascular coagulation, blood coagulation during cardiopulmonary bypass surgery, and bleeding from post-operative surgery. In a preferred embodiment, the disease or condition mediated by plasma kallikrein is diabetic macular edema. In another preferred embodiment, the disease or condition mediated by plasma kallikrein is hereditary angioedema.

In another aspect, the disease or condition in which plasma kallikrein activity is implicated is retinal vein occlusion.

Alternatively, the disease or condition mediated by plasma kallikrein may be selected from retinal vascular permeability associated with diabetic retinopathy, diabetic macular edema and hereditary angioedema. Alternatively, the disease or condition mediated by plasma kallikrein may be retinal vascular permeability associated with diabetic retinopathy or diabetic macular edema. The crystalline forms of N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide and salts thereof may be administered in a form suitable for injection into the ocular region of a patient, in particular, in a form suitable for intra-vitreal injection.

In the context of the present invention, references herein to "treatment" include references to curative, palliative and prophylactic treatment, unless there are specific indications to the contrary. The terms "therapy", "therapeutic" and "therapeutically" should be construed in the same way.

The crystalline form of the present invention may be administered alone or in combination with one or more other drugs. Generally, it will be administered as a formulation in association with one or more pharmaceutically acceptable excipients. The term "excipient" is used herein to describe any ingredient other than the compound(s) of the invention which may impart either a functional (i.e., drug release rate controlling) and/or a non-functional (i.e., processing aid or diluent) characteristic to the formulations. The choice of excipient will to a large extent depend on factors such as the particular mode of administration, the effect of the excipient on solubility and stability, and the nature of the dosage form.

In another aspect, the compounds of the present invention may be administered in combination with laser treatment of the retina. The combination of laser therapy with intravitreal injection of an inhibitor of VEGF for the treatment of diabetic macular edema is known (Elman M, Aiello L, Beck R, et al. "Randomized trial evaluating ranibizumab plus prompt or deferred laser or triamcinolone plus prompt laser for diabetic macular edema". Ophthalmology. 27 Apr. 2010).

Pharmaceutical compositions suitable for the delivery of the crystalline form of the present invention and methods for their preparation will be readily apparent to those skilled in the art. Such compositions and methods for their preparation may be found, for example, in Remington's Pharmaceutical Sciences, 19th Edition (Mack Publishing Company, 1995).

For administration to human patients, the total daily dose of the crystalline form of the invention is typically in the range 0.1 mg and 10,000 mg, or between 1 mg and 5000 mg, or between 10 mg and 1000 mg depending, of course, on the mode of administration. If administered by intra-vitreal injection a lower dose of between 0.0001 mg (0.1 μg) and 0.2 mg (200 μg) per eye is envisaged, or between 0.0005 mg (0.5 μg) and 0.05 mg (50 μg) per eye.

The total daily dose may be administered in single or divided doses and may, at the physician's discretion, fall outside of the typical range given herein. These dosages are based on an average human subject having a weight of about 60 kg to 70 kg. The physician will readily be able to determine doses for subjects whose weight falls outside this range, such as infants and the elderly.

Accordingly, the present invention provides a pharmaceutical composition comprising a crystalline solid form of N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide, as hereinbefore defined, and a pharmaceutically acceptable carrier, diluent or excipient. In a preferred embodiment, the crystalline solid form is Form 1. In another preferred embodiment, the crystalline form is Form 8. It will be appreciated that the reference to crystalline solid forms of N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide as hereinbefore defined includes both the free base and the salts thereof which have hereinbefore been described.

The pharmaceutical compositions may be administered topically (e.g. to the eye, to the skin or to the lung and/or airways) in the form, e.g., of eye-drops, creams, solutions, suspensions, heptafluoroalkane (HFA) aerosols and dry powder formulations; or systemically, e.g. by oral administration in the form of tablets, capsules, syrups, powders or granules; or by parenteral administration in the form of solutions or suspensions; or by subcutaneous administration; or by rectal administration in the form of suppositories; or transdermally. In a further embodiment, the pharmaceutical composition is in the form of a suspension, tablet, capsule, powder, granule or suppository.

In an embodiment of the invention, the active ingredient is administered orally. Oral administration may involve swallowing, so that the compound enters the gastrointestinal tract, and/or buccal, lingual, or sublingual administration by which the compound enters the blood stream directly from the mouth.

Formulations suitable for oral administration include solid plugs, solid microparticulates, semi-solid and liquid (including multiple phases or dispersed systems) such as tablets; soft or hard capsules containing multi- or nano-particulates, liquids, emulsions or powders; lozenges (including liquid-filled); chews; gels; fast dispersing dosage forms; films; ovules; sprays; and buccal/mucoadhesive patches.

Formulations suitable for oral administration may also be designed to deliver the crystalline form in an immediate release manner or in a rate-sustaining manner, wherein the release profile can be delayed, pulsed, controlled, sustained, or delayed and sustained or modified in such a manner which optimises the therapeutic efficacy of the said crystalline form. Means to deliver compounds in a rate-sustaining manner are known in the art and include slow release polymers that can be formulated with the said compounds to control their release.

Liquid (including multiple phases and dispersed systems) formulations include emulsions, suspensions, solutions, syrups and elixirs. Such formulations may be presented as fillers in soft or hard capsules. Liquid formulations may also be prepared by the reconstitution of a solid, for example, from a sachet.

The crystalline form of the invention may also be used in fast-dissolving, fast-disintegrating dosage forms such as those described in Liang and Chen, Expert Opinion in Therapeutic Patents, 2001, 11 (6), 981-986.

The formulation of tablets is discussed in Pharmaceutical Dosage Forms: Tablets, Vol. 1, by H. Lieberman and L. Lachman (Marcel Dekker, New York, 1980).

The invention will now be illustrated by the following non-limiting examples. In the examples the following figures are presented:

FIG. 1*a*: X-ray powder diffraction pattern of Form A of N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide (Example 41 of WO2016/083820 (PCT/GB2015/053615)).

Figure 1B:
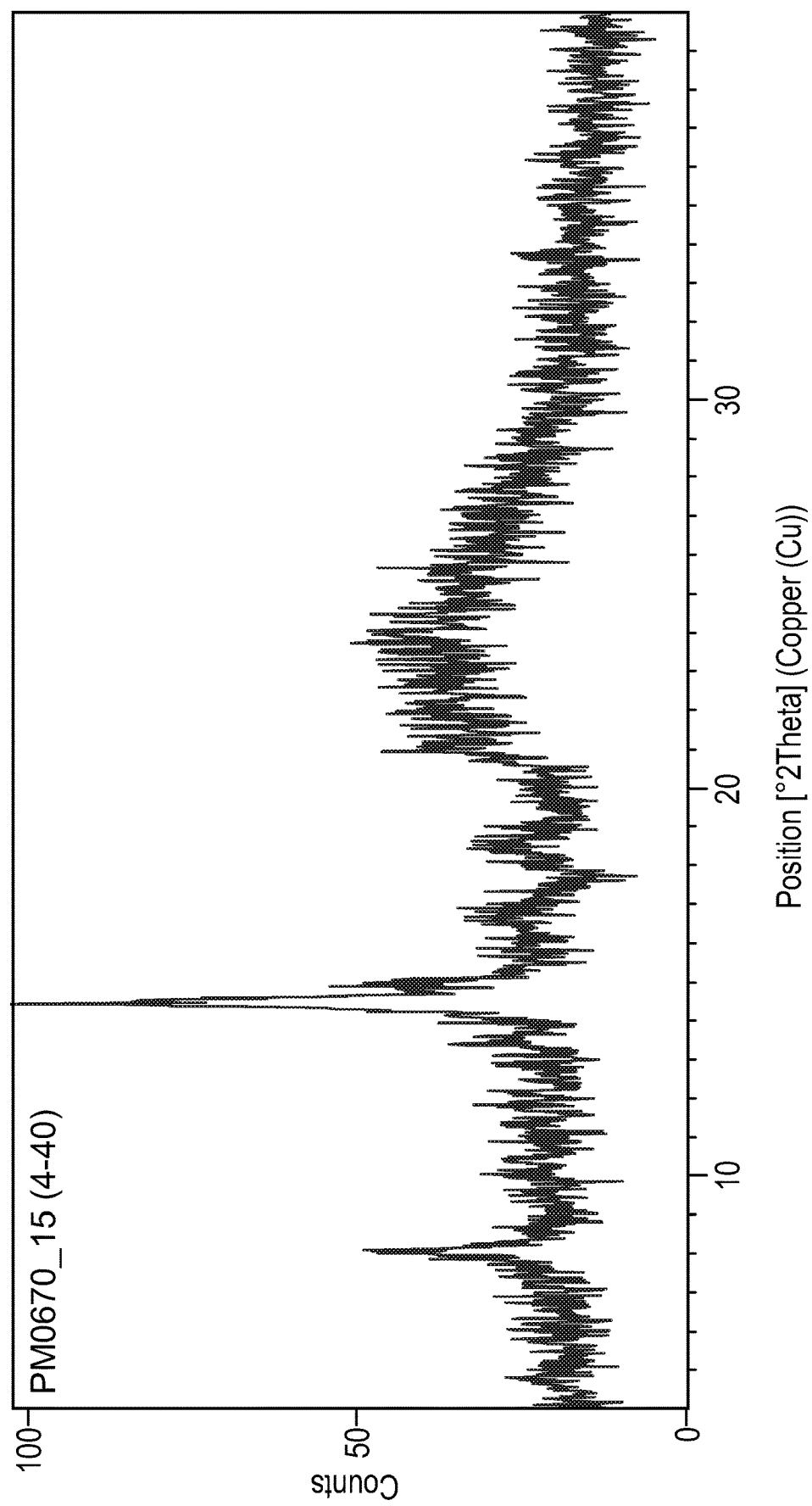

FIG. 1*b*: X-ray powder diffraction pattern of Form A of N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide (Example 1).

FIG. 2*a*: X-ray powder diffraction pattern of Form 1 of N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide (Example 2).

Figure 2B:
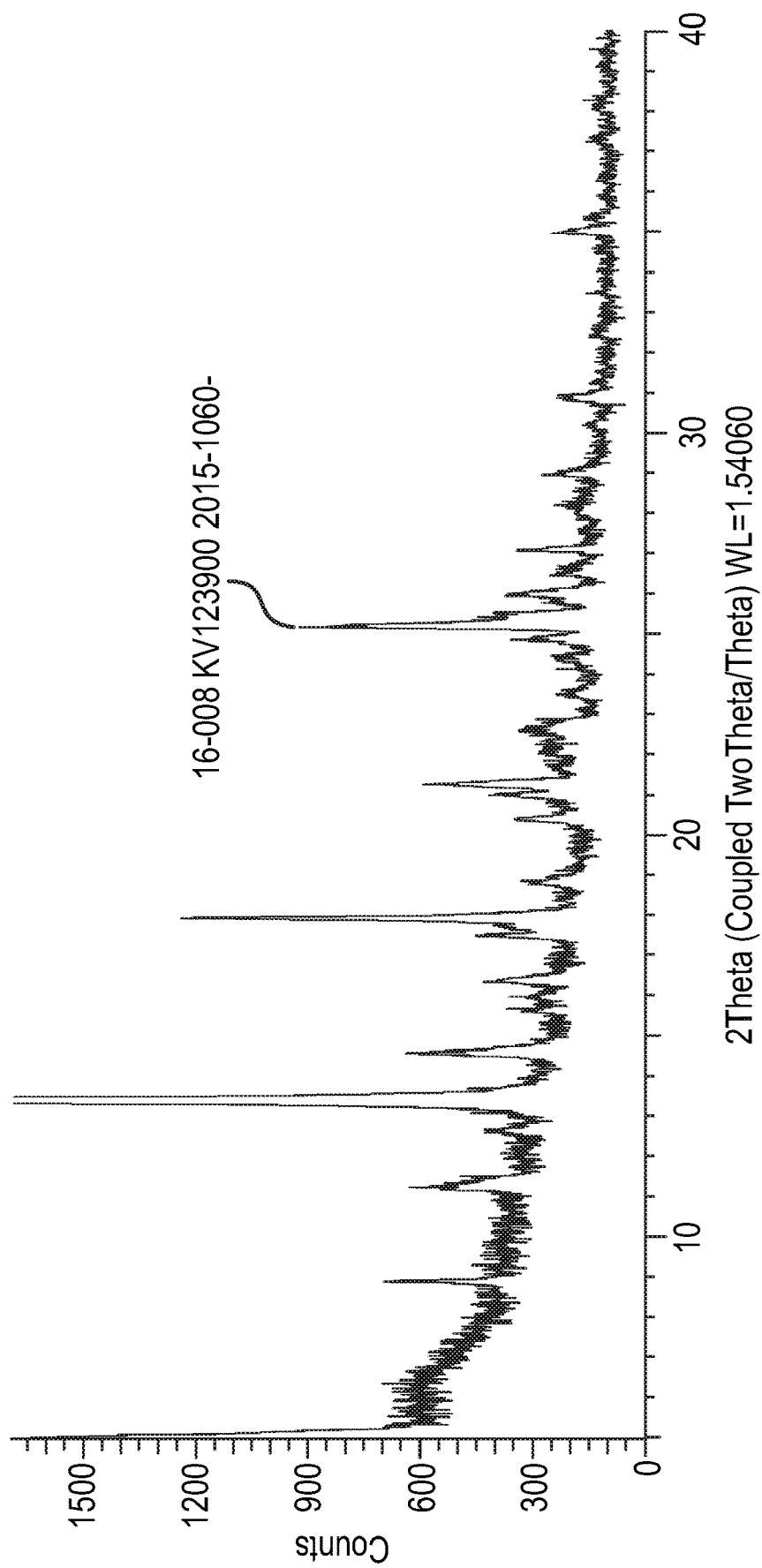

FIG. 2*b*: X-ray powder diffraction pattern of Form 1 of N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide (Example 3).

Figure 2C:
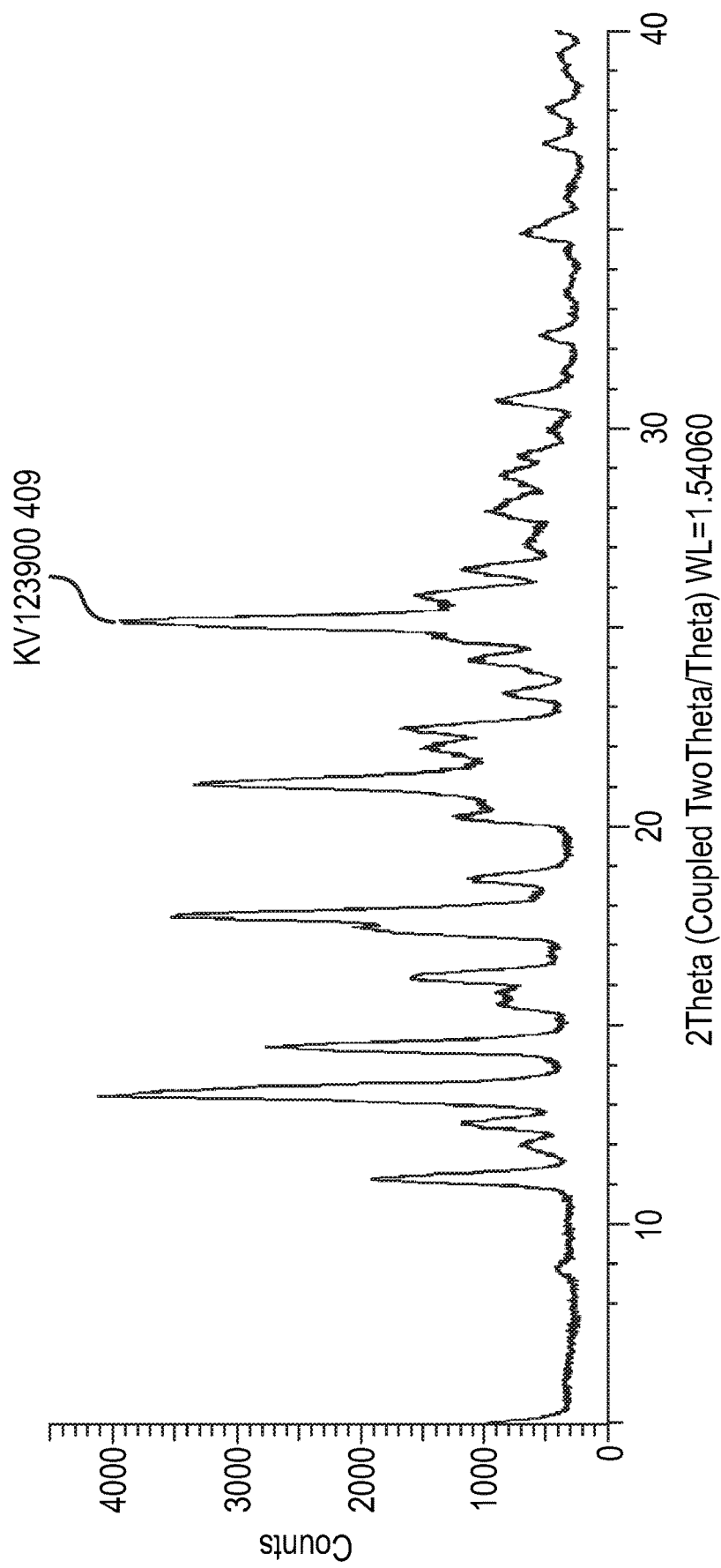

FIG. 2*c*: X-ray powder diffraction pattern of Form 1 of N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide (Example 4).

Figure 3:
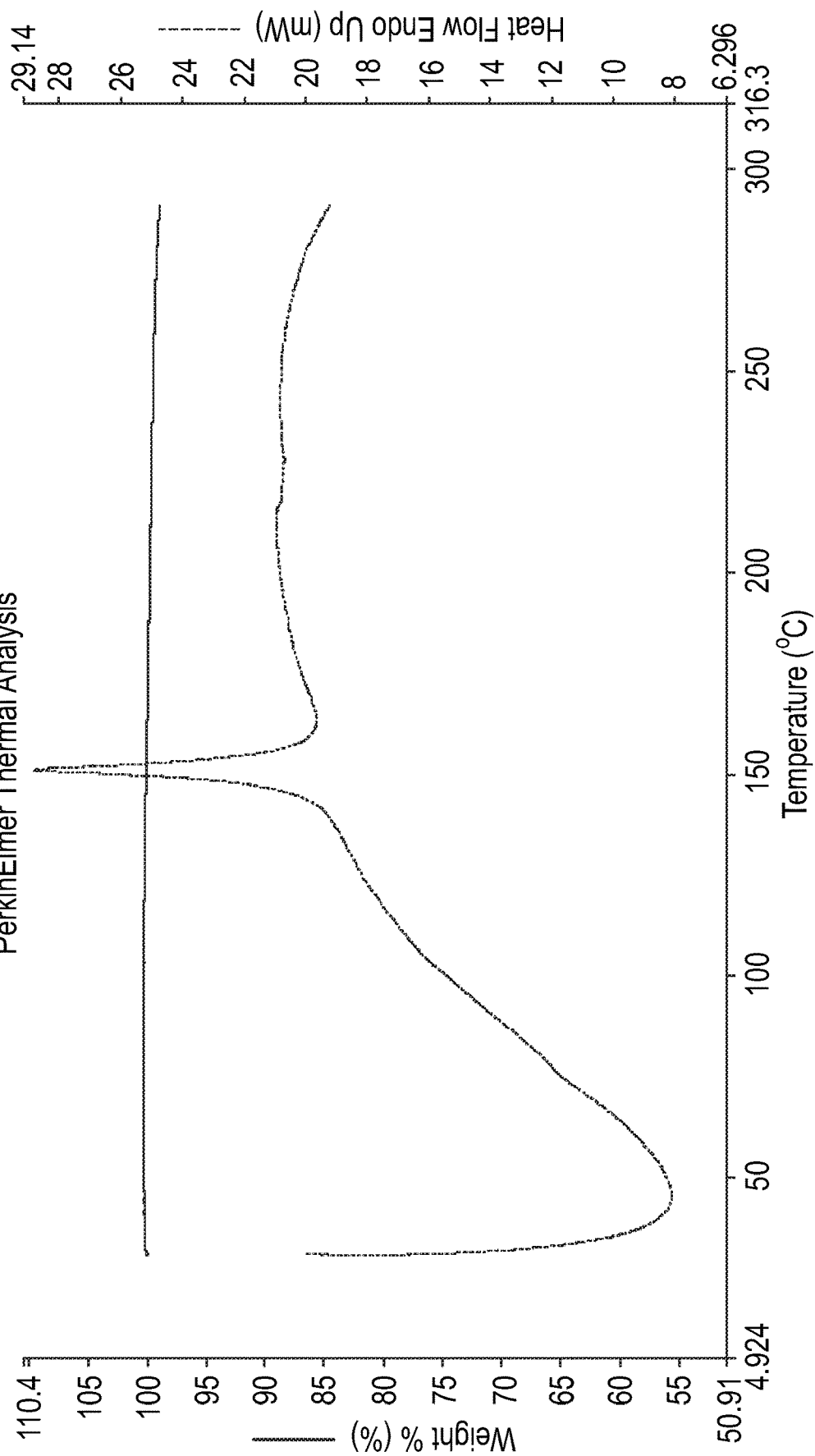

FIG. 3: STA of Form 1 of N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide (Example 2).

FIG. 4: DSC thermograph of Form 1 of N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide (Example 2).

Figure 5:
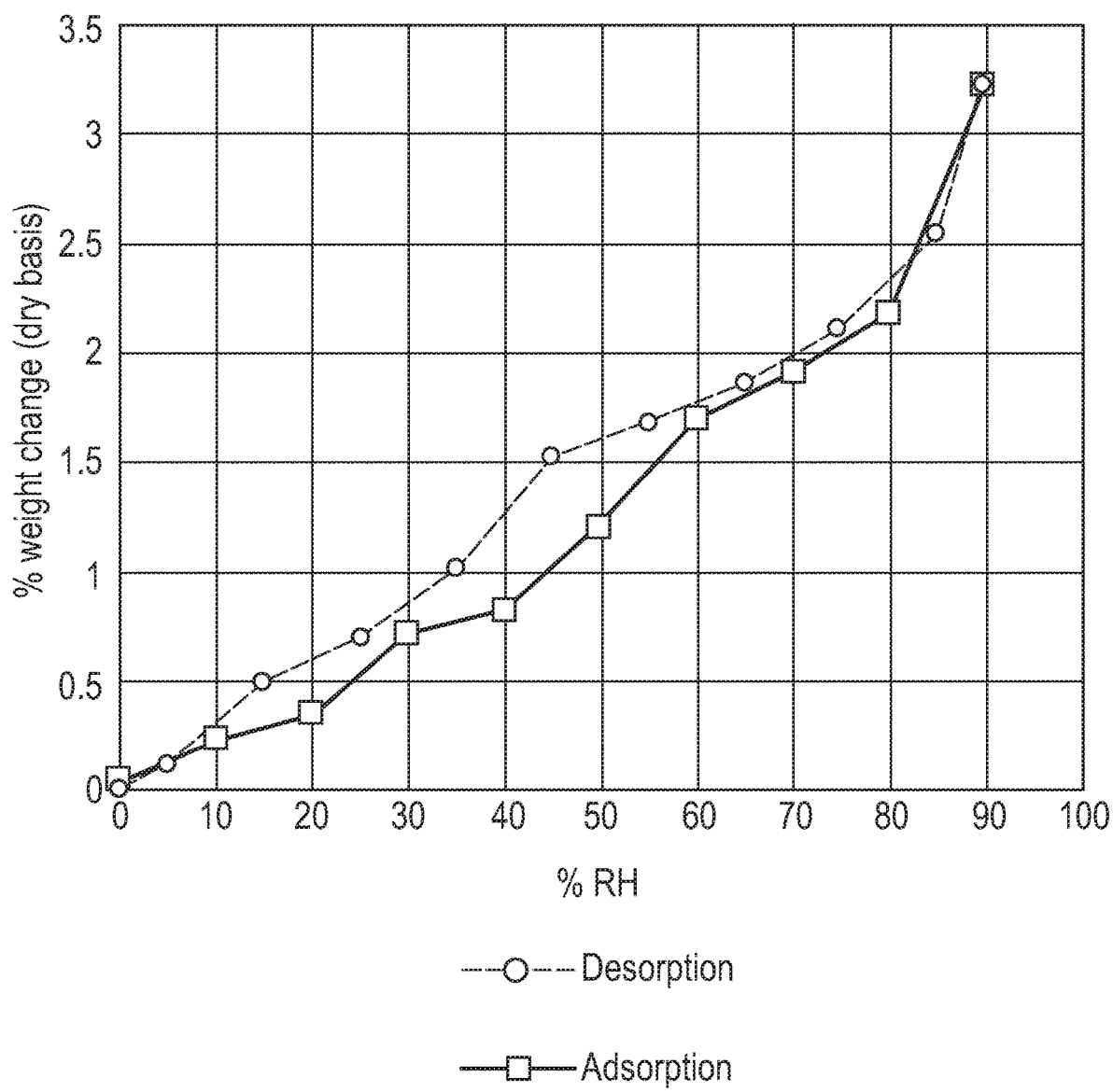

FIG. 5: Gravimetric vapour sorption isotherms (adsorption and desorption) of Form 1 of N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide (Example 2).

Figure 6:
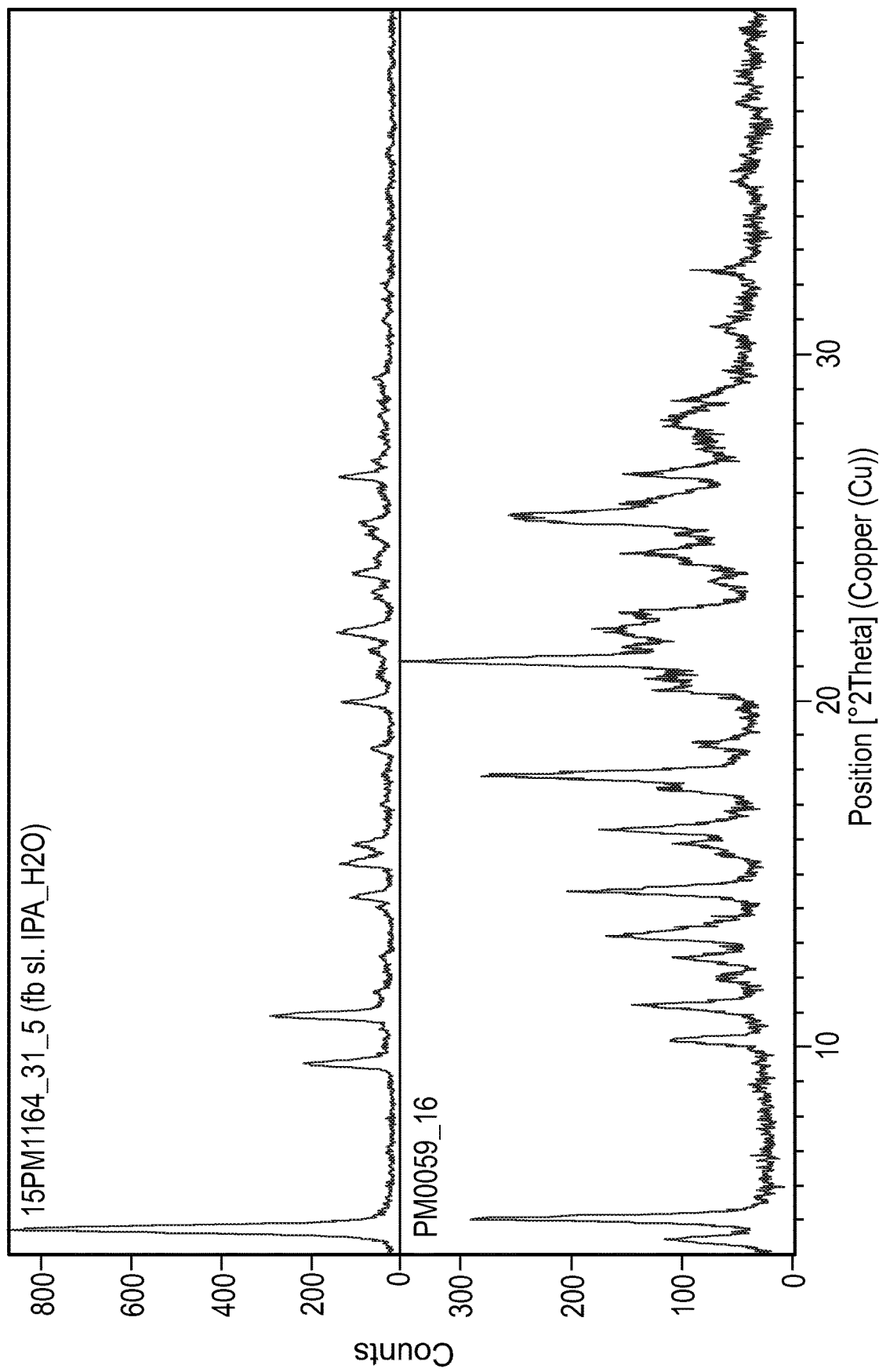

FIG. 6: X-ray powder diffraction pattern (top) of N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide following slurry of Form 1 with 90:10 IPA:water. The bottom X-ray powder diffraction pattern is of Form 1 as a reference (Example 2).

FIG. 7: X-ray powder diffraction pattern of Form 2 of N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide (Example 5).

FIG. 8: X-ray powder diffraction pattern of Form 3 of N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide (Example 6).

FIG. 9: X-ray powder diffraction pattern of Form 4 of N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide (Example 7).

FIG. 10: X-ray powder diffraction pattern of Form 5 of N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide hydrochloride (Example 8).

FIG. 11: X-ray powder diffraction pattern of Form 6 of N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide hydrochloride (Example 9).

FIG. 12: X-ray powder diffraction pattern of Form 7 of N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide hydrochloride (Example 10).

Figure 13:
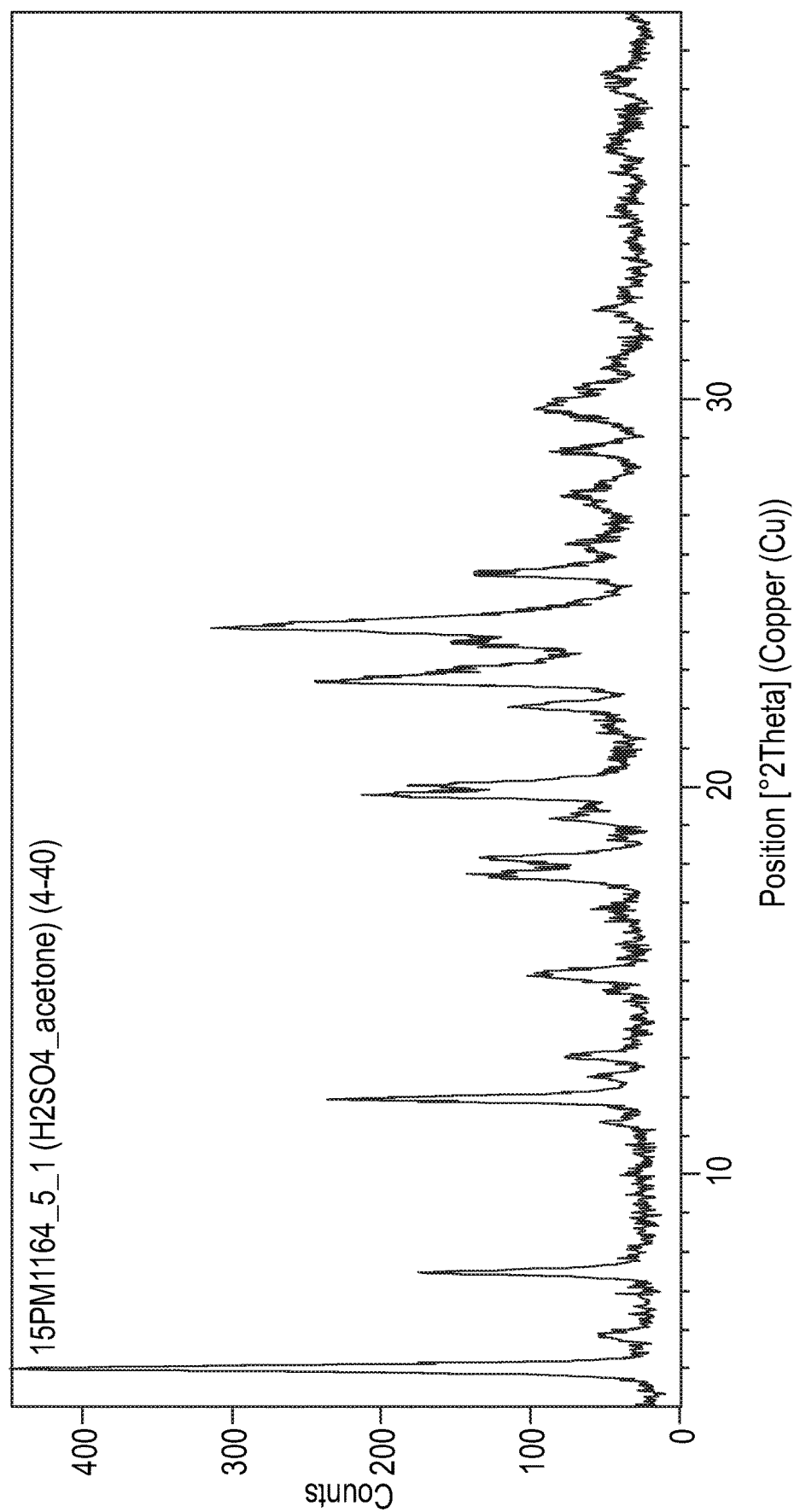

FIG. 13: X-ray powder diffraction pattern of Form 8 of N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide sulfate (Example 11).

FIG. 14: X-ray powder diffraction pattern of Form 9 of N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide phosphate (Example 12).

FIG. 15: X-ray powder diffraction pattern of Form 10 of N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide phosphate (Example 13).

FIG. 16: X-ray powder diffraction pattern of Form 11 of N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide phosphate (Example 14).

FIG. 17: X-ray powder diffraction pattern of Form 12 of N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide mesylate (Example 15).

FIG. 18: X-ray powder diffraction pattern of Form 13 of N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide mesylate (Example 16).

FIG. 19: X-ray powder diffraction pattern of Form 14 of N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide tosylate (Example 17).

FIG. 20: X-ray powder diffraction pattern of Form 15 of N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide edisylate (Example 18).

FIG. 21: X-ray powder diffraction pattern of Form 16 of N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide edisylate (Example 19).

FIG. 22: X-ray powder diffraction pattern of Form 17 of N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide besylate (Example 20).

Figure 23:
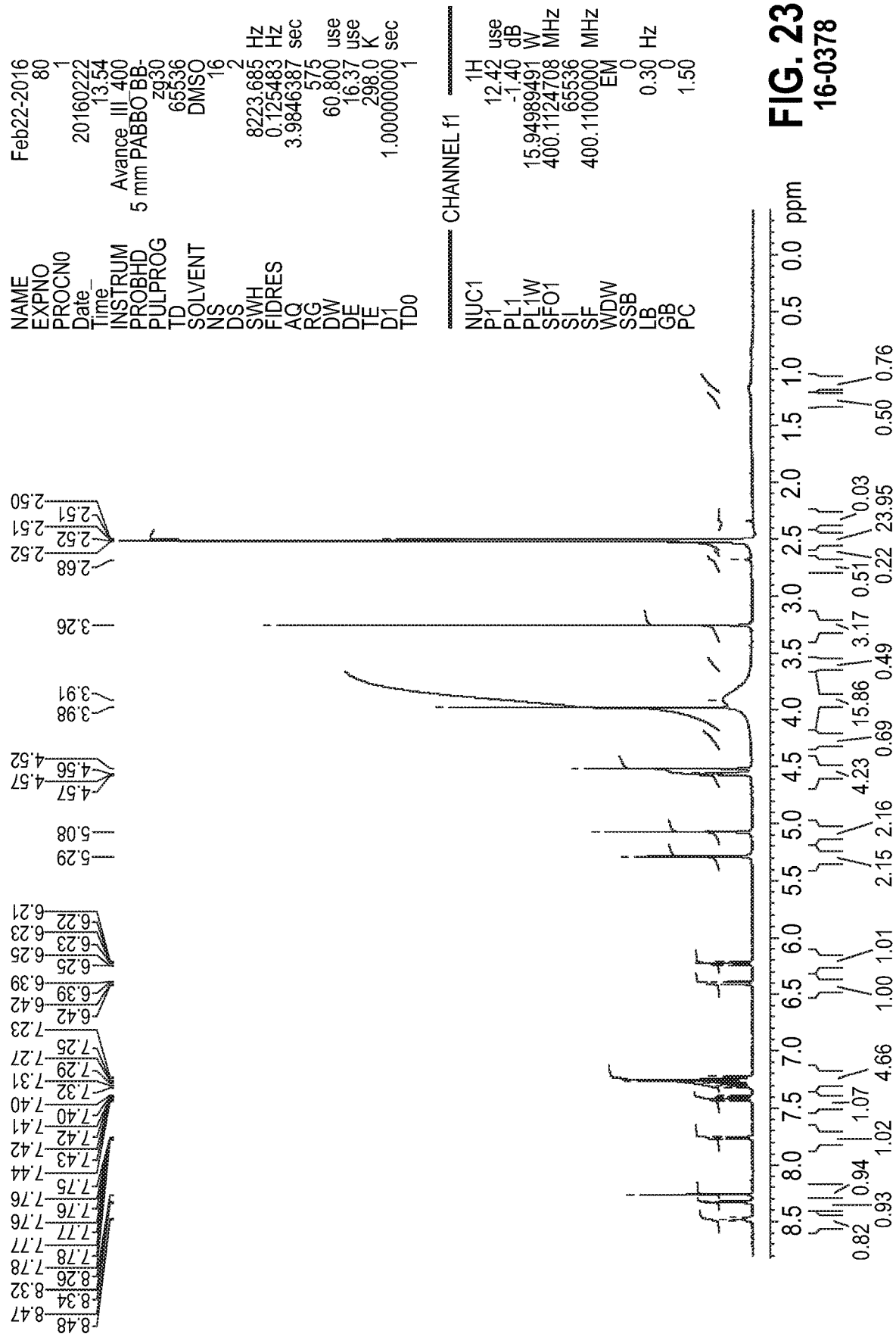

FIG. 23: NMR spectrum of N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide hydrochloride (Example 21).

FIG. 24: X-ray powder diffraction pattern of Form 18 (Example 21) (top) overlaid with Form 5 (Example 8) (bottom) of N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide hydrochloride.

Figure 25:
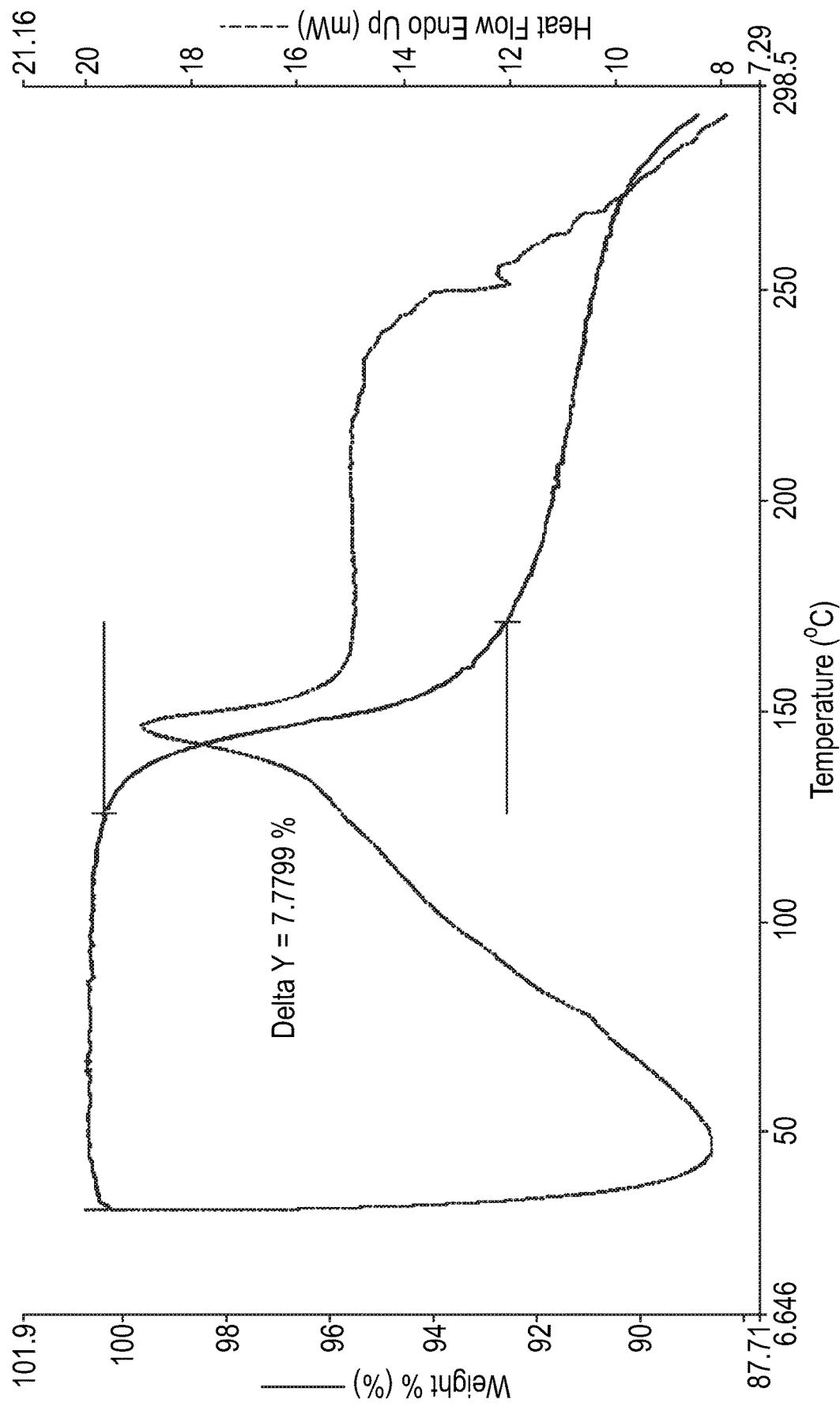

FIG. 25: STA of Form 18 of N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide hydrochloride (Example 21).

FIG. 26: DSC thermograph of Form 18 of N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide hydrochloride (Example 21).

Figure 27:
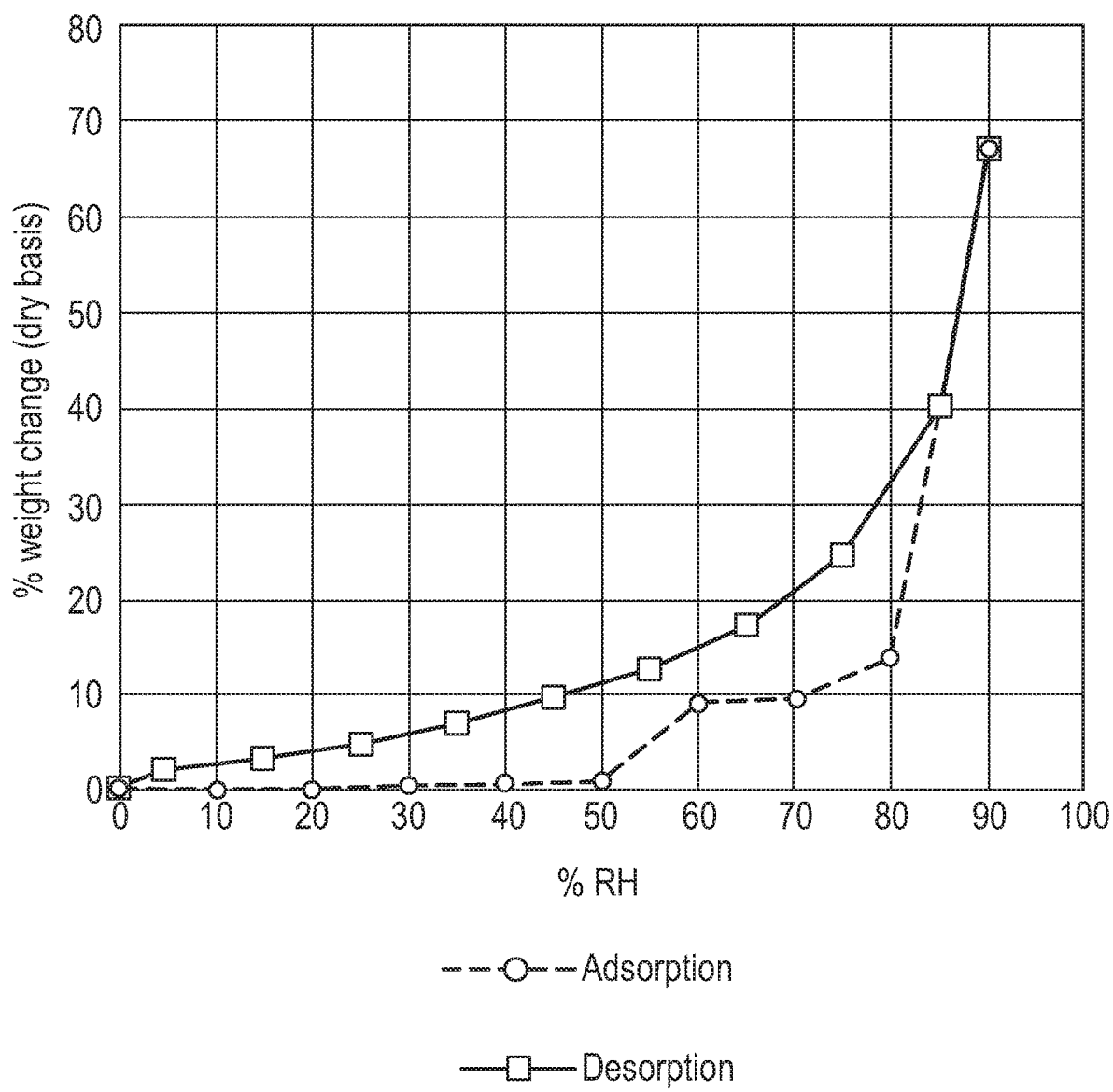

FIG. 27: Gravimetric vapour sorption isotherms (adsorption and desorption) of Form 18 of N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide hydrochloride (Example 21).

Figure 28:
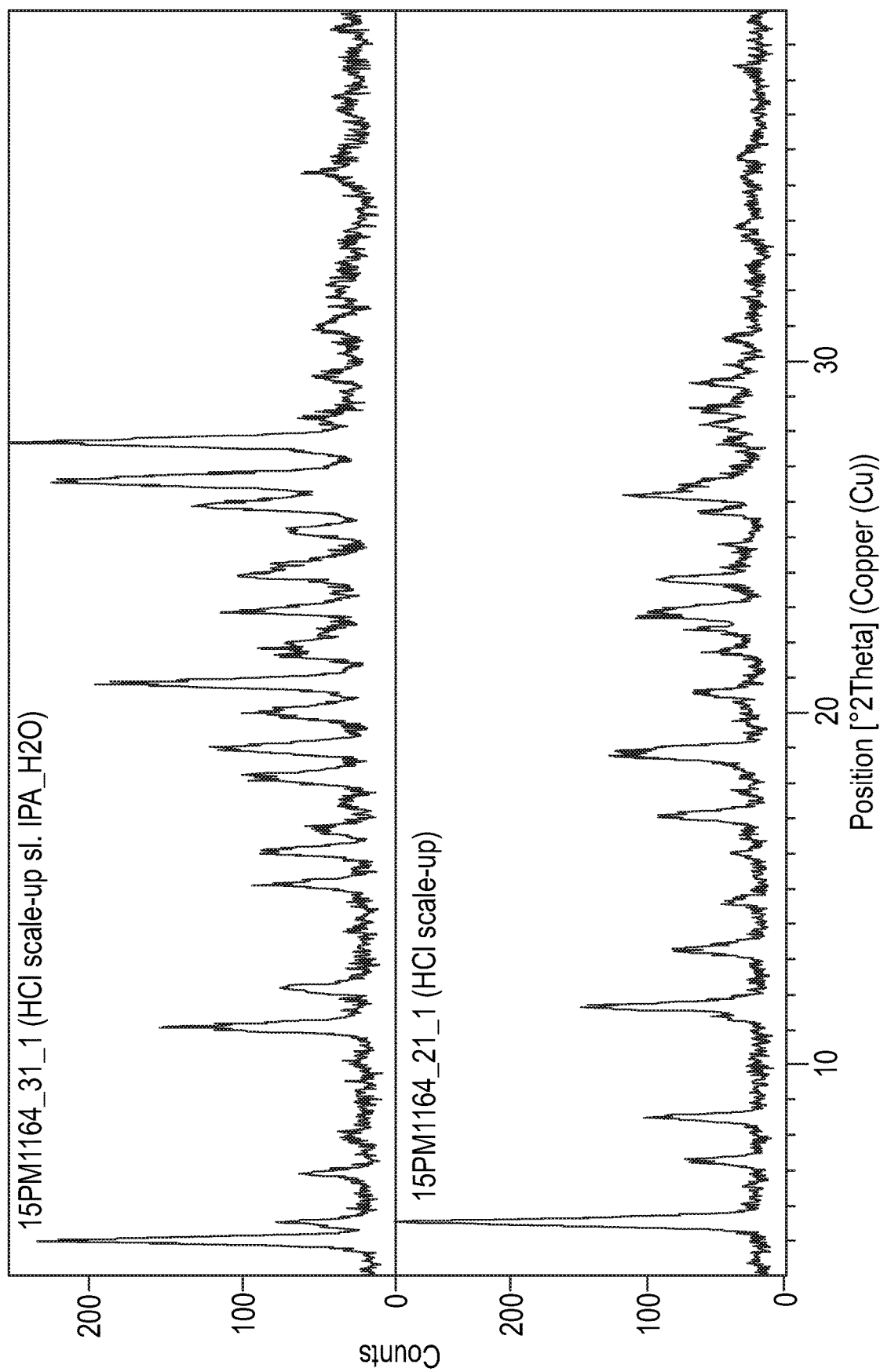

FIG. 28: X-ray powder diffraction pattern (top) of N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide hydrochloride following slurry of Form 18 with 90:10 IPA:water. The bottom X-ray powder diffraction pattern is of Form 18 as a reference (Example 21).

Figure 29:
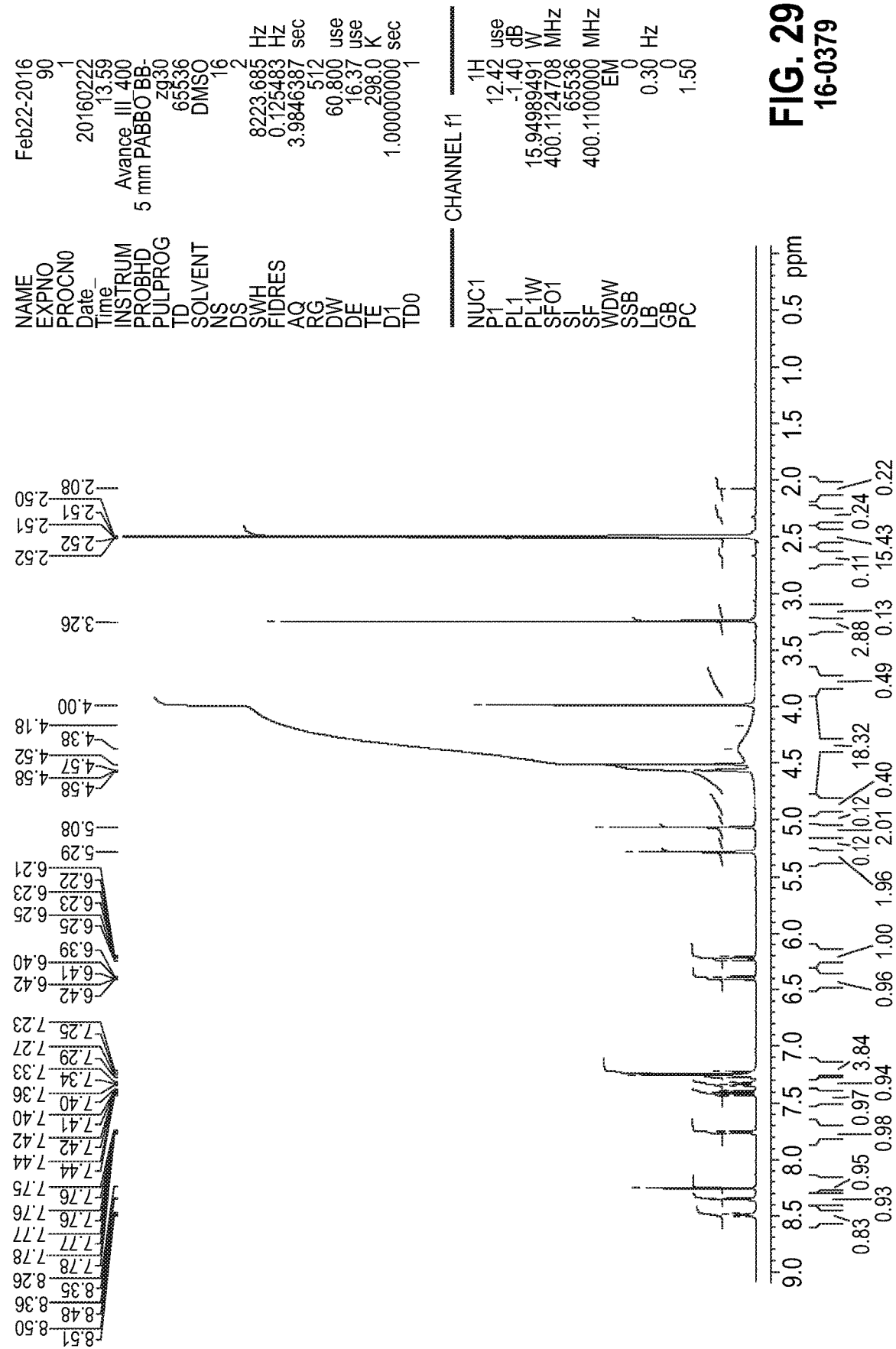

FIG. 29: NMR spectrum of N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide sulfate (Example 22).

Figure 30:
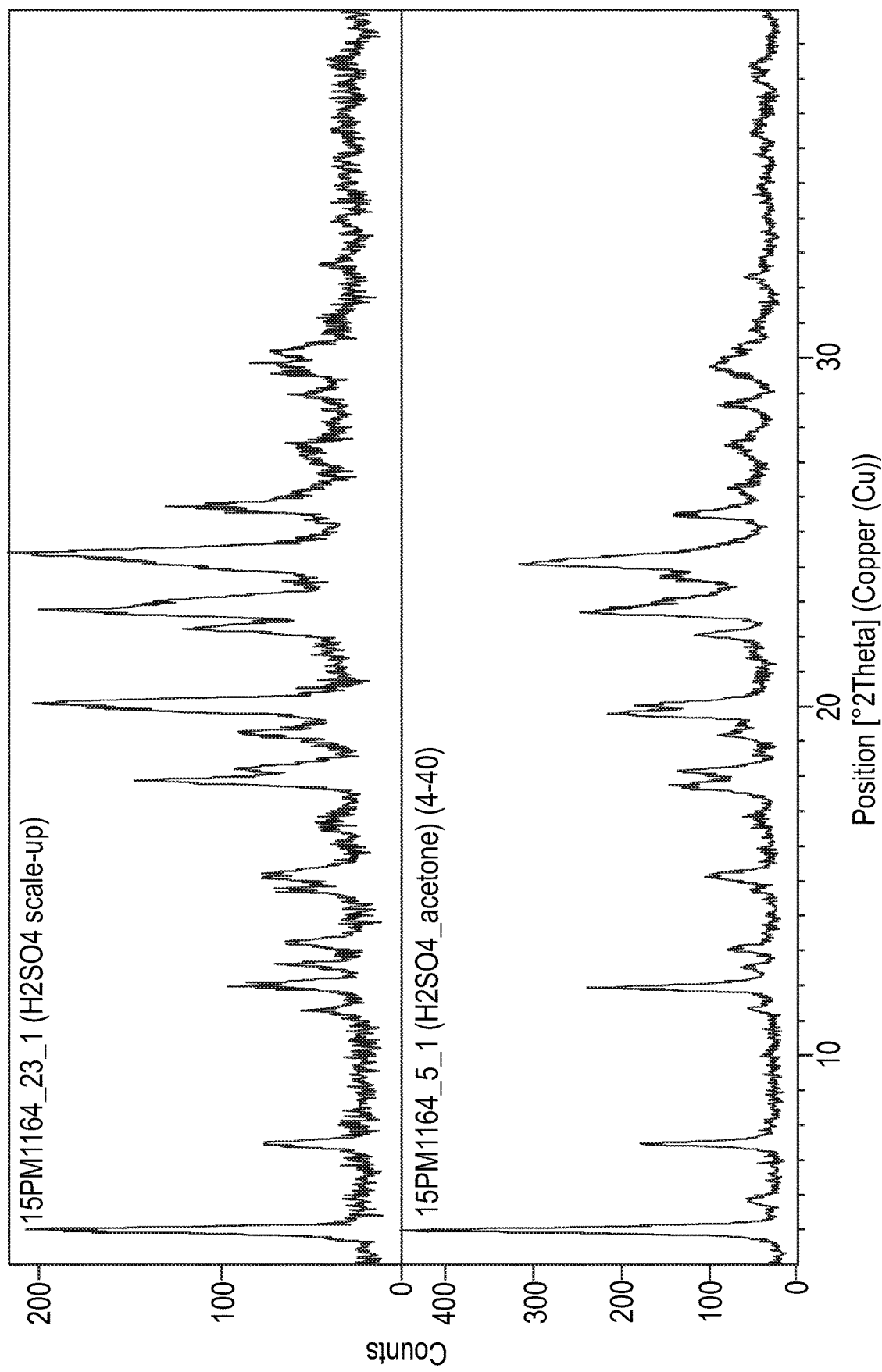

FIG. 30: X-ray powder diffraction pattern of scaled-up Form 8 (Example 22) (top) overlaid with the screening sample of Form 8 (Example 11) (bottom) of N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide sulfate.

Figure 31:
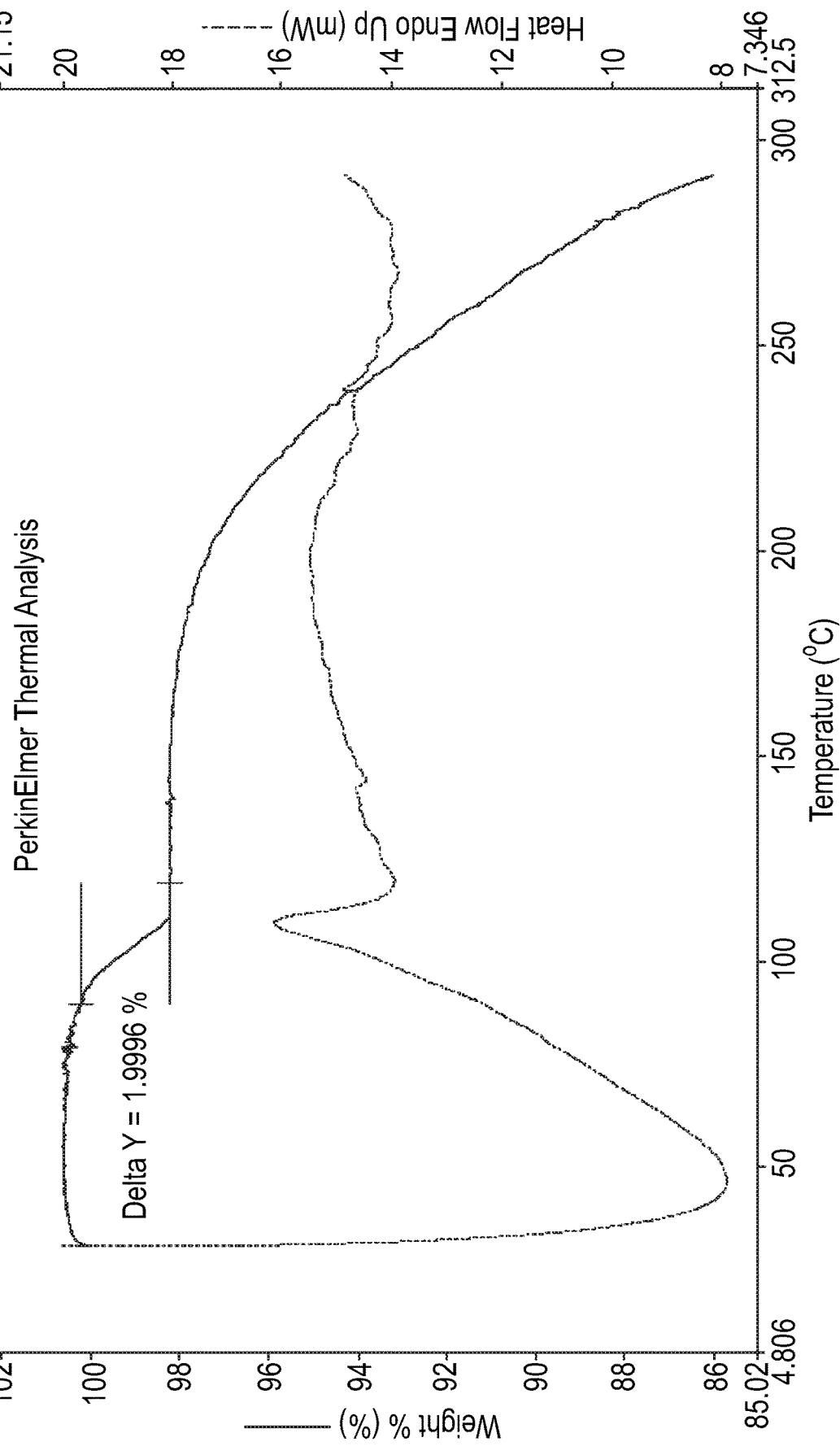

FIG. 31: STA of Form 8 of N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide sulfate (Example 22).

FIG. 32: DSC thermograph of Form 8 of N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide sulfate (Example 22).

Figure 33:
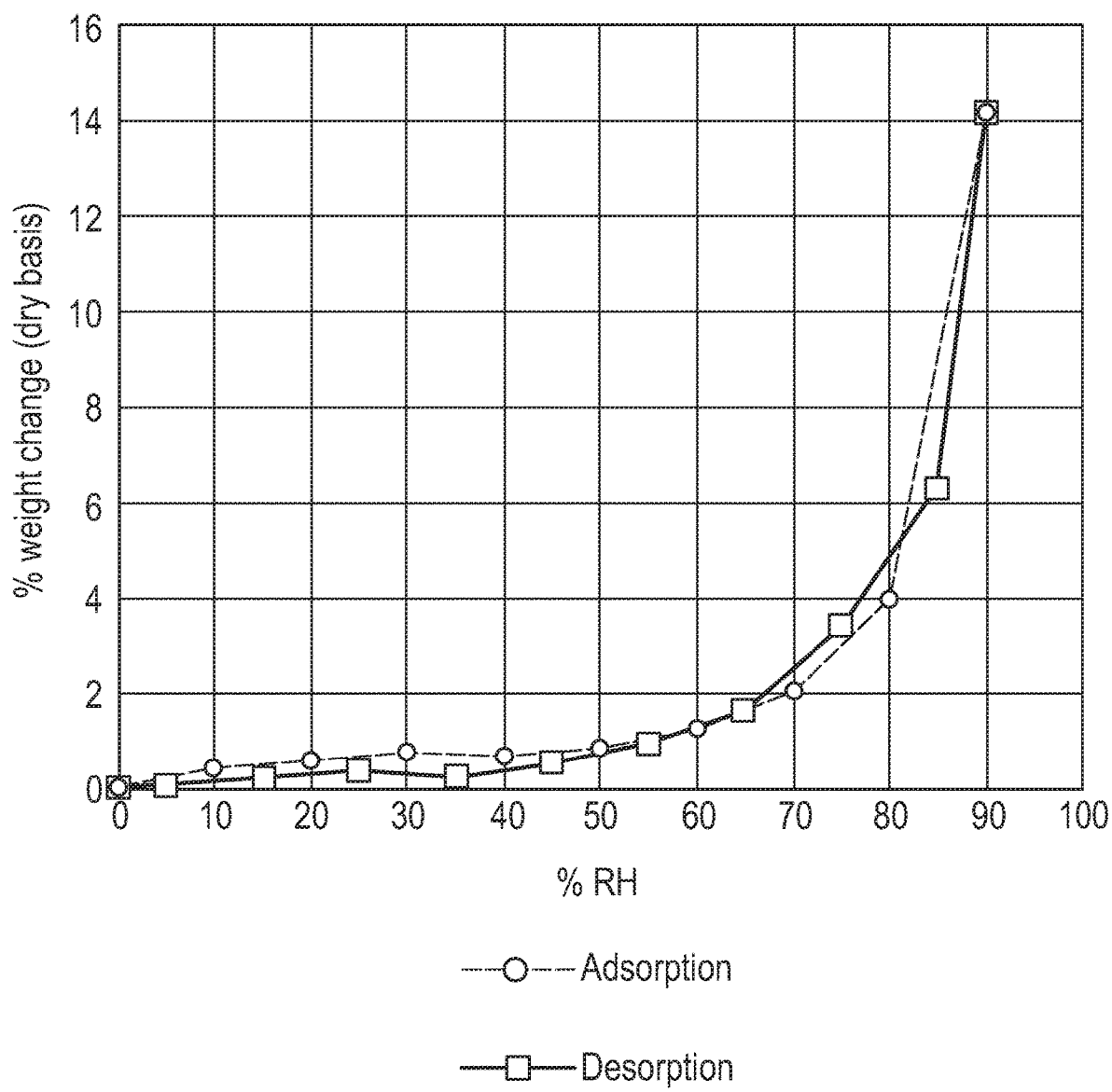

FIG. 33: Gravimetric vapour sorption isotherms (adsorption and desorption) of Form 8 of N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide sulfate (Example 22).

Figure 34:
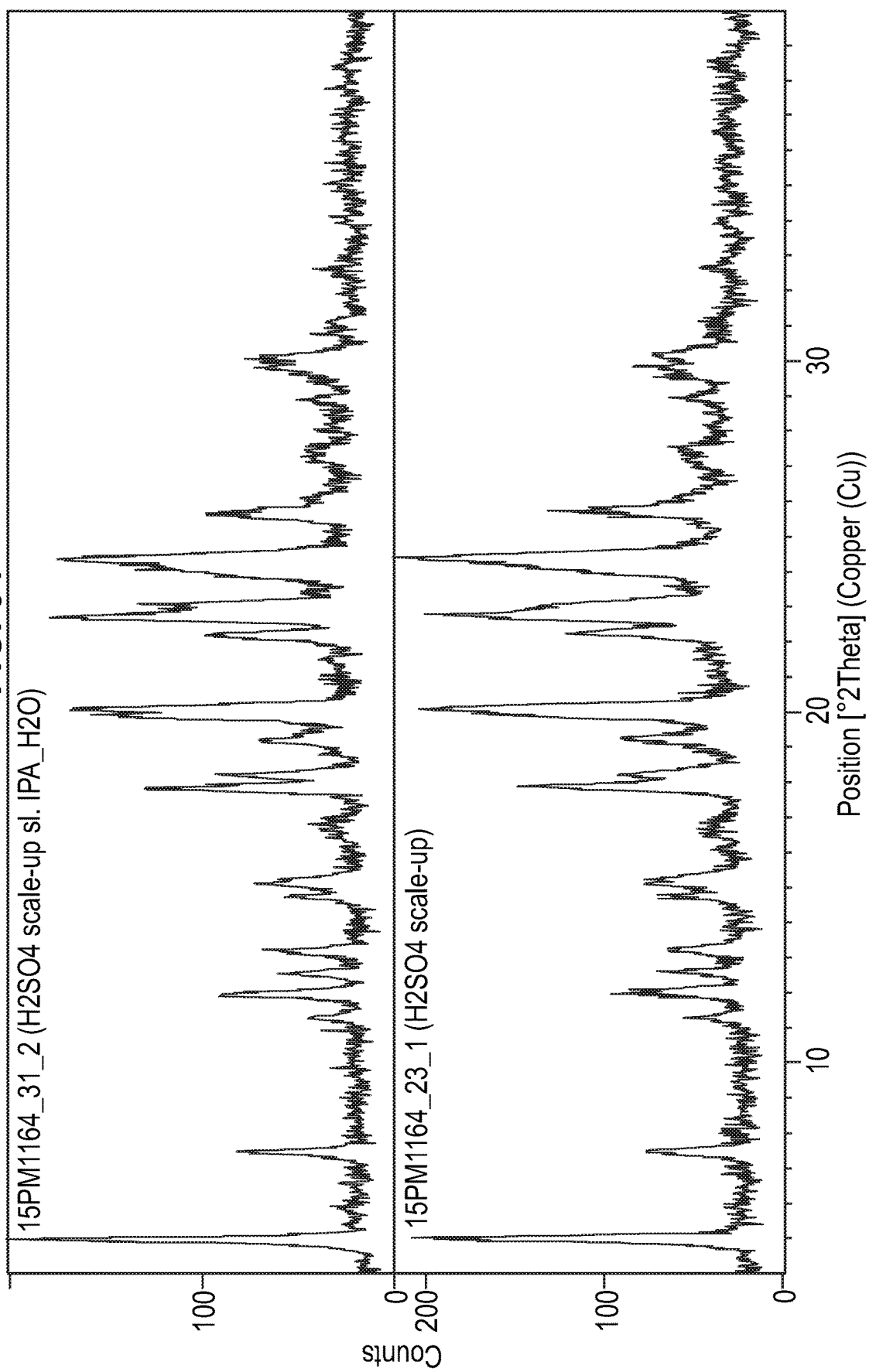

FIG. 34: X-ray powder diffraction pattern (top) of N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide sulfate following slurry of Form 8 with 90:10 IPA:water. The bottom X-ray powder diffraction pattern is of Form 8 as a reference (Example 22).

Figure 35:
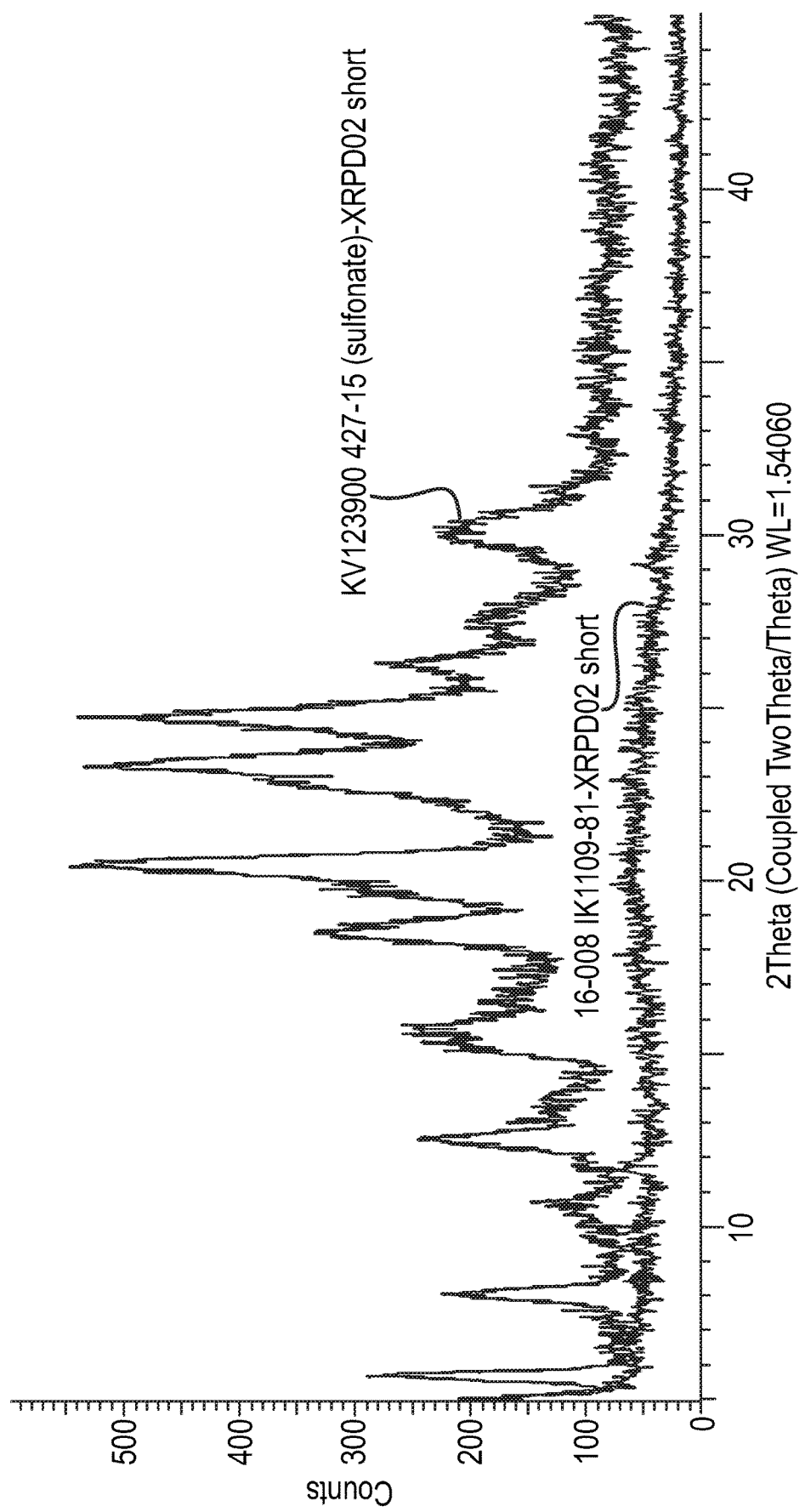

FIG. 35: X-ray powder diffraction pattern of Form 8 of N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide sulfate in Example 23.

Figure 36:
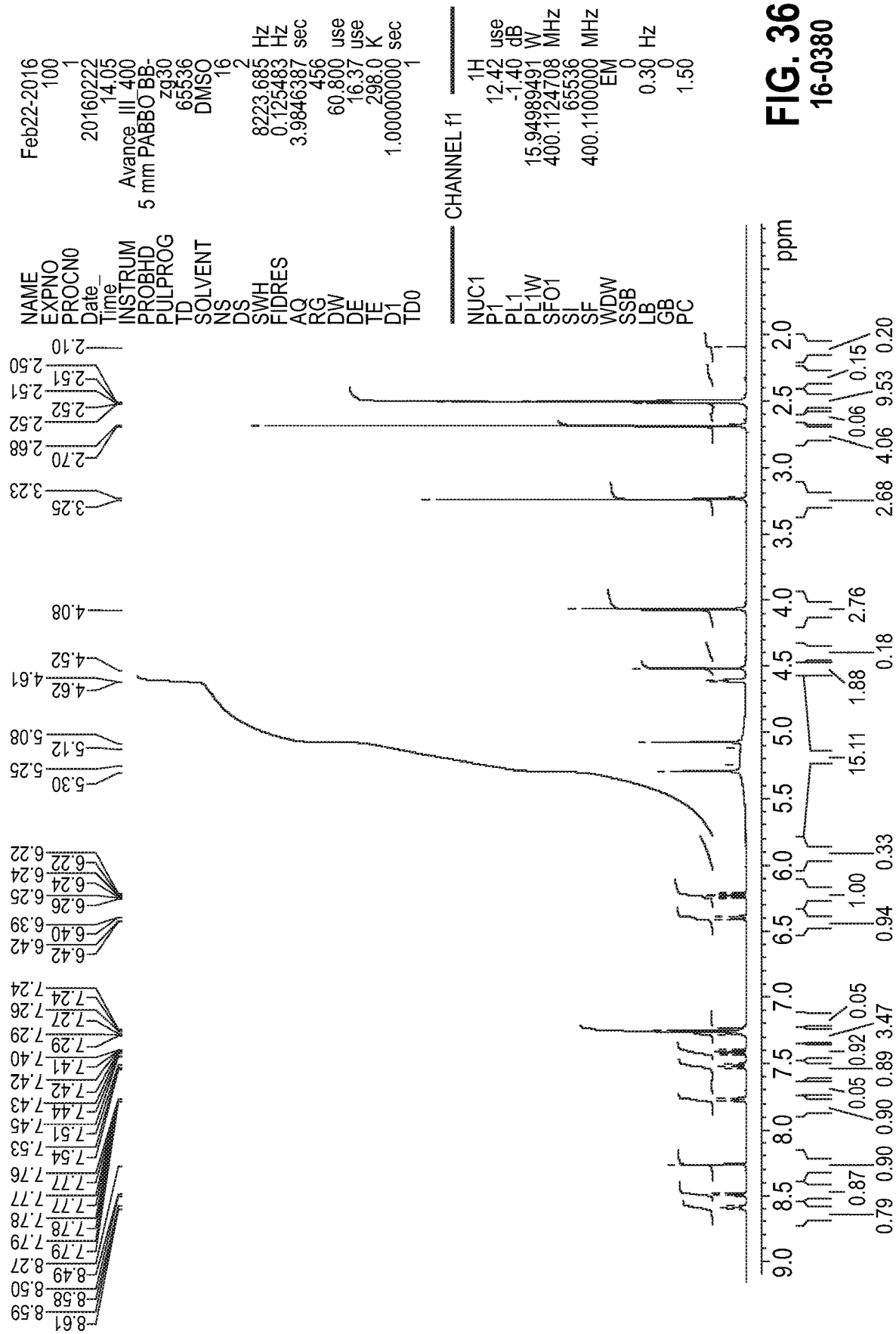

FIG. 36: NMR spectrum of N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide edisylate (Example 24).

FIG. 37: X-ray powder diffraction pattern of scaled-up Form 15 (Example 24) (top) overlaid with the screening sample of Form 15 (Example 18) (bottom) of N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide edisylate.

Figure 38:
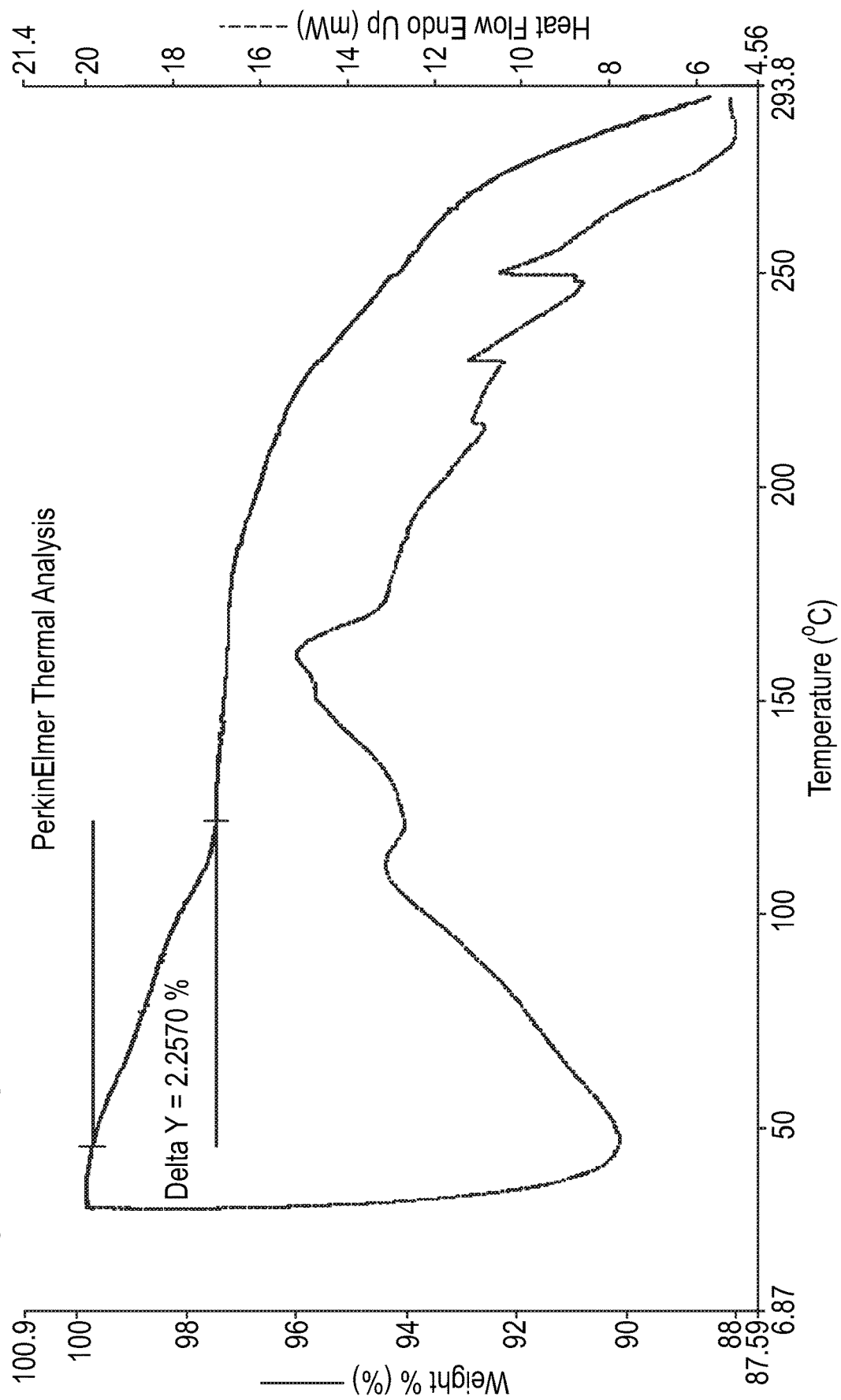

FIG. 38: STA of Form 15 of N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide edisylate (Example 24).

Figure 39:
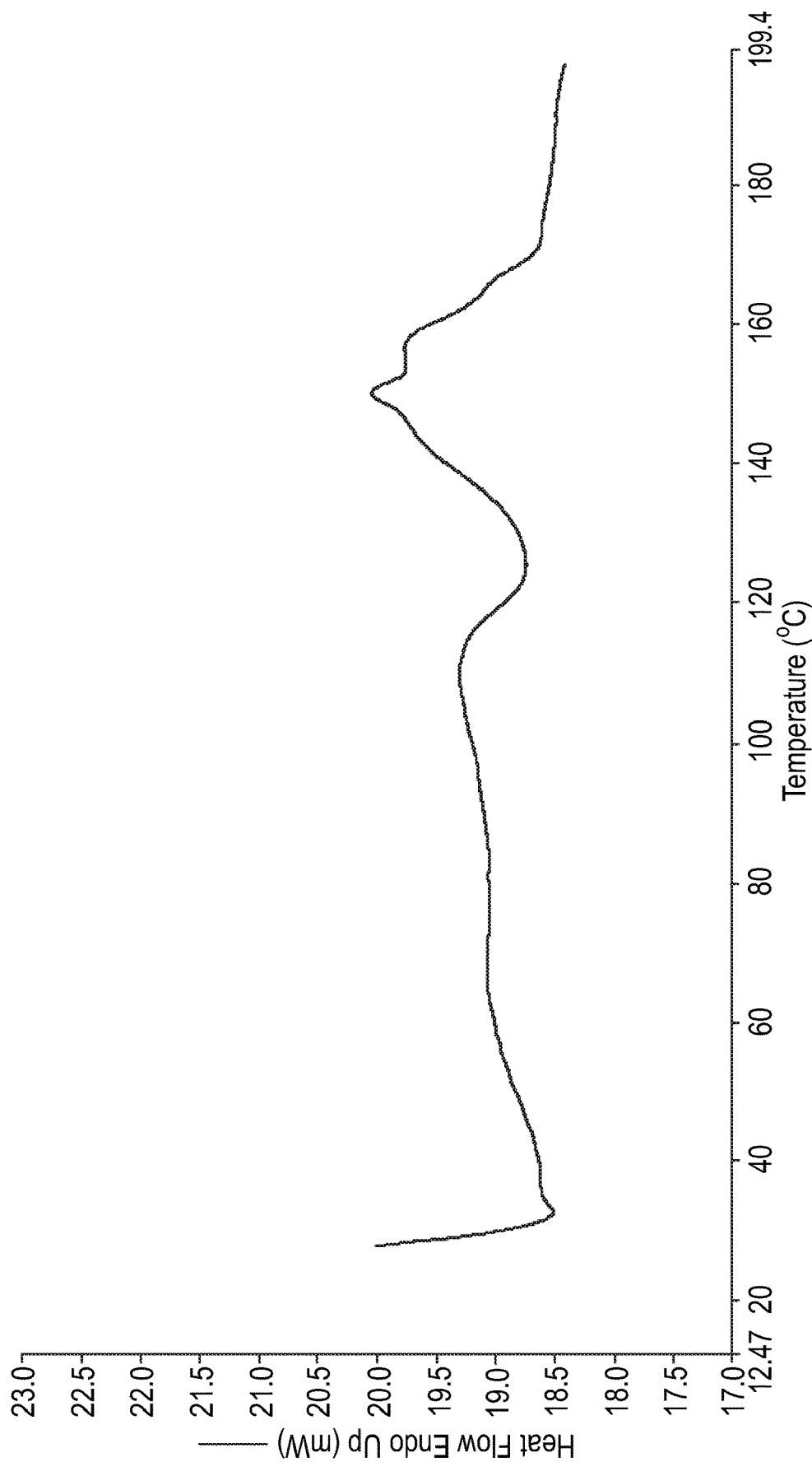

FIG. 39: DSC thermograph of Form 15 of N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide edisylate (Example 24).

Figure 40:
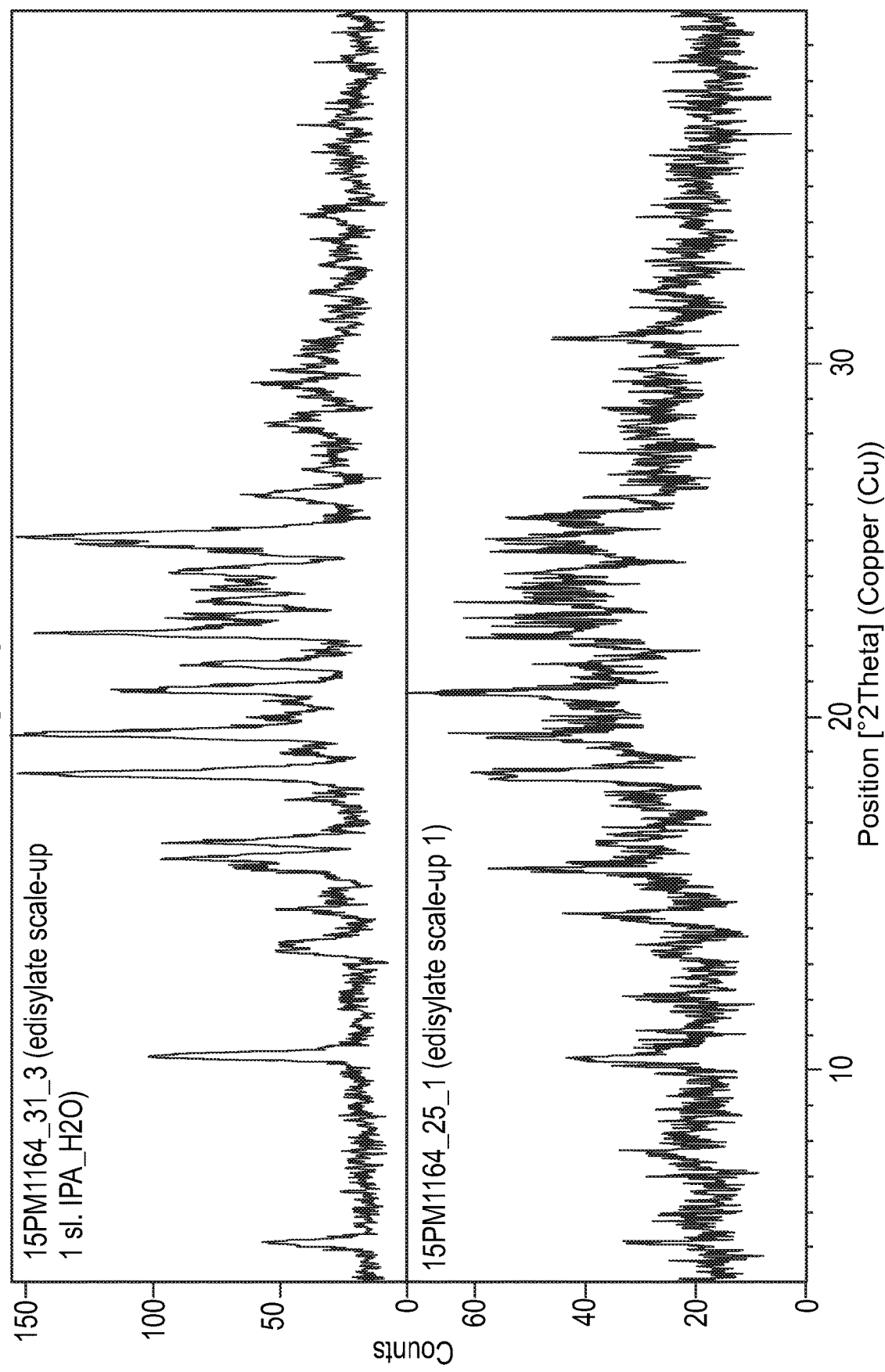

FIG. 40: X-ray powder diffraction pattern (top) of N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide edisylate following slurry of Form 15 with 90:10 IPA:water. The bottom X-ray powder diffraction pattern is of Form 15 as a reference (Example 24).

Figure 41:
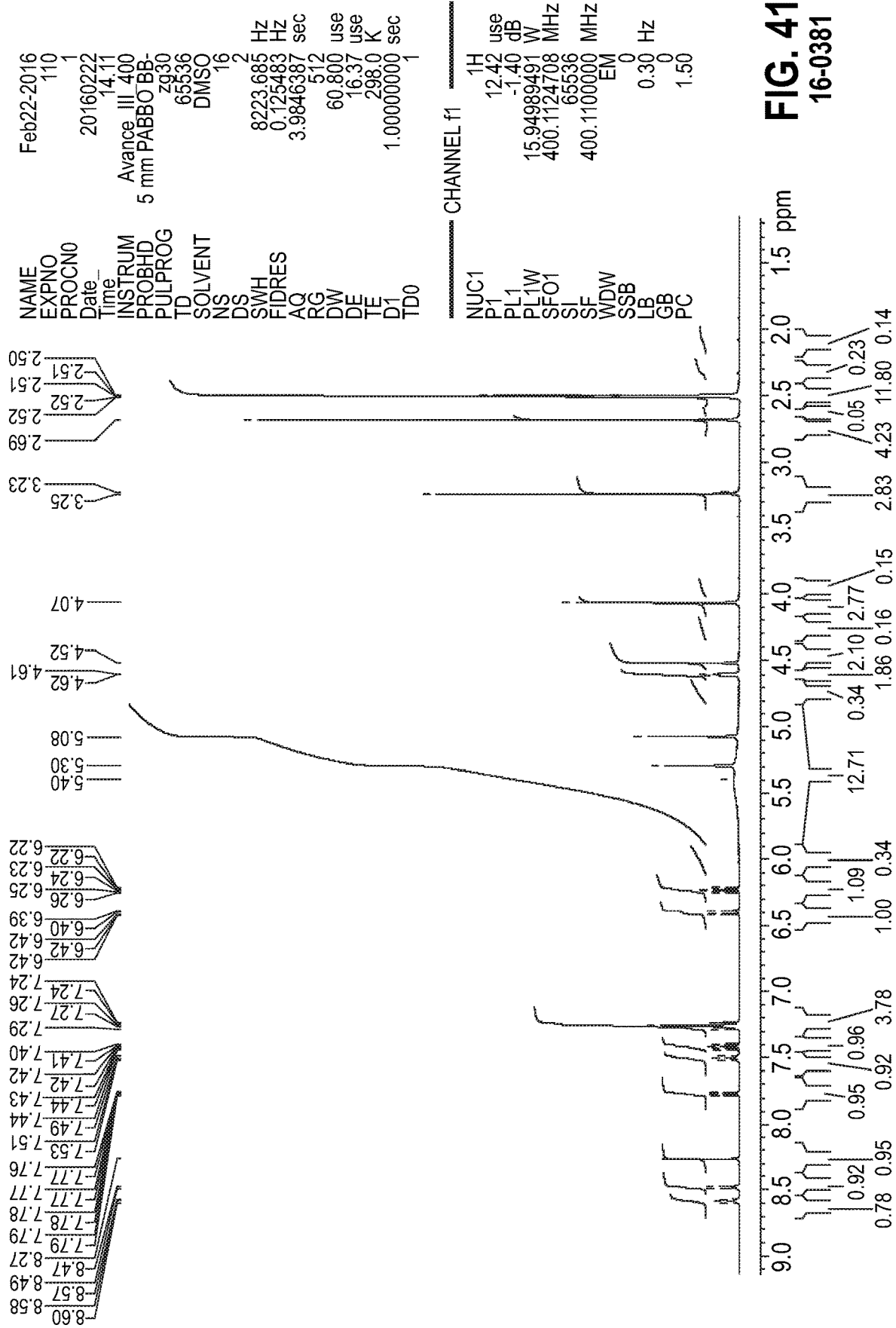

FIG. 41: NMR spectrum of N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide edisylate (Example 25).

FIG. 42: X-ray powder diffraction pattern of scaled-up Form 16 (Example 25) (top) overlaid with the screening sample of Form 16 (Example 19) (bottom) of N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide edisylate.

Figure 43:
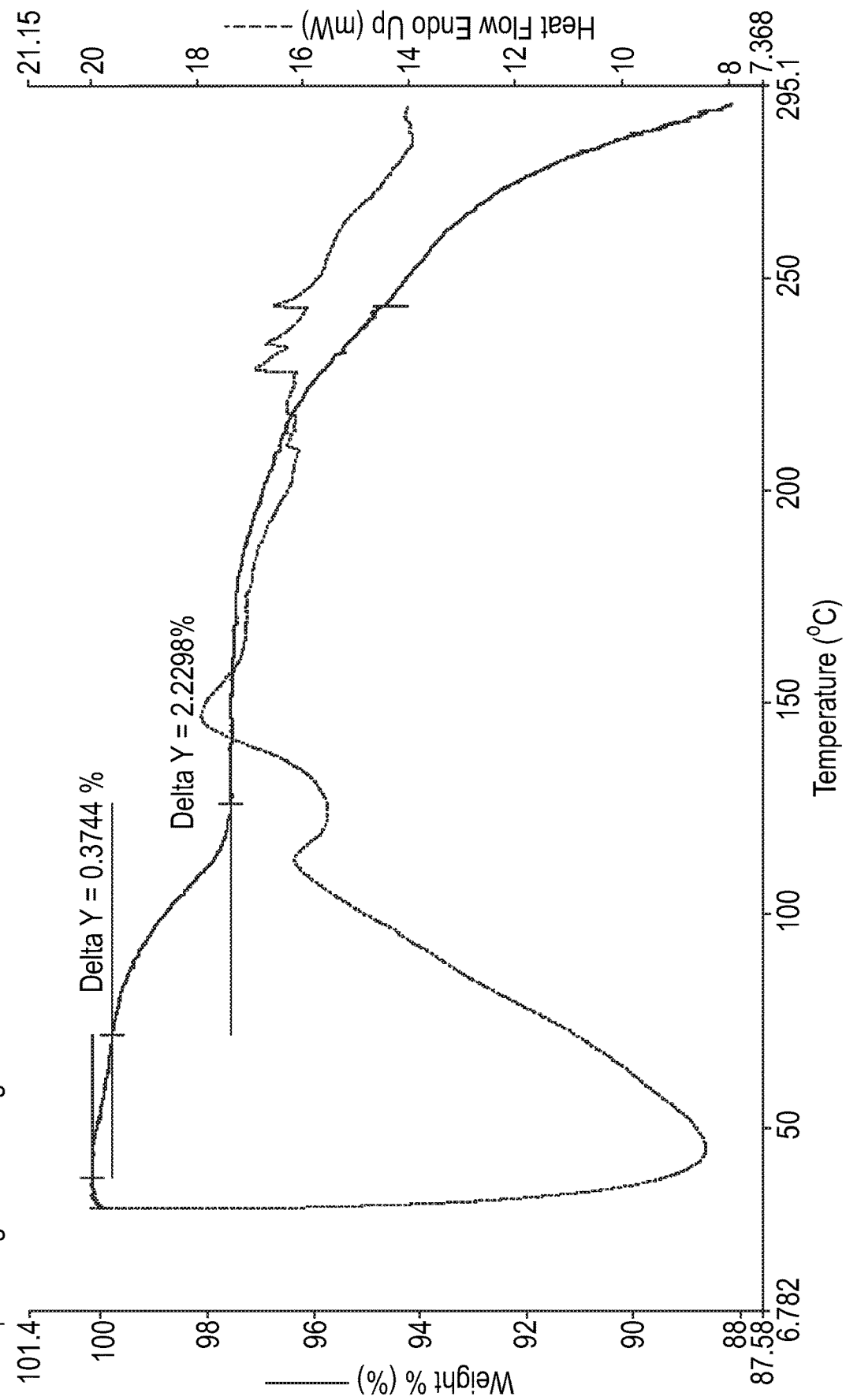

FIG. 43: STA of Form 16 of N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide edisylate (Example 25).

FIG. 44: DSC thermograph of Form 16 of N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide edisylate (Example 25).

Figure 45:
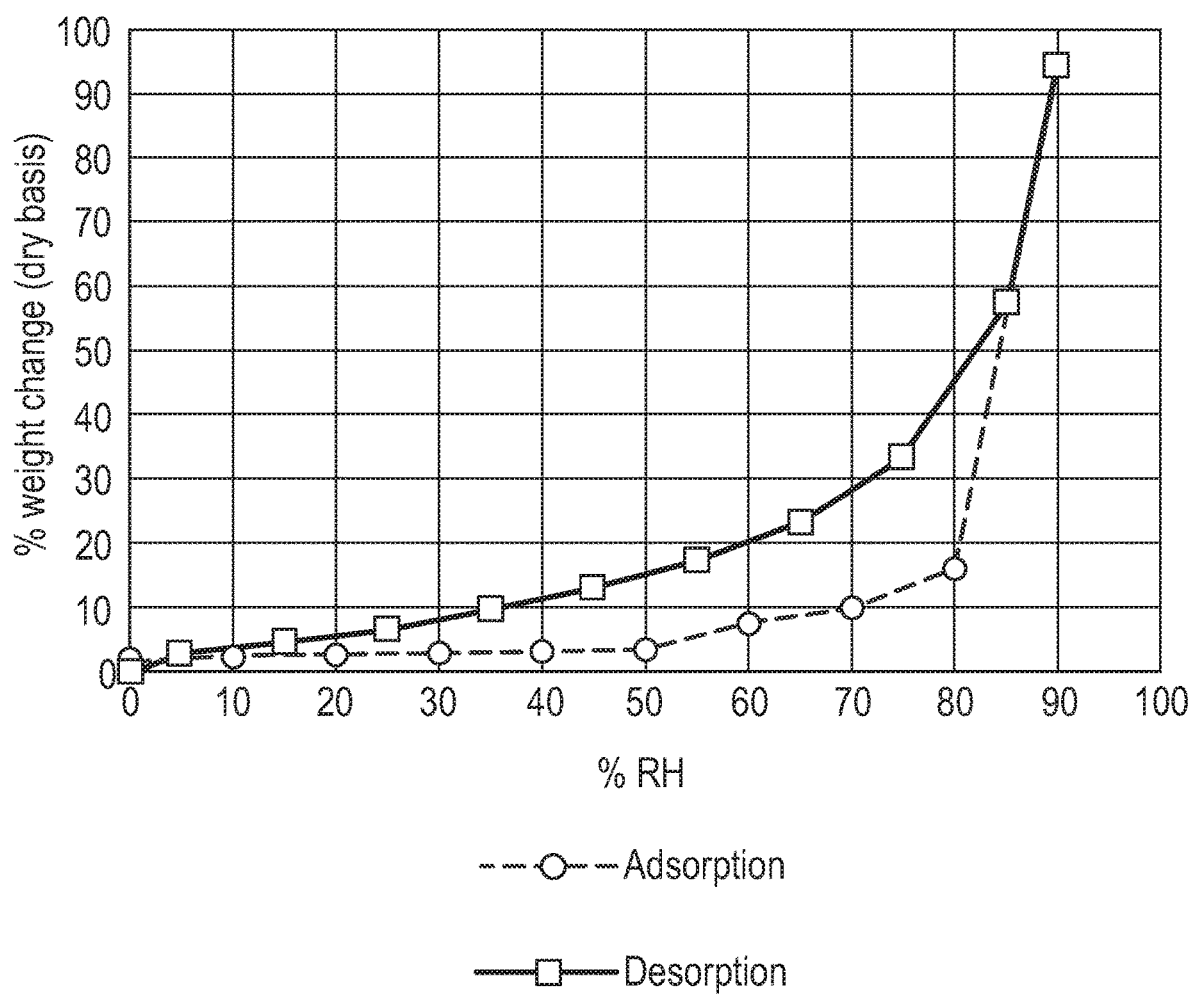

FIG. 45: Gravimetric vapour sorption isotherms (adsorption and desorption) of Form 16 of N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide edisylate (Example 25).

FIG. 46: X-ray powder diffraction patterns of Form 1 of N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide during a 25° C./60% RH stability study at 0 days (top), 1 month (middle) and 3 months (bottom).

FIG. 47: X-ray powder diffraction patterns of Form 1 of N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide during a 40° C./75% RH stability study at 0 days (top), 1 month (middle) and 3 months (bottom).

GENERAL EXPERIMENTAL DETAILS

In the following examples, the following abbreviations and definitions are used:

| | |
|---|---|
| aq | Aqueous solution |
| DCM | Dichloromethane |
| DMF | N,N-Dimethylformamide |
| DMSO | Dimethyl sulfoxide |
| DSC | Differential Scanning Calorimetry |
| EtOAc | Ethyl Acetate |
| HATU | 2-(3H-[1,2,3]triazolo[4,5-b]pyridin-3-yl)-1,1,3,3-tetramethylisouronium hexafluorophosphate(V) |

-continued

| | |
|---|---|
| hrs | Hours |
| HOBt | Hydroxybenzotriazole |
| IPA | 2-Propanol/Propan-2-ol/Iso-propanol |
| LCMS | Liquid chromatography mass spectrometry |
| Me | Methyl |
| MeCN | Acetonitrile |
| MeOH | Methanol |
| min | Minutes |
| MS | Mass spectrum |
| NMR | Nuclear magnetic resonance spectrum - NMR spectra were recorded at a frequency of 400 MHz unless otherwise indicated |
| Pet. Ether | Petroleum ether fraction boiling at 60-80° C. |
| Ph | Phenyl |
| STA | Simultaneous Thermal Analysis |
| SWFI | Sterile water for injection |
| rt | room temperature |
| THF | Tetrahydrofuran |
| TFA | Trifluoroacetic acid |
| XRPD | X-ray powder diffraction |

All reactions were carried out under an atmosphere of nitrogen unless specified otherwise.

$^1$H NMR spectra were recorded on a Bruker (400 MHz) or on a JEOL (40 MHz) spectrometer with reference to deuterium solvent and at rt.

Molecular ions were obtained using LCMS which was carried out using a Chromolith Speedrod RP-18e column, 50×4.6 mm, with a linear gradient 10% to 90% 0.1% $HC_2H$/MeCN into 0.1% $HC_2H/H_2O$ over 13 min, flow rate 1.5 mL/min, or using Agilent, X-Select, acidic, 5-95% MeCN/water over 4 min. Data was collected using a Thermofinnigan Surveyor MSQ mass spectrometer with electospray ionisation in conjunction with a Thermofinnigan Surveyor LC system.

Alternatively, molecular ions were obtained using LCMS which was carried out using an Agilent Poroshell 120 EC-C18 (2.7 m, 3.0×50 mm) column with 0.1% v/v Formic acid in water [eluent A]; MeCN [eluent B]; Flow rate 0.8 mL/min and 1.5 minutes equilibration time between samples, gradient shown below. Mass detection was afforded with API 2000 mass spectrometer (electrospray). Gradient:

| Time (min) | Eluent A (%) | Eluent B (%) |
|---|---|---|
| 0.00 | 95 | 5 |
| 0.20 | 95 | 5 |
| 2.00 | 5 | 95 |
| 3.00 | 5 | 95 |
| 3.25 | 95 | 5 |
| 3.50 | 95 | 5 |

Where products were purified by flash chromatography, 'silica' refers to silica gel for chromatography, 0.035 to 0.070 mm (220 to 440 mesh) (e.g. Merck silica gel 60), and an applied pressure of nitrogen up to 10 p.s.i accelerated column elution. Reverse phase preparative HPLC purifications were carried out using a Waters 2525 binary gradient pumping system at flow rates of typically 20 mL/min using a Waters 2996 photodiode array detector.

All solvents and commercial reagents were used as received.

Chemical names were generated using automated software such as the Autonom software provided as part of the ISIS Draw package from MDL Information Systems or the Chemaxon software provided as a component of MarvinSketch or as a component of the IDBS E-WorkBook.

X-Ray Powder Diffraction patterns were collected on a Philips X-Pert MPD diffractometer and analysed using the following experimental conditions (Method A), unless otherwise specified:

Tube anode: Cu
Generator tension: 40 kV
Tube current: 40 mA
Wavelength alpha1: 1.5406 Å
Wavelength alpha2: 1.5444 Å
Start angle [2θ]: 4
End angle [2θ]: 40
Continuous scan Approximately 2 mg of sample under analysis was gently compressed on the XRPD zero back ground single obliquely cut silica sample holder. The sample was then loaded into the diffractometer for analysis.

Where specified, X-Ray Powder Diffraction patterns were collected using the following method (Method B):

X-ray powder diffraction studies were performed using a Bruker AXS D2 PHASER (D2-205355) in Bragg-Brentano configuration, equipment #2353. A Cu anode at 30 kV, 10 mA, sample stage standard rotating (5/min) with beam stop and monochromatisation by a Kβ-filter (0.59% Ni) are used. The slits that are used are fixed divergence slits 1.0 mm (=0.61°), primary axial Soller slit 2.5° and secondary axial Soller slit 2.5°. The detector is a linear detector LYNXEYE with receiving slit 5° detector opening. The standard sample holder (0.1 mm cavity in (510) silicon wafer) has a minimal contribution to the background signal. The measurement conditions: scan range 5-45° 2θ, sample rotation 5 rpm, 0.5 s/step, 0.010°/step, 3.0 mm detector slit; and all measuring conditions are logged in the instrument control file. The software used for data collection is Diffrac.Commander v4.0. Data analysis is performed using Diffrac.Eva V4.1 evaluation software. No background correction or smoothing is applied to the patterns.

DSC data were collected using the following method: Approximately 5 mg of each sample was weighed into an aluminium DSC pan and sealed non-hermetically with an aluminium lid. The sample was then loaded into a Perkin-Elmer Jade DSC and held at 30° C. Once a stable heat-flow response was obtained, the sample was then heated to a temperature between 200 and 300° C. at a scan rate of 10° C./min and the resulting heat flow response was monitored. A 20 cm$^3$/min helium purge was used. Prior to analysis, the instrument was temperature and heat flow verified using an indium standard.

Gravimetric Vapour Sorption (GVS) data were collected using the following method: Approximately 10 mg of sample was placed into a wire-mesh vapour sorption balance pan and loaded into an 'IgaSorp' vapour sorption balance (Hiden Analytical Instruments). The sample was then dried by maintaining a 0% humidity environment until no further weight change was recorded. Subsequently, the sample was then subjected to a ramping profile from 0-90% RH at 10% RH increments, maintaining the sample at each step until equilibration had been attained (99% step completion). Upon reaching equilibration, the % RH within the apparatus was ramped to the next step and the equilibration procedure repeated. After completion of the sorption cycle, the sample was then dried using the same procedure. The weight change during the sorption/desorption cycles were then monitored, allowing for the hygroscopic nature of the sample to be determined.

Simultaneous Thermal Analysis (STA) data were collected using the following method: Approximately 5 mg of sample was accurately weighed into a ceramic crucible and

SYNTHETIC EXAMPLES

Example 1

A. 1-(4-Hydroxymethyl-benzyl)-1H-pyridin-2-one 4-(Chloromethyl)benzylalcohol (5.0 g, 31.93 mmol) was dissolved in acetone (150 mL). 2-hydroxypyridine (3.64 g, 38.3 mmol) and potassium carbonate (13.24 g, 95.78 mmol) were added and the reaction mixture was stirred at 50° C. for 3 hrs after which time the solvent was removed in vacuo and the residue taken up in chloroform (100 mL). This solution was washed with water (30 mL), brine (30 mL), dried ($Na_2SO_4$) and evaporated in vacuo. The residue was purified by flash chromatography (silica), eluent 3% MeOH/97% $CHCl_3$, to give a white solid identified as 1-(4-hydroxymethyl-benzyl)-1H-pyridin-2-one (5.30 g, 24.62 mmol, 77% yield).

$[M+Na]^+=238$

B. 1-(4-Chloromethyl-benzyl)-1H-pyridin-2-one 1-(4-Hydroxymethyl-benzyl)-1H-pyridin-2-one (8.45 g, 39.3 mmol), dry DCM (80 mL) and triethylamine (7.66 ml, 55.0 mmol) were cooled in an ice bath. Methanesulfonyl chloride (3.95 ml, 51.0 mmol) was added and stirred in ice bath for 15 min. The ice bath was removed and stirring continued at rt temperature overnight. The reaction mixture was partitioned between DCM (100 mL) and saturated aqueous $NH_4Cl$ solution (100 mL). The aqueous layer was extracted with further DCM (2×50 mL) and the combined organics washed with brine (50 mL), dried over $Na_2SO_4$, filtered and concentrated to give 1-(4-chloromethyl-benzyl)-1H-pyridin-2-one (8.65 g, 36.6 mmol, 93% yield) as a pale yellow solid.

$[MH]^+=234.1$

C. Methyl 3-(methoxymethyl)-1-(4-((2-oxopyridin-1(2H)-yl)methyl)benzyl)-1H-pyrazole-4-carboxylate Potassium carbonate (519 mg, 3.76 mmol) was added to a solution of methyl 3-(methoxymethyl)-1H-pyrazole-4-carboxylate (320 mg, 1.88 mmol; CAS no. 318496-66-1 (synthesised according to the method described in WO 2012/009009)) and 1-(4-(chloromethyl)benzyl)pyridin-2(1H)-one (527 mg, 2.26 mmol) in DMF (5 mL) and heated at 60° C. overnight. The reaction mixture was diluted with EtOAc (50 mL) and washed with brine (2×100 mL), dried over magnesium sulfate, filtered and reduced in vacuo. The crude product was purified by flash chromatography (40 g column, 0-100% EtOAc in isohexanes) to afford two regioisomers. The second isomer off the column was collected to afford methyl 3-(methoxymethyl)-1-(4-((2-oxopyridin-1(2H)-yl)methyl)benzyl)-1H-pyrazole-4-carboxylate (378 mg, 1.01 mmol, 53.7% yield) as a colourless gum.

$[MH]^+=368.2$

D. 3-(Methoxymethyl)-1-(4-((2-oxopyridin-1(2H)-yl)methyl)benzyl)-1H-pyrazole-4-carboxylic Acid To methyl 3-(methoxymethyl)-1-(4-((2-oxopyridin-1(2H)-yl)methyl)benzyl)-1H-pyrazole-4-carboxylate (3.77 g, 10.26 mmol) in THF (5 mL) and MeOH (5 mL) was added 2M NaOH solution (15.39 ml, 30.8 mmol) and stirred at rt overnight. 1M HCl (50 mL) was added and extracted with EtOAc (50 mL). The organic layer was washed with brine (50 mL), dried over magnesium sulfate, filtered and reduced in vacuo to give 3-(methoxymethyl)-1-(4-((2-oxopyridin-1 (2H)-yl)methyl)benzyl)-1H-pyrazole-4-carboxylic acid (1.22 g, 3.45 mmol, 33.6% yield) as a white powder.

$[MH]^+=354.2$

E. 3-Fluoro-4-methoxy-pyridine-2-carbonitrile

To a large microwave vial, copper (1) cyanide (1.304 g, 14.56 mmol) was added to a solution of 2-bromo-3-fluoro-4-methoxypyridine (1 g, 4.85 mmol) in DMF (5 mL). The reaction vial was sealed and heated to 100° C. for 16 hrs. The reaction mixture was diluted with water (20 mL) and EtOAc (20 mL). The thick suspension was sonicated and required additional water (40 mL) and EtOAc (2×50 mL) with sonication to break-up the solid precipitated. The combined layers were filtered through a plug of celite and the organic layer isolated, washed with brine (50 mL), dried over magnesium sulfate, filtered and the solvent removed under reduced pressure to give a pale green solid identified as the desired compound 3-fluoro-4-methoxy-pyridine-2-carbonitrile (100 mg, 0.578 mmol, 12% yield)

F. (3-Fluoro-4-methoxy-pyridin-2-ylmethyl)-carbamic Acid Tert-Butyl Ester

3-Fluoro-4-methoxy-pyridine-2-carbonitrile (100 mg, 0.578 mmol) was dissolved in anhydrous methanol (10 mL, 247 mmol) and nickel chloride hexahydrate (14 mg, 0.058 mmol) was added followed by di-tert-butyl dicarbonate (255 mg, 1.157 mmol). The resulting pale green solution was cooled in an ice-salt bath to −5° C. and then sodium borohydride (153 mg, 4.05 mmol) was added portionwise maintaining the reaction temperature 0° C. The deep brown solution was left to stir at 0° C. and slowly allowed to warm to rt and then left to stir at rt for 3 hrs. The reaction mixture was evaporated to dryness at 40° C. to afford a black residue which was diluted with DCM (10 mL) and washed with sodium hydrogen carbonate (10 mL). An emulsion formed so the organics were separated via a phase separating cartridge and concentrated. The crude liquid was purified by chromatography eluting with EtOAc/iso-Hexane to afford the title compound, (3-fluoro-4-methoxy-pyridin-2-ylmethyl)-carbamic acid tert-butyl ester as a clear yellow oil (108 mg, 62% yield)

$[MH]^+=257$

G. C-(3-Fluoro-4-methoxy-pyridin-2-yl)-methylamine Hydrochloride Salt (3-Fluoro-4-methoxy-pyridin-2-ylmethyl)-carbamic acid tert-butyl ester (108 mg, 0.358 mmol) was taken up in iso-propyl alcohol (1 mL) and then HCl (6N in iso-propyl alcohol) (1 mL, 0.578 mmol) was added at rt and left to stir at 40° C. for 2 hrs. The reaction mixture was concentrated under reduced pressure and then triturated with ether, sonicated and then decanted to give a cream coloured solid (75 mg, 55% yield) identified as C-(3-fluoro-4-methoxy-pyridin-2-yl)-methylamine hydrochloride salt.

[MH]⁺=157

H. N-[(3-Fluoro-4-methoxypyridin-2-yl)methyl]-3-(methoxymethyl)-1-({4-[(2-oxopyridin-1-yl)methyl]phenyl}methyl)pyrazole-4-carboxamide (Form A)

3-(Methoxymethyl)-1-(4-((2-oxopyridin-1(2H)-yl)methyl)benzyl)-1H-pyrazole-4-carboxylic acid (825 mg, 2.34 mmol) and C-(3-fluoro-4-methoxy-pyridin-2-yl)-methylamine hydrochloride salt (450 mg, 2.34 mmol) were dissolved in DCM while cooling to 0° C. 1-Ethyl-3-(3-dimethylaminopropyl)carbodiimide hydrochloride (627.0 mg, 3.27 mmol), HOBt (378.8 mg, 2.80 mmol) and triethylamine (1.63 mL, 1182 mmol) were added while stirring, the mixture allowed to warm to rt and stirring continued for 20 hrs. Chloroform (50 mL) was added, the mixture was washed with saturated NaHCO₃(aq) and reduced in vacuo. The crude material was purified by chromatography eluting with methanol/DCM. The resulting solid was dissolved in hot MeCN, allowed to cool and precipitate, and the resulting solids were removed by filtration. The filtrate was reduced in vacuo then freeze dried from MeCN/water to afford the title compound as a white solid (720 mg, 62% yield).

[MH]⁺=492.0

NMR (CD₃OD) δ: 3.41 (3H, s), 4.03 (3H, s), 4.65 (2H, s), 4.72 (2H, d, J=2.3 Hz), 5.24 (2H, s), 5.37 (2H, s), 6.44 (1H, td, J=1.4, 6.8 Hz), 6.62 (1H, d, J=9.0 Hz), 7.18-7.22 (1H, m), 7.31-7.38 (4H, m), 7.56-7.60 (1H, m), 7.75 (1H, dd, J=1.9, 7.1 Hz), 8.18 (1H, s), 8.27 (1H, d, J=5.6 Hz) ppm.

An XRPD diffractogram of N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide (Form A) is shown in FIG. 1b. Form A was found to be mostly amorphous.

Example 2—N-[(3-Fluoro-4-methoxypyridin-2-yl)methyl]-3-(methoxymethyl)-1-({4-[(2-oxopyridin-1-yl)methyl]phenyl}methyl)pyrazole-4-carboxamide (Form 1)

3-(Methoxymethyl)-1-(4-((2-oxopyridin-1(2H)-yl)methyl)benzyl)-1H-pyrazole-4-carboxylic acid (825 mg, 2.34 mmol) and C-(3-fluoro-4-methoxy-pyridin-2-yl)-methylamine hydrochloride salt (450 mg, 2.34 mmol) were dissolved in DCM while cooling to 0° C. 1-Ethyl-3-(3-dimethylaminopropyl)carbodiimide hydrochloride (627.0 mg, 3.27 mmol), HOBt (378.8 mg, 2.80 mmol) and triethylamine (1.63 mL, 1182 mmol) were added while stirring, the mixture allowed to warm to rt and stirring continued for 20 hrs. Chloroform (50 mL) was added, the mixture was washed with saturated NaHCO₃(aq) and reduced in vacuo. The crude material was purified by chromatography eluting with methanol/DCM. The solvent was removed in vacuo and the resulting solid triturated with diethyl ether. The resulting solids were collected by filtration to afford the title compound.

An XRPD diffractogram of N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide (Form 1) is shown in FIG. 2a.

Peak Position Table:

| No. | Pos. [°2Th.] | Rel. Int. [%] |
|---|---|---|
| 1 | 4.436 | 32.36 |
| 2 | 5.0471 | 58.74 |
| 3 | 10.2255 | 43.07 |
| 4 | 11.2061 | 48.44 |
| 5 | 12.0101 | 16.4 |
| 6 | 12.5494 | 37.17 |
| 7 | 13.165 | 67.26 |
| 8 | 14.4984 | 38.94 |
| 9 | 15.8919 | 23.54 |
| 10 | 16.2983 | 34.56 |
| 11 | 17.4492 | 36.63 |
| 12 | 17.8564 | 71.49 |
| 13 | 18.6888 | 21.9 |
| 14 | 20.285 | 26.12 |
| 15 | 21.1598 | 100 |
| 16 | 22.04 | 87.76 |
| 17 | 22.5857 | 36.38 |
| 18 | 23.4408 | 14.33 |
| 19 | 24.3045 | 31.11 |
| 20 | 25.1655 | 78.97 |
| 21 | 25.3728 | 93.91 |
| 22 | 26.4946 | 56.79 |
| 23 | 27.991 | 76.91 |
| 24 | 28.7495 | 22.99 |
| 25 | 30.7611 | 13.4 |
| 26 | 32.413 | 17.2 |
| 27 | 37.2144 | 14.13 |
| 28 | 38.1171 | 14.14 |

Simultaneous Thermal Analysis (STA)

The STA data for Form 1 are shown in FIG. 3.

Differential Scanning Calorimetry (DSC)

The DSC data for Form 1 are shown in FIG. 4.

Gravimetric Vapour Sorption (GVS)

The GVS data for Form 1 are listed in the table below and shown in FIG. 5.

| %-RH | %-Wt(dry basis) |
|---|---|
| 0.0335 | 0.047222 |
| 9.9791 | 0.229954 |
| 20.0169 | 0.354118 |
| 30.0091 | 0.712554 |
| 39.9998 | 0.825004 |
| 49.991 | 1.206867 |
| 59.9808 | 1.698837 |
| 70.0195 | 1.912025 |
| 80.0136 | 2.186122 |
| 90.0039 | 3.226288 |
| 85.0063 | 2.546901 |
| 75.0151 | 2.115841 |
| 64.9759 | 1.86517 |
| 54.9837 | 1.684781 |
| 44.9954 | 1.525476 |
| 35.0052 | 1.017107 |
| 25.0135 | 0.70084 |
| 15.0203 | 0.501709 |
| 4.9801 | 0.126875 |
| 0.0335 | 0.000368 |

Slurry Studies

Form 1 (20 mg) was suspended in 90/10 IPA/water (200 μL or 300 μL) and shaken at ambient temperature for 72 hrs. The supernatant was evaporated rather than filtered due to the small volume and the resulting solid was examined by XRPD (FIG. 6). The resulting XRPD (FIG. 6) was different to that of FIG. 2a which indicated that the free base probably has a tendency to form hydrate(s).

Visual Aqueous Solubility

Form 1 (10 mg) was weighed into a glass vial and water was added in 100 μL portions up to 3 mL then 1 mL portions thereafter. Solubility was assessed visually following a brief period of equilibration.

Form 1 did not give any indication it was dissolving at all in 20 mL water (<<0.5 mg/mL).

Example 3—N-[(3-Fluoro-4-methoxypyridin-2-yl)methyl]-3-(methoxymethyl)-1-({4-[(2-oxopyridin-1-yl)methyl]phenyl}methyl)pyrazole-4-carboxamide (Form 1)

3-(Methoxymethyl)-1-(4-((2-oxopyridin-1(2H)-yl)methyl)benzyl)-1H-pyrazole-4-carboxylic acid (825 mg, 2.34 mmol) and C-(3-fluoro-4-methoxy-pyridin-2-yl)-methylamine hydrochloride salt (450 mg, 2.34 mmol) were dissolved in DCM while cooling to 0° C. 1-Ethyl-3-(3-dimethylaminopropyl)carbodiimide hydrochloride (627.0 mg, 3.27 mmol), HOBt (378.8 mg, 2.80 mmol) and triethylamine (1.63 mL, 1182 mmol) were added while stirring, the mixture allowed to warm to rt and stirring continued for 20 hrs. Chloroform (50 mL) was added, the mixture was washed with saturated NaHCO$_3$(aq) and reduced in vacuo. The crude material was purified by chromatography eluting with methanol/DCM. The resulting solid was dissolved in hot MeCN, allowed to cool and precipitate, and the resulting solids were collected by filtration to afford the title compound as a white solid (130 mg, 11% yield).

An XRPD diffractogram (recorded using Method B) of N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide (Form 1) is shown in FIG. 2b. The XRPD diffractogram (FIG. 2b) of the isolated solids confirmed that they were of the same polymorphic form as Form 1 (Example 2) (FIG. 2a).

Peak Position Table:

| No. | Pos. [°2Th.] | Rel. Int. [%] |
| --- | --- | --- |
| 1 | 4.3928 | 34.22 |
| 2 | 11.108 | 43.43 |
| 3 | 12.4938 | 29.35 |
| 4 | 13.1205 | 36.63 |
| 5 | 13.3366 | 100 |
| 6 | 14.4197 | 49.36 |
| 7 | 15.5175 | 14.68 |
| 8 | 15.8379 | 17.4 |
| 9 | 16.2139 | 51.86 |
| 10 | 17.3752 | 44.76 |
| 11 | 17.7813 | 72.85 |
| 12 | 18.6993 | 39.41 |
| 13 | 20.2369 | 23.49 |
| 14 | 21.126 | 95.26 |
| 15 | 22.012 | 39.31 |
| 16 | 22.5384 | 38.64 |
| 17 | 23.3774 | 25.27 |
| 18 | 24.2866 | 80.45 |
| 19 | 24.7288 | 52.68 |
| 20 | 25.0623 | 70.87 |
| 21 | 25.9156 | 37.33 |
| 22 | 26.5143 | 48.56 |
| 23 | 27.9517 | 49.02 |
| 24 | 28.7252 | 17.67 |
| 25 | 30.7541 | 34.12 |
| 26 | 34.8799 | 20.8 |
| 27 | 37.1548 | 15.95 |
| 28 | 38.1305 | 28 |

Example 4—N-[(3-Fluoro-4-methoxypyridin-2-yl)methyl]-3-(methoxymethyl)-1-({4-[(2-oxopyridin-1-yl)methyl]phenyl}methyl)pyrazole-4-carboxamide (Form 1)

3-(Methoxymethyl)-1-(4-((2-oxopyridin-1(2H)-yl)methyl)benzyl)-1H-pyrazole-4-carboxylic acid (61 g, 0.173 mol) was dissolved in DMF (400 mL) and 1,1'-carbonyldiimidazole (27.99 g, 0.173 mol) was added portion wise. Once the addition was complete, the reaction was heated to 50° C. for 2 hrs. C-(3-fluoro-4-methoxy-pyridin-2-yl)-methylamine (26.95 g, 0.173 mol) was added to the reaction mixture portion wise. The reaction was heated to 50° C. overnight. The reaction was cooled to rt and added dropwise to a 3:1 mixture of water and saturated NaHCO$_3$(aq) (4000 mL). The resulting suspension was stirred for 30 min before isolating the solids by filtration. The solids were washed with water (2×500 mL) before drying in a vacuum oven to give 119 g of the crude product. The crude product was combined with two other separate batches (starting with 0.173 mol and 0.0874 mol of the acid starting material respectively) and slurried together in IPA (1400 mL) and heated to reflux. Additional portions of IPA were added until all of the material had dissolved at reflux (total of 2000 mL IPA added). The solution was held at reflux for 30 min before it was cooled to rt. The mixture was cooled further with an ice/water bath for 30 min before the product was collected by filtration. The solids were washed with IPA and dried to give 167.2 g of the title product (78.5% yield).

[MH]$^+$=491.9

NMR (CD$_3$OD) spectrum conformed to the NMR spectrum of Example 1.

An XRPD diffractogram (recorded using Method B) of the isolated solids (FIG. 2c) confirmed that they were of the same polymorphic form as Form 1 (Example 2 and Example 3) (FIGS. 2a and 2b).

Stability Data

A sample of Form 1 was packed in double polyethylene bags and sealed in a HDPE bottle and stored at conditions of 25° C./60% RH. The sample was reanalysed after 1 month and 3 months by XRPD (using Method B). The data is shown in FIG. 46. No change in the XRPD diffractogram was observed when the sample was stored at 25° C./60% RH after either 1 month or 3 months.

Further tests on the sample of Form 1 stored at 25° C./60% RH were carried out as described in the table below:

| Test | Testing intervals | | |
| --- | --- | --- | --- |
| | Initial | 1 month | 3 months |
| Appearance | Off-white solid | Off-white solid | Off-white solid |
| Identity by retention ratio | 1.00 | 1.00 | 1.00 |
| Purity by HPLC (area %) | 99.70 | 99.62 | 99.70 |
| Total impurities (area %) | 0.30 | 0.38 | 0.30 |
| Assay by HPLC (on an anhydrous and solvent free basis) (% w/w) | 101.0 | 99.5 | 99.6 |
| HPLC assay (on an "as is" basis) (% w/w) | 100.9 | 99.4 | 99.5 |
| Water by Karl Fischer analysis (% w/w) | <0.1 | <0.1 | <0.1 |
| Polymorph by XRPD | Conforms to reference standard (Form 1) | Conforms to reference standard (Form 1) | Conforms to reference standard (Form 1) |

|  | Testing intervals | | |
| --- | --- | --- | --- |
| Test | Initial | 1 month | 3 months |
| DSC Tpeak (° C.) | 152.9 | 152.4 | 152.2 |
| DSC Tonset (° C.) | 151.3 | 151.1 | 150.8 |

A second sample of Form 1 was packed in double polyethylene bags and sealed in a HDPE bottle and stored under accelerated stability conditions of 40° C./75% RH. The sample was reanalysed after 1 month and 3 months by XRPD (using Method B). The data is shown in FIG. 47. No change in the XRPD diffractogram was observed when the sample was stored at 40° C./75% RH after either 1 month or 3 months.

Further tests on the sample of Form 1 stored at 40° C./75% RH were carried out as described in the table below:

|  | Testing intervals | | |
| --- | --- | --- | --- |
| Test | Initial | 1 month | 3 months |
| Appearance | Off-white solid | Off-white solid | Off-white solid |
| Identity by retention ratio | 1.00 | 1.00 | 1.00 |
| Purity by HPLC (area %) | 99.70 | 99.57 | 99.71 |
| Total impurities (area %) | 0.30 | 0.43 | 0.29 |
| Assay by HPLC (on an anhydrous and solvent free basis) (% w/w) | 101.0 | 99.5 | 100.0 |
| HPLC assay (on an "as is" basis) (% w/w) | 100.9 | 99.4 | 99.9 |
| Water by Karl Fischer analysis (% w/w) | <0.1 | <0.1 | 0.1 |
| Polymorph by XRPD | Conforms to reference standard (Form 1) | Conforms to reference standard (Form 1) | Conforms to reference standard (Form 1) |
| DSC Tpeak (° C.) | 152.9 | 152.3 | 152.5 |
| DSC Tonset (° C.) | 151.3 | 151.1 | 150.6 |

Example 5—N-[(3-Fluoro-4-methoxypyridin-2-yl)methyl]-3-(methoxymethyl)-1-({4-[(2-oxopyridin-1-yl)methyl]phenyl}methyl)pyrazole-4-carboxamide (Form 2)

N-[(3-fluoro-4-methoxypyridin-2-yl)methyl]-3-(methoxymethyl)-1-({4-[(2-oxopyridin-1-yl)methyl]phenyl}methyl) pyrazole-4-carboxamide (19.5 mg) in 90/10 PA/water (100 μL) was heated to dissolve the solid, filtering if necessary. The resulting solution was cooled by plunging the warm solution into a liquid nitrogen bath. The sample was then transferred into a freezer. The resulting solids were isolated to afford N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide (Form 2).

An XRPD diffractogram of N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide (Form 2) is shown in FIG. 7.

Peak Position Table:

| No. | Pos. [°2Th.] | Rel. Int. [%] |
| --- | --- | --- |
| 1 | 4.15 | 44.3 |
| 2 | 4.7421 | 100 |
| 3 | 9.463 | 55.02 |
| 4 | 10.8936 | 56.48 |
| 5 | 11.4363 | 21.16 |
| 6 | 14.2897 | 27.16 |
| 7 | 15.28 | 27.17 |
| 8 | 15.7912 | 20.99 |
| 9 | 18.6355 | 15.82 |
| 10 | 19.8599 | 41.02 |
| 11 | 21.389 | 20.04 |
| 12 | 21.9376 | 60.77 |
| 13 | 22.9962 | 20.48 |
| 14 | 23.6679 | 39 |
| 15 | 25.0948 | 29.42 |
| 16 | 26.465 | 33.13 |
| 17 | 29.2936 | 14.19 |

Example 6—N-[(3-Fluoro-4-methoxypyridin-2-yl)methyl]-3-(methoxymethyl)-1-({4-[(2-oxopyridin-1-yl)methyl]phenyl}methyl)pyrazole-4-carboxamide (Form 3)

A suspension of N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide (30 mg) in 50/50 methanol/water (100 μL) was matured by temperature cycling for 2 days. The resulting solids were isolated to afford N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide (Form 3).

An XRPD diffractogram of N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide (Form 3) is shown in FIG. 8.

Peak Position Table:

| No. | Pos. [°2Th.] | Rel. Int. [%] |
| --- | --- | --- |
| 1 | 5.0236 | 100 |
| 2 | 10.0456 | 33.5 |
| 3 | 10.1526 | 38.94 |
| 4 | 12.6705 | 6.8 |
| 5 | 14.8188 | 2.96 |
| 6 | 15.2588 | 2.89 |
| 7 | 16.3621 | 5.53 |
| 8 | 17.5026 | 3.79 |
| 9 | 19.792 | 2.31 |
| 10 | 20.0456 | 3.56 |
| 11 | 20.6393 | 2.71 |
| 12 | 24.1662 | 1.1 |
| 13 | 25.6434 | 1.49 |
| 14 | 26.8451 | 8.57 |
| 15 | 27.6821 | 1.13 |
| 16 | 35.3459 | 3.38 |

Example 7—N-[(3-Fluoro-4-methoxypyridin-2-yl)methyl]-3-(methoxymethyl)-1-({4-[(2-oxopyridin-1-yl)methyl]phenyl}methyl)pyrazole-4-carboxamide (Form 4)

A suspension of N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide (20 mg) in 50/50 methanol/water (100 μL) was heated. Not all of the solid dissolved and therefore the mixture was filtered. The filtrate was allowed to evaporate under nitrogen to afford N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide (Form 4).

An XRPD diffractogram of N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide (Form 4) is shown in FIG. 9.

Example 8 to Example 20—Salt Screen Data

A salt screen of N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide was carried out and XRPD diffractograms recorded of the products.

If the counter-ion was a solid (p-toluenesulphonic acid, ethanedisulphonic acid and benzene sulfonic acid), N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide (~15 mg) was weighed into a vial with ~1.1 equivalents of the counter-ion as a physical solid mixture. 150 μL of the appropriate solvent was added. If the counter ion was a liquid (5M hydrochloric acid, 6M sulphuric acid, 85% orthophosphoric acid, methane sulphonic acid) the appropriate volume corresponding to ~1.1 equivalents was added to N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide (~15 mg) in the chosen solvent (150 μL) (mostly suspension).

The mixture was shaken well by hand. All slurries or solutions were then temperature-cycled between ambient and 40° C. for ~18-24 hrs.

If enough solid was present the supernatant was decanted off, if possible, and the solid dried by evaporation. If a solution was observed, the solvent was allowed to evaporate under nitrogen then dried. Any solids were examined by XRPD.

Example 8—N-[(3-Fluoro-4-methoxypyridin-2-yl)methyl]-3-(methoxymethyl)-1-({4-[(2-oxopyridin-1-yl)methyl]phenyl}methyl)pyrazole-4-carboxamide Hydrochloride (Form 5)

Obtained using the salt screen method described above when the solvent is EtOAc or MeCN. Acid is 5M hydrochloric acid.

An XRPD diffractogram of Form 5 is shown in FIG. 10.

Example 9—N-[(3-Fluoro-4-methoxypyridin-2-yl)methyl]-3-(methoxymethyl)-1-({4-[(2-oxopyridin-1-yl)methyl]phenyl}methyl)pyrazole-4-carboxamide Hydrochloride (Form 6)

Obtained using the salt screen method described above when solvent is acetone. Acid is 5M hydrochloric acid.

An XRPD diffractogram of Form 6 is shown in FIG. 11.

Example 10—N-[(3-Fluoro-4-methoxypyridin-2-yl)methyl]-3-(methoxymethyl)-1-({4-[(2-oxopyridin-1-yl)methyl]phenyl}methyl)pyrazole-4-carboxamide Hydrochloride (Form 7)

Obtained using the salt screen method described above when solvent is THF. Acid is 5M hydrochloric acid.

An XRPD diffractogram of Form 7 is shown in FIG. 12.

Example 11—Sulfate salt of N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide (Form 8)

Obtained using the salt screen method described above when solvent is acetone or MeCN. Acid is 6M sulphuric acid.

An XRPD diffractogram of Form 8 is shown in FIG. 13.

Example 12—Phosphate salt of N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide (Form 9)

Obtained using the salt screen method described above when solvent is acetone. Acid is 85% orthophosphoric acid.

An XRPD diffractogram of Form 9 is shown in FIG. 14.
Peak Position Table:

| No. | Pos. [°2Th.] | Rel. Int. [%] |
|---|---|---|
| 1 | 4.4532 | 29.03 |
| 2 | 6.8089 | 6.4 |
| 3 | 7.2372 | 15.96 |
| 4 | 9.5928 | 22.07 |
| 5 | 10.0927 | 22.55 |
| 6 | 13.4475 | 31.38 |
| 7 | 14.4842 | 31.22 |
| 8 | 16.2685 | 77.62 |
| 9 | 17.2526 | 75.29 |
| 10 | 17.767 | 44.33 |
| 11 | 18.9329 | 76.89 |
| 12 | 19.2954 | 47.63 |
| 13 | 19.7409 | 29.56 |
| 14 | 20.4598 | 100 |
| 15 | 21.1934 | 38.24 |
| 16 | 22.9919 | 68.51 |
| 17 | 23.6995 | 54.45 |
| 18 | 25.4212 | 55.32 |
| 19 | 27.1889 | 44.13 |

Example 13—Phosphate salt of N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide (Form 10)

Obtained using the salt screen method described above when solvent is EtOAc. Acid is 85% orthophosphoric acid.

An XRPD diffractogram of Form 10 is shown in FIG. 15.

Example 14—Phosphate salt of N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide (Form 11)

Obtained using the salt screen method described above when solvent is THF. Acid is 85% orthophosphoric acid.

An XRPD diffractogram of Form 11 is shown in FIG. 16.

Example 15—N-[(3-Fluoro-4-methoxypyridin-2-yl)methyl]-3-(methoxymethyl)-1-({4-[(2-oxopyridin-1-yl)methyl]phenyl}methyl)pyrazole-4-carboxamide Mesylate (Form 12)

Obtained using the salt screen method described above when solvent is THF. Acid is methane sulphonic acid.

An XRPD diffractogram of Form 12 is shown in FIG. 17.

Peak Position Table:

| No. | Pos. [°2Th.] | Rel. Int. [%] |
|---|---|---|
| 1 | 4.9941 | 51.33 |
| 2 | 6.7123 | 7.1 |
| 3 | 10.0046 | 14.02 |
| 4 | 13.7899 | 14.91 |
| 5 | 14.7949 | 30.6 |
| 6 | 15.464 | 5.41 |
| 7 | 16.426 | 10.73 |
| 8 | 19.1813 | 31.02 |
| 9 | 20.3174 | 56.5 |
| 10 | 21.4928 | 32.46 |
| 11 | 23.2555 | 100 |
| 12 | 23.9691 | 26.22 |
| 13 | 25.0137 | 12.94 |
| 14 | 26.1511 | 33.19 |
| 15 | 27.6423 | 14.16 |
| 16 | 28.8844 | 14.26 |
| 17 | 29.6868 | 4.92 |
| 18 | 30.6702 | 9.54 |
| 19 | 32.9271 | 4.06 |

Example 16—N-[(3-Fluoro-4-methoxypyridin-2-yl)methyl]-3-(methoxymethyl)-1-({4-[(2-oxopyridin-1-yl)methyl]phenyl}methyl)pyrazole-4-carboxamide Mesylate (Form 13)

Obtained using the salt screen method described above when solvent is acetone. Acid is methane sulphonic acid.

An XRPD diffractogram of Form 13 is shown in FIG. 18.

Example 17—N-[(3-Fluoro-4-methoxypyridin-2-yl)methyl]-3-(methoxymethyl)-1-({4-[(2-oxopyridin-1-yl)methyl]phenyl}methyl)pyrazole-4-carboxamide Tosylate (Form 14)

Obtained using the salt screen method described above when solvent is acetone, EtOAc, THF or MeCN. Acid is p-toluenesulfonic acid.

An XRPD diffractogram of Form 14 is shown in FIG. 19.

Peak Position Table:

| No. | Pos. [°2Th.] | Rel. Int. [%] |
|---|---|---|
| 1 | 4.9848 | 100 |
| 2 | 9.6143 | 25.67 |
| 3 | 12.7816 | 8.72 |
| 4 | 13.746 | 27.51 |
| 5 | 14.9399 | 14.77 |
| 6 | 16.3881 | 12.36 |
| 7 | 17.7628 | 37.11 |
| 8 | 18.7538 | 21.38 |
| 9 | 19.0483 | 19.01 |
| 10 | 20.058 | 29.04 |
| 11 | 21.0667 | 15.21 |
| 12 | 21.8804 | 11.45 |
| 13 | 23.2525 | 43.04 |
| 14 | 23.5975 | 35.45 |
| 15 | 24.2188 | 30.99 |
| 16 | 25.1144 | 13.88 |
| 17 | 28.6941 | 19.47 |
| 18 | 29.7918 | 7.64 |

Example 18—Edisylate salt of N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide (Form 15)

Obtained using the salt screen method described above when solvent is acetone or EtOAc. Acid is ethanedisulfonic acid.

An XRPD diffractogram of Form 15 is shown in FIG. 20.

Example 19—Edisylate salt of N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide (Form 16)

Obtained using the salt screen method described above when solvent is THF or MeCN. Acid is ethanedisulfonic acid.

An XRPD diffractogram of Form 16 is shown in FIG. 21.

Example 20—N-[(3-Fluoro-4-methoxypyridin-2-yl)methyl]-3-(methoxymethyl)-1-({4-[(2-oxopyridin-1-yl)methyl]phenyl}methyl)pyrazole-4-carboxamide Besylate (Form 17)

Obtained using the salt screen method described above when solvent is acetone, EtOAc, THF or MeCN. Acid is benzenesulfonic acid.

An XRPD diffractogram of Form 17 is shown in FIG. 22.

Peak Position Table:

| No. | Pos. [°2Th.] | Rel. Int. [%] |
|---|---|---|
| 1 | 5.3346 | 100 |
| 2 | 9.7624 | 59.63 |
| 3 | 10.6521 | 9.96 |
| 4 | 12.7094 | 6.69 |
| 5 | 14.2147 | 7.84 |
| 6 | 14.9024 | 31.52 |
| 7 | 15.5992 | 5.61 |
| 8 | 16.3806 | 26.39 |
| 9 | 17.4003 | 20.58 |
| 10 | 19.2425 | 50.9 |
| 11 | 19.9071 | 58.63 |
| 12 | 20.9547 | 19.07 |
| 13 | 21.7211 | 13.78 |
| 14 | 22.261 | 24.2 |
| 15 | 23.1455 | 44.91 |
| 16 | 23.5866 | 19.8 |
| 17 | 24.5696 | 86.07 |
| 18 | 25.101 | 10.78 |
| 19 | 25.8617 | 22.03 |
| 20 | 26.6751 | 5.56 |
| 21 | 28.6473 | 10.33 |
| 22 | 29.1826 | 10.1 |
| 23 | 30.105 | 12.42 |
| 24 | 31.4456 | 4.01 |
| 25 | 38.5373 | 4.52 |

Example 21 to Example 25—Scale-Up Experiments

Example 21—N-[(3-Fluoro-4-methoxypyridin-2-yl)methyl]-3-(methoxymethyl)-1-({4-[(2-oxopyridin-1-yl)methyl]phenyl}methyl)pyrazole-4-carboxamide Hydrochloride (Form 18)

N-[(3-Fluoro-4-methoxypyridin-2-yl)methyl]-3-(methoxymethyl)-1-({4-[(2-oxopyridin-1-yl)methyl]phenyl}methyl)pyrazole-4-carboxamide (200 mg) was heated in MeCN (2 mL) so that the solid dissolved. A few crystals of primary screen sample (Form 5) were added to the warm solution followed by 5M hydrochloric acid (90 L) was added and mixed well. An oily solid separated and the mixture was ultrasonicated for ~1 min and the product was scratched with a spatula. The resulting suspension was temperature-cycled between 40° C. and ambient temperature overnight (18-24 hrs). The product amassed and MeCN (1 mL) was added to mobilise before the product was filtered, washed with MeCN (2×1 mL) and dried in a vacuum oven at 50° C. for ~24 hrs to constant weight. (Yield 122 mg)

An NMR spectrum of the isolated product in d6-DMSO is shown in FIG. 23.

An XRPD diffractogram of the isolated product (top) overlaid with Form 5 (Example 8) (bottom) is shown in FIG. 24. The XRPD diffractograms showed that the isolated product (Form 18) was a different polymorphic form to that of Form 5.

Peak Position Table for Form 18:

| No. | Pos. [°2Th.] | Rel. Int. [%] |
| --- | --- | --- |
| 1 | 5.5212 | 100 |
| 2 | 7.2946 | 31.59 |
| 3 | 8.5234 | 46.13 |
| 4 | 11.6264 | 77.11 |
| 5 | 13.2243 | 35.95 |
| 6 | 14.6627 | 13.33 |
| 7 | 15.9994 | 10.62 |
| 8 | 17.0327 | 53.91 |
| 9 | 18.9939 | 47.87 |
| 10 | 20.6054 | 24.18 |
| 11 | 21.7408 | 18.27 |
| 12 | 22.8017 | 71.36 |
| 13 | 23.7665 | 40.19 |
| 14 | 26.1807 | 46.6 |
| 15 | 28.1871 | 19.34 |
| 16 | 29.3436 | 16.04 |
| 17 | 30.6655 | 11.07 |

Simultaneous Thermal Analysis (STA)

The STA data for Form 18 are shown in FIG. 25.
Differential Scanning Calorimetry (DSC)

The DSC data for Form 18 are shown in FIG. 26.
Gravimetric Vapour Sorption (GVS)

The GVS data for Form 18 are listed in the table below and shown in FIG. 27.

| %-RH | %-Wt(dry basis) |
| --- | --- |
| 0.034 | 0.000338 |
| 9.9796 | 0.236408 |
| 20.0179 | 0.372259 |
| 30.0076 | 0.503656 |
| 39.9983 | 0.661778 |
| 49.99 | 0.924572 |
| 59.9827 | 9.109051 |
| 70.02 | 9.603459 |
| 80.0151 | 13.9262 |
| 90.0014 | 66.83245 |
| 85.0058 | 40.15885 |
| 75.0166 | 24.50478 |
| 64.9759 | 17.33807 |
| 54.9871 | 12.7659 |
| 44.9765 | 9.623504 |
| 35.0013 | 7.124732 |
| 25.013 | 4.993427 |
| 15.0213 | 3.447841 |
| 4.9816 | 2.227407 |
| 0.0335 | 0.349988 |

Slurry Studies

Form 18 (20 mg) was suspended in 90/10 IPA/water (200 μL or 300 μL) and shaken at ambient temperature for 72 hrs. The supernatant was evaporated rather than filtered due to the small volume and the resulting solid was examined by XRPD (FIG. 28). The resulting XRPD (FIG. 28) showed that the resulting form after slurry with 90/10 IPA/water was different to that of Form 18.

Visual Aqueous Solubility

Form 18 (10 mg) was weighed into a glass vial and water was added in 100 μL portions up to 3 mL then 1 mL portions thereafter. Solubility was assessed visually following a brief period of equilibration.

Form 18 appeared to dissolve initially in 0.1 mL of water, but then reprecipitated. The solid did not then dissolve again up to 20 mL.

Example 22—Sulfate salt of N-[(3-fluoro-4-methoxypyridin-2-yl)methyl]-3-(methoxymethyl)-1-({4-[(2-oxopyridin-1-yl)methyl]phenyl}methyl) pyrazole-4-carboxamide (Form 8)

N-[(3-Fluoro-4-methoxypyridin-2-yl)methyl]-3-(methoxymethyl)-1-({4-[(2-oxopyridin-1-yl)methyl] phenyl}methyl)pyrazole-4-carboxamide (200 mg) was heated in acetonitrile (2 mL) so that the solid dissolved. 6M sulphuric acid (75 L) was added to the warm solution, mixed well and ultrasonicated immediately after mixing. A slightly cloudy solution with a small quantity of oil was observed but no crystals were precipitated. A few crystals of primary screen sample were added at ambient temperature and solid rapidly amassed on further ultrasonication. The resulting suspension was temperature-cycled between 40° C. and ambient temperature overnight (18-24 hrs). The product was filtered, washed with MeCN (2×1 mL) and dried in a vacuum oven at 50° C. for 24 hrs to constant weight. (Yield 133 mg).

An NMR spectrum of the isolated product in d6-DMSO is shown in FIG. 29.

An XRPD diffractogram of the isolated product (top) overlaid with the screening sample of Form 8 (Example 11) (bottom) is shown in FIG. 30. The XRPD diffractograms showed that the polymorphic form of the isolated product was the same as the polymorphic form of the screening sample of Form 8 (Example 11).

Peak Position Table for Form 8:

| No. | Pos. [°2Th.] | Rel. Int. [%] |
| --- | --- | --- |
| 1 | 5.095 | 31.62 |
| 2 | 7.4926 | 14.43 |
| 3 | 11.3026 | 10.33 |
| 4 | 12.0297 | 35.43 |
| 5 | 12.6152 | 14.36 |
| 6 | 13.2265 | 22.14 |
| 7 | 14.7487 | 13.8 |
| 8 | 15.1698 | 33.09 |
| 9 | 16.6928 | 11.02 |
| 10 | 17.8991 | 21.59 |
| 11 | 18.2272 | 22.27 |
| 12 | 19.2643 | 26.73 |
| 13 | 19.8687 | 38.21 |
| 14 | 20.1287 | 100 |
| 15 | 22.2453 | 32.59 |
| 16 | 22.7734 | 30.97 |
| 17 | 24.391 | 86.73 |
| 18 | 25.7855 | 29.06 |
| 19 | 27.3382 | 16.22 |
| 20 | 28.9485 | 9.94 |
| 21 | 30.1898 | 18.8 |
| 22 | 32.6891 | 11.46 |

Simultaneous Thermal Analysis (STA)
The STA data for Form 8 are shown in FIG. 31.
Differential Scanning Calorimetry (DSC)
The DSC data for Form 8 are shown in FIG. 32.
Gravimetric Vapour Sorption (GVS)
The GVS data for Form 8 are listed in the table below and shown in FIG. 33.

| %-RH | %-Wt(dry basis) |
|---|---|
| 0.034 | 0.039462 |
| 9.9777 | 0.440403 |
| 20.0179 | 0.616343 |
| 30.0076 | 0.777058 |
| 39.9993 | 0.638336 |
| 49.9891 | 0.873486 |
| 59.9817 | 1.213525 |
| 70.0229 | 2.0577 |
| 80.0122 | 3.989659 |
| 90.0029 | 14.16036 |
| 85.0092 | 6.295491 |
| 75.017 | 3.436462 |
| 64.9744 | 1.643225 |
| 54.9837 | 0.949614 |
| 44.9949 | 0.563899 |
| 35.0037 | 0.245853 |
| 25.011 | 0.394726 |
| 15.0203 | 0.228936 |
| 4.9806 | 0.078372 |
| 0.0335 | 0.000552 |

Slurry Studies
Form 8 (20 mg) was suspended in 90/10 IPA/water (200 µL or 300 µL) and shaken at ambient temperature for 72 hrs. The supernatant was evaporated rather than filtered due to the small volume and the resulting solid was examined by XRPD (FIG. 34). There was no change in the X-ray pattern following slurry in 90/10 IPA/water.
Visual Aqueous Solubility
Form 8 (10 mg) was weighed into a glass vial and water was added in 100 µL portions up to 3 mL then 1 mL portions thereafter. Solubility was assessed visually following a brief period of equilibration.
Form 8 completely dissolved in 0.1 mL of water (~>>100 mg/mL).

Example 23—N-[(3-Fluoro-4-methoxypyridin-2-yl)methyl]-3-(methoxymethyl)-1-({4-[(2-oxopyridin-1-yl)methyl]phenyl}methyl)pyrazole-4-carboxamide Sulfate (Form 8)

N-[(3-Fluoro-4-methoxypyridin-2-yl)methyl]-3-(methoxymethyl)-1-({4-[(2-oxopyridin-1-yl)methyl]phenyl}methyl)pyrazole-4-carboxamide (2.00 g, 4.07 mmol) was stirred in MeCN (25 mL). The mixture was heated to 65° C. and held at this temperature until all of the starting material had dissolved. To the warm solution, 6M aqueous sulphuric acid (0.75 mL, 4.5 mmol) was added. The mixture was stirred vigorously and a white solid was formed. The mixture was cooled to rt and the solids were isolated by filtration, washing with small portions of MeCN. The solids were dried for 24 hrs at 45° C. to give the title compound (2.6 g).
[MH]$^+$=491.5
NMR (CD$_3$OD) δ: 3.40 (3H, s), 4.26 (3H, s), 4.67 (2H, s), 4.82 (2H, d, J=1.6 Hz), 5.23 (2H, s), 5.35 (2H, s), 6.42-6.48 (1H, m), 6.61 (1H, d, J=9.2 Hz), 7.30 and 7.34 (each 2H, each d, J=8.2 Hz), 7.54-7.62 (1H, m), 7.72-7.80 (2H, m), 8.18 (1H, d, J=1.5 Hz), 8.54 (1H, d, J=6.9 Hz) ppm.

An XRPD diffractogram (recorded using Method B) of the isolated product is shown in FIG. 35. The XRPD diffractogram showed that the polymorphic form of the isolated product was the same as the polymorphic form of the scaled-up sample of Form 8 in Example 22.

Example 24—N-[(3-Fluoro-4-methoxypyridin-2-yl)methyl]-3-(methoxymethyl)-1-({4-[(2-oxopyridin-1-yl)methyl]phenyl}methyl)pyrazole-4-carboxamide Edisylate (Form 15)

Ethane disulphonic acid hydrate (85 mg) and N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide (200 mg) were weighed into a glass vial and acetone (2 mL) was added to the physical solid mixture. The resulting suspension was heated but no dissolution was observed. Following ultrasonication, the mixture was triturated with a spatula to dislodge slightly oily solid form the bottom of the vial. The resulting suspension was temperature-cycled between 40° C. and ambient temperature overnight (18-24 hours). The product was filtered, washed with acetone (2×1 mL) and dried in a vacuum oven at 50° C. for 24 hours to constant weight. (Yield 158 mg).
An NMR spectrum of the isolated product in d6-DMSO is shown in FIG. 36.
An XRPD diffractogram of the isolated product (top) overlaid with the screening sample of Form 15 (Example 18) (bottom) is shown in FIG. 37. The XRPD diffractograms indicated that the isolated product was not as crystalline as the primary screen sample (Form 15, Example 18) as revealed by intensity of peaks, but the pattern was consistent with that obtained in the primary screen (Example 18).
Peak Position Table for Form 15:

| No. | Pos. [°2Th.] | Rel. Int. [%] |
|---|---|---|
| 1 | 5.1425 | 9.55 |
| 2 | 7.711 | 30.18 |
| 3 | 9.8944 | 8.48 |
| 4 | 10.2988 | 37.76 |
| 5 | 12.0881 | 11.57 |
| 6 | 13.4235 | 25.73 |
| 7 | 14.4371 | 27.45 |
| 8 | 15.6664 | 26.3 |
| 9 | 18.3462 | 100 |
| 10 | 19.4459 | 84.42 |
| 11 | 20.6911 | 65.05 |
| 12 | 21.9894 | 18.54 |
| 13 | 23.2278 | 23.94 |
| 14 | 24.1041 | 62.77 |
| 15 | 25.0706 | 64.44 |
| 16 | 25.6886 | 68.88 |
| 17 | 26.2107 | 27.72 |
| 18 | 28.2107 | 41.92 |
| 19 | 30.7149 | 38.27 |
| 20 | 32.0375 | 20.74 |
| 21 | 37.3892 | 11.25 |
| 22 | 32.9803 | 16.23 |
| 23 | 34.1795 | 26.32 |

Simultaneous Thermal Analysis (STA)
The STA data for Form 15 are shown in FIG. 38.
Differential Scanning Calorimetry (DSC)
The DSC data for Form 15 are shown in FIG. 39.
Slurry Studies
An attempt to prepare a water slurry by mixing Form 15 (20 mg) and deionised water (200 µL) for 72 hrs resulted in complete dissolution of the sample.

Form 15 (20 mg) was suspended in 90/10 IPA/water (200 µL or 300 µL) and shaken at ambient temperature for 72 hrs. The supernatant was evaporated rather than filtered due to the small volume and the resulting solid was examined by XRPD (FIG. 40). There were no differences in X-ray pattern following slurry in 90/10 IPA/water.

Visual Aqueous Solubility

Form 15 (10 mg) was weighed into a glass vial and water was added in 100 µL portions up to 3 mL then 1 mL portions thereafter. Solubility was assessed visually following a brief period of equilibration.

Form 15 completely dissolved in 0.1 mL of water (~>>100 mg/mL) and then on repeat using even less water in 0.05 mL (>200 mg/mL).

Example 25—N-[(3-Fluoro-4-methoxypyridin-2-yl)methyl]-3-(methoxymethyl)-1-({4-[(2-oxopyridin-1-yl)methyl]phenyl}methyl)pyrazole-4-carboxamide Edisylate (Form 16)

Ethane disulphonic acid hydrate (85 mg) and N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide (200 mg) were weighed into a glass vial and acetonitrile (2 mL) was added to the physical solid mixture. The resulting suspension was heated and most of the solid dissolved except for a single agglomerate of acid. Crystals precipitated at the higher temperature before a completely clear solution was obtained. The slightly oily product was ultrasonicated and triturated with a spatula and remaining oil solidified and dispersed. The resulting suspension was temperature-cycled between 40° C. and ambient temperature overnight (18-24 hrs). The product was filtered, washed with acetonitrile (2×1 mL) and dried in a vacuum oven at 50° C. for 24 hrs to constant weight. (Yield 162 mg).

An NMR spectrum of the isolated product in d6-DMSO is shown in FIG. 41.

An XRPD diffractogram of the isolated product (top) overlaid with the screening sample of Form 16 (Example 19) (bottom) is shown in FIG. 42. The XRPD diffractograms indicated that the isolated product was not as crystalline as the primary screen sample (Form 16, Example 19) as revealed by intensity of peaks, but the pattern was consistent with that obtained in the primary screen (Example 19).

Peak Position Table for Form 16:

| No. | Pos. [°2Th.] | Rel. Int. [%] |
|---|---|---|
| 1 | 5.1694 | 14.42 |
| 2 | 6.0845 | 9.76 |
| 3 | 7.7237 | 13.84 |
| 4 | 10.4192 | 35.13 |
| 5 | 13.4025 | 19.6 |
| 6 | 14.5581 | 18.11 |
| 7 | 16.0635 | 32.97 |
| 8 | 16.4918 | 31.4 |
| 9 | 18.4628 | 59.18 |
| 10 | 19.5103 | 65.78 |
| 11 | 20.8042 | 71.86 |
| 12 | 21.4525 | 52.29 |
| 13 | 22.4337 | 100 |
| 14 | 22.9305 | 39.42 |
| 15 | 23.2622 | 40.85 |
| 16 | 24.1582 | 82.29 |
| 17 | 25.2037 | 66.66 |
| 18 | 26.2617 | 35.09 |
| 19 | 28.2948 | 19.45 |
| 20 | 29.4186 | 15.75 |
| 21 | 32.1152 | 13.58 |
| 22 | 32.9803 | 16.23 |
| 23 | 34.1795 | 26.32 |

Simultaneous Thermal Analysis (STA)

The STA data for Form 16 are shown in FIG. 43.

Differential Scanning Calorimetry (DSC)

The DSC data for Form 16 are shown in FIG. 44.

Gravimetric Vapour Sorption (GVS)

The GVS data for Form 16 are listed in the table below and shown in FIG. 45.

| %-RH | %-Wt(dry basis) |
|---|---|
| 0.0335 | 1.611676 |
| 9.9772 | 2.367329 |
| 20.0183 | 2.626044 |
| 30.0066 | 2.833529 |
| 40.0022 | 3.044856 |
| 49.9895 | 3.350959 |
| 59.9808 | 7.516016 |
| 70.0195 | 9.935387 |
| 80.0122 | 15.98189 |
| 89.9044 | 94.25731 |
| 85.0073 | 57.40449 |
| 75.02 | 33.15955 |
| 64.9773 | 23.21695 |
| 54.9876 | 17.20631 |
| 44.9876 | 12.93879 |
| 35.0032 | 9.563965 |
| 25.012 | 6.541352 |
| 15.0203 | 4.494685 |
| 4.9811 | 2.865548 |
| 0.0335 | 0.00047 |

Visual Aqueous Solubility

Form 16 (10 mg) was weighed into a glass vial and water was added in 100 µL portions up to 3 mL then 1 mL portions thereafter. Solubility was assessed visually following a brief period of equilibration.

Form 16 completely dissolved in 0.1 mL of water (~>>100 mg/mL) and then on repeat using even less water in 0.05 mL (>200 mg/mL).

Example 26—Biological Methods

The ability of N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide to inhibit plasma kallikrein may be determined using the following biological assays:

Determination of the $IC_{50}$ for Plasma Kallikrein

Plasma kallikrein inhibitory activity in vitro was determined using standard published methods (see e.g. Johansen et al., Int. J. Tiss. Reac. 1986, 8, 185: Shori et al., Biochem. Pharmacol., 1992, 43, 1209; Stürzebecher et al., Biol. Chem. Hoppe-Seyler, 1992, 373, 1025). Human plasma kallikrein (Protogen) was incubated at 25° C. with the fluorogenic substrate H-DPro-Phe-Arg-AFC and various concentrations of the test compound. Residual enzyme activity (initial rate of reaction) was determined by measuring the change in optical absorbance at 410 nm and the $IC_{50}$ value for the test compound was determined.

When tested in this assay, N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide showed an $IC_{50}$ (human PKal) of 3.3 nM.

N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide was also screened for inhibitory activity against the related enzyme KLK1 using the following biological assay:

Determination of the $IC_{50}$ for KLK1

KLK1 inhibitory activity in vitro was determined using standard published methods (see e.g. Johansen et al., Int. J. Tiss. Reac. 1986, 8, 185; Shori et al., Biochem. Pharmacol., 1992, 43, 1209; Sturzebecher et al., Biol. Chem. Hoppe-Seyler, 1992, 373, 1025). Human KLK1 (Callbiochem) was incubated at 25° C. with the fluorogenic substrate H-DVal-Leu-Arg-AFC and various concentrations of the test compound. Residual enzyme activity (initial rate of reaction) was determined by measuring the change in optical absorbance at 410 nm and the $IC_{50}$ value for the test compound was determined.

When tested in this assay, N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide showed an $IC_{50}$ (human KLK1) of >40000 n M.

N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide was also screened for inhibitory activity against the related enzyme FXIa using the following biological assay:

Determination of the % Inhibition for FXIa

FXIa inhibitory activity in vitro was determined using standard published methods (see e.g. Johansen et al., Int. J. Tiss. Reac. 1986, 8, 185; Shori et al., Biochem. Pharmacol., 1992, 43, 1209; Stürzebecher et al., Biol. Chem. Hoppe-Seyler, 1992, 373, 1025). Human FXIa (Enzyme Research Laboratories) was incubated at 25° C. with the fluorogenic substrate Z-Gly-Pro-Arg-AFC and 40 μM of the test compound. Residual enzyme activity (initial rate of reaction) was determined by measuring the change in optical absorbance at 410 nm.

When tested in this assay, N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide showed a % inhibition @ 40 μM (human FXIIa) of 0%.

Example 27—Pharmacokinetics

A pharmacokinetic study of N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide was performed to assess the pharmacokinetics following a single oral dose in male Sprague-Dawley rats. Two rats were given a single po dose of 5 mL/kg of a nominal 2 mg/mL (10 mg/kg) composition of test compound in vehicle. Following dosing, blood samples were collected over a period of 24 hrs. Sample times were 5, 15 and 30 minutes then 1, 2, 4, 6, 8 and 12 hrs. Following collection, blood samples were centrifuged and the plasma fraction analysed for concentration of test compound by LCMS.

Oral exposure data acquired from this study for N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide is shown below:

| Vehicle | Dose po (mg/kg) | Cmax (ng/mL) | Tmax (min) |
|---|---|---|---|
| 10% DMSO/ 10% cremophor/ 80% SWFI | 10.5 | 1534 | 180 |
| D-α-Tocopherol polyethylene glycol 1000 succinate (TPGS) solution (20% aq. w/v) | 10.1 | 1942 | 70 |

The invention claimed is:

1. A crystalline form of N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide, that is crystalline form 1 of N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide, which exhibits at least X-ray powder diffraction peaks (Cu Kα radiation, expressed in degrees 2θ) at 11.2±0.3, 12.5±0.3, 13.2±0.3, 14.5±0.3, and 16.3±0.3.

2. The crystalline form 1 of claim 1 having an X-ray powder diffraction pattern that is substantially the same as that shown in FIG. 2a.

3. The crystalline form 1 of claim 1, which exhibits an endothermic peak in its DSC thermograph at 151±3° C.

4. The crystalline form 1 of claim 1 having a DSC thermograph substantially the same as that shown in FIG. 4.

5. A crystalline form 1 of N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide, which exhibits an endothermic peak in its DSC thermograph at 151±3° C.

6. The crystalline form 1 of claim 5 having a DSC thermograph substantially the same as that shown in FIG. 4.

7. A pharmaceutical composition comprising a crystalline form of claim 1 and a pharmaceutically acceptable adjuvant, diluent or carrier.

8. A process for preparing a crystalline form 1 of claim 1, comprising heating a mixture of N-[(3-fluoro-4-methoxypyridin-2-yl)methyl]-3-(methoxymethyl)-1-({4-[(2-oxopyridin-1-yl)methyl]phenyl}methyl)pyrazole-4-carboxamide and acetonitrile or isopropanol; and then cooling the mixture.

9. The process of claim 8, wherein the temperature of the heating is 60 to 85° C.

10. The process of claim 9, wherein the temperature for the cooling is 0 to 40° C.

11. A method for preparing a pharmaceutical composition comprising combining the crystalline form of claim 1 and one or more pharmaceutically acceptable carrier, diluent, or excipient.

* * * * *

UNITED STATES PATENT AND TRADEMARK OFFICE
CERTIFICATE OF CORRECTION

| | |
|---|---|
| PATENT NO. | : 11,230,537 B2 |
| APPLICATION NO. | : 16/303334 |
| DATED | : January 25, 2022 |
| INVENTOR(S) | : Beaton et al. |

It is certified that error appears in the above-identified patent and that said Letters Patent is hereby corrected as shown below:

On the Title Page

Item (72): delete:
"Inventors: Haydn Beaton, Loughborough, United Kingdom;
David Malcolm Crowe, Reading, United Kingdom;
Hannah Joy Edwards, Wiltshire, United Kingdom;
Nicholas James Griffiths-Haynes, Warwickshire, United Kingdom"

And substitute therefor:
-- Inventors: Haydn Beaton, Loughborough, United Kingdom;
David Malcolm Crowe, Reading, United Kingdom;
Hannah Joy Edwards, Wiltshire, United Kingdom --

Signed and Sealed this
Eighth Day of August, 2023

Katherine Kelly Vidal
*Director of the United States Patent and Trademark Office*